(12) United States Patent
Bender et al.

(10) Patent No.: US 11,096,996 B2
(45) Date of Patent: Aug. 24, 2021

(54) CANCER VACCINES AND VACCINATION METHODS

(71) Applicant: Precision Lifesciences Group LLC, Nashville, TN (US)

(72) Inventors: James G. Bender, Rancho Santa Margarita, CA (US); John S. Yu, Los Angeles, CA (US)

(73) Assignee: Precision Lifesciences Group LLC, Nashville, TN (US)

( * ) Notice: Subject to any disclaimer, the term of this patent is extended or adjusted under 35 U.S.C. 154(b) by 128 days.

(21) Appl. No.: 16/167,096

(22) Filed: Oct. 22, 2018

(65) Prior Publication Data

US 2019/0275127 A1 Sep. 12, 2019

Related U.S. Application Data

(62) Division of application No. 14/766,685, filed as application No. PCT/US2014/016610 on Feb. 14, 2014, now Pat. No. 10,137,182.

(60) Provisional application No. 61/764,789, filed on Feb. 14, 2013.

(51) Int. Cl.
| | |
|---|---|
| *A61K 38/00* | (2006.01) |
| *A61K 39/00* | (2006.01) |
| *A61K 45/06* | (2006.01) |
| *A61K 31/675* | (2006.01) |
| *C12N 5/0784* | (2010.01) |

(52) U.S. Cl.
CPC ........ *A61K 39/0011* (2013.01); *A61K 31/675* (2013.01); *A61K 39/00115* (2018.08); *A61K 39/00117* (2018.08); *A61K 39/001106* (2018.08); *A61K 39/001119* (2018.08); *A61K 39/001122* (2018.08); *A61K 39/001151* (2018.08); *A61K 39/001153* (2018.08); *A61K 39/001157* (2018.08); *A61K 39/001164* (2018.08); *A61K 39/001166* (2018.08); *A61K 39/001168* (2018.08); *A61K 39/001186* (2018.08); *A61K 39/001188* (2018.08); *A61K 45/06* (2013.01); *C12N 5/0639* (2013.01); *A61K 38/00* (2013.01); *A61K 2039/5154* (2013.01); *A61K 2039/6006* (2013.01); *C12N 2501/22* (2013.01); *C12N 2501/25* (2013.01); *C12N 2506/115* (2013.01)

(58) Field of Classification Search
CPC ............................. A61K 38/00; A61K 39/0011
See application file for complete search history.

(56) References Cited

U.S. PATENT DOCUMENTS

| | | | |
|---|---|---|---|
| 4,690,915 A | 9/1987 | Rosenberg | |
| 4,844,893 A | 7/1989 | Honsik et al. | |
| 5,635,363 A | 6/1997 | Altman et al. | |
| 5,643,786 A | 7/1997 | Cohen et al. | |
| 5,788,963 A | 8/1998 | Murphy et al. | |
| 5,831,016 A | 11/1998 | Wang et al. | |
| 5,843,448 A | 12/1998 | Chen et al. | |
| 5,843,633 A | 12/1998 | Yin et al. | |
| 5,844,075 A | 12/1998 | Kawakami et al. | |
| 5,846,538 A | 12/1998 | Cheever et al. | |
| 5,849,589 A | 12/1998 | Tedder et al. | |
| 5,851,756 A | 12/1998 | Steinman et al. | |
| 5,869,445 A | 2/1999 | Cheever et al. | |
| 5,876,712 A | 3/1999 | Cheever et al. | |
| 5,925,729 A | 7/1999 | Boon et al. | |
| 5,994,126 A | 11/1999 | Steinman et al. | |
| 6,010,905 A | 1/2000 | Cohen et al. | |
| 6,015,567 A | 1/2000 | Hudziak et al. | |
| 6,037,135 A | 3/2000 | Kubo et al. | |
| 6,077,519 A | 6/2000 | Storkus et al. | |
| 6,248,329 B1 | 6/2001 | Chanclrashekar et al. | |
| 6,300,090 B1 | 10/2001 | Steinman et al. | |
| 6,455,678 B1 | 9/2002 | Yin et al. | |
| 6,458,585 B1 | 10/2002 | Vachula et al. | |
| 6,479,286 B1 | 11/2002 | Nelson et al. | |
| 6,482,405 B1 | 11/2002 | Tahara et al. | |
| 6,514,942 B1 | 2/2003 | Ioannides et al. | |
| 6,537,560 B1 | 3/2003 | Kawakami et al. | |
| 6,566,395 B1 | 5/2003 | Moran | |
| 6,632,459 B2 | 10/2003 | Graus et al. | |
| 6,984,522 B2 | 1/2006 | Clarke et al. | |
| 7,115,360 B2 | 10/2006 | Clarke et al. | |
| 7,186,409 B2 | 3/2007 | Snyder et al. | |
| 7,204,982 B2 | 4/2007 | Liau | |
| 7,247,480 B2 | 7/2007 | Waldmann et al. | |
| 7,311,916 B2 | 12/2007 | Wild et al. | |

(Continued)

FOREIGN PATENT DOCUMENTS

| | | |
|---|---|---|
| CA | 2500715 | 4/2015 |
| EP | 2956164 | 12/2015 |

(Continued)

OTHER PUBLICATIONS

Chianese-Bullock et al. (J. Immunother. 2008; 31: 420-430).*

(Continued)

*Primary Examiner* — Stephen L Rawlings

(74) *Attorney, Agent, or Firm* — Fish & Richardson P.C.

(57) ABSTRACT

Compositions of multipeptide vaccines comprising at least seven tumor associated antigens, compositions of antigen presenting cell (e.g., dendritic cell) based vaccines presenting epitopes from at least seven tumor associated antigens, and methods of making same, are provided herein. Also, disclosed are methods for treating gynecological and peritoneal cancers using such vaccines.

18 Claims, 12 Drawing Sheets

Specification includes a Sequence Listing.

(56) References Cited

U.S. PATENT DOCUMENTS

| | | |
|---|---|---|
| 7,338,929 B2 | 3/2008 | Debinski et al. |
| 7,368,531 B2 | 5/2008 | Rosen et al. |
| 7,402,314 B2 | 7/2008 | Sherman et al. |
| 7,504,490 B1 | 3/2009 | Weinstock et al. |
| 7,842,466 B1 | 11/2010 | Kim et al. |
| 8,097,256 B2 | 1/2012 | Yu et al. |
| 8,129,184 B2 | 3/2012 | Yu |
| 8,168,586 B1 | 5/2012 | Fang et al. |
| 8,383,768 B2 | 2/2013 | Sing et al. |
| 8,604,167 B2 | 12/2013 | Sing et al. |
| 8,871,211 B2 | 10/2014 | Yu et al. |
| 9,023,338 B2 | 5/2015 | Yu |
| 9,068,020 B2 | 6/2015 | Yu et al. |
| 9,095,538 B2 | 8/2015 | Yu et al. |
| 9,382,308 B2 | 7/2016 | Yu et al. |
| 9,433,667 B2 | 9/2016 | Yu et al. |
| 2002/0034819 A1 | 3/2002 | Smith et al. |
| 2002/0045261 A1 | 4/2002 | Snyder et al. |
| 2002/0076707 A1 | 6/2002 | Mack et al. |
| 2002/0115213 A1 | 8/2002 | Snyder et al. |
| 2002/0119121 A1 | 8/2002 | Vitiello et al. |
| 2002/0182194 A1 | 12/2002 | Ju et al. |
| 2002/0192211 A1 | 12/2002 | Hudziak et al. |
| 2003/0064916 A1 | 4/2003 | Sherman |
| 2003/0095955 A1 | 5/2003 | Noessner et al. |
| 2003/0096298 A1 | 5/2003 | Barnea et al. |
| 2003/0185823 A1 | 10/2003 | Lum et al. |
| 2003/0190682 A1 | 10/2003 | Law et al. |
| 2003/0202963 A1 | 10/2003 | Crystal et al. |
| 2003/0204052 A1 | 10/2003 | Herrmann et al. |
| 2003/0204071 A1 | 10/2003 | Moore et al. |
| 2004/0031072 A1 | 2/2004 | La Rosa |
| 2004/0057935 A1 | 3/2004 | Yu et al. |
| 2004/0072246 A1 | 4/2004 | Martin et al. |
| 2004/0121946 A9 | 6/2004 | Fikes et al. |
| 2004/0197903 A1 | 10/2004 | Pestano |
| 2004/0203143 A1 | 10/2004 | Tjoa et al. |
| 2004/0210035 A1 | 10/2004 | Straten et al. |
| 2005/0059151 A1 | 3/2005 | Bosch |
| 2005/0119198 A1 | 6/2005 | Carmeliet et al. |
| 2005/0169897 A1 | 8/2005 | Snyder et al. |
| 2006/0003323 A1 | 1/2006 | Alsobrook et al. |
| 2006/0008468 A1 | 1/2006 | Chiang et al. |
| 2006/0204509 A1 | 9/2006 | Harty et al. |
| 2007/0020297 A1 | 1/2007 | Wheeler et al. |
| 2007/0098776 A1 | 5/2007 | Fikes et al. |
| 2007/0167375 A1 | 7/2007 | Okada et al. |
| 2008/0076904 A1 | 3/2008 | Cheever et al. |
| 2008/0107668 A1 | 5/2008 | Philip et al. |
| 2008/0131448 A1 | 6/2008 | Debinski et al. |
| 2008/0166374 A1 | 7/2008 | Debinski et al. |
| 2008/0199484 A1 | 8/2008 | Yu et al. |
| 2008/0206286 A1 | 8/2008 | Yu |
| 2008/0311141 A1 | 12/2008 | Yu et al. |
| 2008/0311142 A1 | 12/2008 | Yu et al. |
| 2009/0093052 A1 | 4/2009 | Yin et al. |
| 2009/0110702 A1 | 4/2009 | Wu et al. |
| 2009/0305418 A1 | 12/2009 | Moriarty et al. |
| 2010/0040637 A1 | 2/2010 | Van Orden et al. |
| 2010/0135975 A1 | 6/2010 | Yu et al. |
| 2010/0310643 A1 | 12/2010 | Singh et al. |
| 2012/0021043 A1 | 1/2012 | Kramps et al. |
| 2012/0052080 A1 | 3/2012 | Okada et al. |
| 2012/0156232 A1 | 6/2012 | Yu et al. |
| 2012/0189664 A1 | 7/2012 | Yu |
| 2012/0231030 A1 | 9/2012 | Demuazi et al. |
| 2013/0028915 A1 | 1/2013 | Palucka et al. |
| 2013/0115279 A1 | 5/2013 | Singh et al. |
| 2013/0183328 A1 | 7/2013 | Yu et al. |
| 2013/0183378 A1 | 7/2013 | Yu et al. |
| 2014/0234350 A1 | 8/2014 | Yu et al. |
| 2014/0234351 A1 | 8/2014 | Yu et al. |
| 2015/0359867 A1 | 12/2015 | Yu et al. |
| 2017/0173130 A1 | 6/2017 | Yu et al. |

FOREIGN PATENT DOCUMENTS

| | | |
|---|---|---|
| EP | 2956544 | 12/2015 |
| EP | 2328923 | 1/2016 |
| EP | 2427485 | 12/2016 |
| WO | WO 1989/006692 | 7/1989 |
| WO | WO 1992/020356 | 11/1992 |
| WO | WO 1994/026293 | 11/1994 |
| WO | WO 1995/021862 | 8/1995 |
| WO | WO 1996/018409 | 6/1996 |
| WO | WO 2000/024778 | 5/2000 |
| WO | WO 2000/038730 | 7/2000 |
| WO | WO 2000/066713 | 11/2000 |
| WO | WO 2001/008636 | 2/2001 |
| WO | WO 2001/041741 | 6/2001 |
| WO | WO 2001/058479 | 8/2001 |
| WO | WO 2001/068148 | 9/2001 |
| WO | WO 2002/029038 | 4/2002 |
| WO | WO 2002/068474 | 9/2002 |
| WO | WO 2003/010301 | 2/2003 |
| WO | WO 2003/014335 | 2/2003 |
| WO | WO 2003/035004 | 5/2003 |
| WO | WO 2003/066097 | 8/2003 |
| WO | WO 2003/092717 | 11/2003 |
| WO | WO 2003/102155 | 12/2003 |
| WO | WO 2005/028505 | 3/2005 |
| WO | WO 2005/037995 | 4/2005 |
| WO | WO 2005/043155 | 5/2005 |
| WO | WO 2005/079581 | 9/2005 |
| WO | WO 2006/034334 | 3/2006 |
| WO | WO 2007/062138 | 5/2007 |
| WO | WO 2008/039874 | 4/2008 |
| WO | WO 2008/039969 | 4/2008 |
| WO | WO 2008/039974 | 4/2008 |
| WO | WO 2008/052740 | 5/2008 |
| WO | WO 2008/054716 | 5/2008 |
| WO | WO 2008/066749 | 6/2008 |
| WO | WO 2008/083949 | 7/2008 |
| WO | WO 2010/028066 | 3/2010 |
| WO | WO 2010/129895 | 11/2010 |
| WO | WO 2012/079000 | 6/2012 |
| WO | WO 2014/127276 | 8/2014 |
| WO | WO 2014/127296 | 8/2014 |

OTHER PUBLICATIONS

Pilla et al. (Expert Opin. Biol. Ther. Aug. 2009; 9 (8): 1043-55).*

Abdel-Wahab et al., "Human dendritic cells, pulsed with either melanoma tumor cell lysates or the gp100 peptide(280-288), induce pairs of T-cell cultures with similar phenotype and lytic activity," Cell Immunol., 186(1):63-74, May 1998.

Ahmed et al., "HER2-Specific T Cells Target Primary Glioblastoma Stem Cells and Induce Regression of Autologous Experimental Tumors," Clin. Cancer Res., 16(2):474-485, Jan. 2010.

Akasaki et al., "Antitumor effect of immunizations with fusions of dendritic and glioma cells in a mouse brain tumor model," J. Immunother., 24(2):106-113, Mar. 2001.

Akasaki et al., "Dendritic cell-based immunotherapy for malignant gliomas," Expert Rev. Neurother., 5(4):497-508, Jul. 2005.

Akasaki et al., "Induction of a CD4+ T regulatory type 1 response by cyclooxygenase-2-overexpressing glioma," J. Immunol., 173(7):4352-4359, Oct. 2004.

Akasaki et al., "T cell immunity in patients with malignant glioma: recent progress in dendritic cell-based immunotherapeutic approaches," Front Biosci., 10:2908-2921, Sep. 2005.

Al-Hajj et al., "Prospective identification of tumorigenic breast cancer cells," Proc. Natl. Acad. Sci. USA, 100(7):3983-3988, Apr. 2003.

Altaner, "Glioblastoma and stem cells," Neoplasma 55(5):369-374, 2008.

Anderson et al., "Poor correspondence between predicted and experimental binding of peptides to class I MHC molecules," Tissue Antigens, 55(6):519-531, Jun. 2000.

Beier et al., "CD133+ and CD133– glioblastoma-derived cancer stem cells show differential growth characteristics and molecular profiles," Cancer Res., 67(9):4010-4015, May 2007.

(56) References Cited

OTHER PUBLICATIONS

Bjerkvig et al., "Opinion: the origin of the cancer stem cell: current controversies and new insights," Nat. Rev. Cancer., 5(11):899-904, Nov. 2005.
Boman et al., "Cancer stem cells: a step toward the cure," J. Clin. Oncol. ,26(17):2795-2799, Jun. 2008.
Borbulevych et al., "Increased immunogenicity of an anchor-modified tumor-associated antigen is due to the enhanced stability of the peptide/MHC complex: implications for vaccine design," J. Immunol., 174(8):4812-4820, Apr. 2005.
Borràs et al., "Findings on T cell specificity revealed by synthetic combinatorial libraries," J. Immunol Meth., 267(1):79-97, Sep. 2002.
Bossi et al., "Examining the presentation of tumor-associated antigens on peptide-pulsed T2 cells," Oncoimmunology, 2(11):e26840, Nov. 2013.
Bowie et al., "Deciphering the Message in Protein Sequences: Tolerance to Amino Acid Substitutions," Science, 247(4948):1306-1310, Mar. 1990.
Bowles et al., "Long-term remission of malignant brain tumors after intracranial infection: a report of four cases," Neurosurgery 44(3):636-642, Mar. 1999.
Bozzacco et al., "Mass spectrometry analysis and quantitation of peptides presented on the MHCII molecules of mouse spleen dendritic cells," J. Proteome Res., 10(11):5016-5030, Nov. 2011.
Brown et al., "Recognition and killing of brain tumor stem-like initiating cells by CD8+ cytolytic T cells," Cancer Res., 69(23):8886-8893, Dec. 2009.
Bullock et al., "Antigen density presented by dendritic cells in vivo differentially affects the number and avidity of primary, memory, and recall CD8+ T cells," J. Immunol., 170(4):1822-1829, Feb. 2003.
Cale et al., "Mutations in a dominant Nef epitope of simian immunodeficiency virus diminish TCR epitope peptide affinity but not epitope peptide:MHC class InBinding," J. Immunol., 187(6):3300-13, Sep. 2011.
Candido et al., "Local administration of dendritic cells inhibits established breast tumor growth: implications for apoptosis-inducing agents," Cancer Res., 61(1):228-236, Jan. 2001.
Carpentier et al., "Immune influence on adult neural stem cell regulation and function," Neuron., 64(1):79-92, Oct. 2009.
Casey et al., "Heat shock protein derived from a non-autologous tumour can be used as an anti-tumour vaccine," Immunol., 110(1):105-111, Sep. 2003.
Castelli et al., "Novel HLA-Cw8-restricted T cell epitopes derived from tyrosinase-related protein-2 and gp100 melanoma antigens," J. Immunol., 162(3):1739-1748, Feb. 1999.
Castro et al., "Current and future strategies for the treatment of malignant brain tumors," Pharmacol. Ther., 98(1):71-108, Apr. 2003.
Chandler et al., "Long-term survival in patients with glioblastoma multiforme," Neurosurgery, 32(5):716-720, May 1993.
Chang and Pastan, "Molecular cloning of mesothelin, a differentiation antigen present on mesothelium, mesotheliomas, and ovarian cancers," Proc. Natl. Acad. Sci. USA, 93(1):136-140, Jan. 1996.
Chang et al., "The ER aminopeptidase, ERAP1, trims precursors to lengths of MHC class I peptides by a 'molecular ruler' mechanism," Proc. Natl. Acad. Sci. USA., 102(47):17107-17112, Nov. 2005.
Chen et al., "Critical role of endoplasmic reticulum aminopeptidase 1 determining the length and sequence of peptides bound and presented by HLA-B27," Arthritis Rheumatol., 66(2):284-294, Feb. 2014.
Chen et al., "Identification of the MAGE-1 gene product by monoclonal and polyclonal antibodies," Proc. Natl. Acad. Sci. USA., 91(3):1004-1008, Feb. 1994.
Chianese-Bullock et al., "A multipeptide vaccine is safe and elicits T-cell responses in participants with advanced stage ovarian cancer," J. Immunother., 31(4):420-430, May 2008.
Chiang et al., "Adjuvants for enhancing the immunogenicity of whole tumor cell vaccines," Int. Rev. Immunol , 30(2-3):150-182, Apr.-Jun. 2011.
Chiang et al., "Optimizing parameters for clinical-scale production of high IL-12 secreting dendritic cells pulsed with oxidized whole tumor cell lysate," J. Transl. Med., 9:198, pp. 1-16, Nov. 2011.
Cho et al., "Recent advances of dendritic cells (DCs)-based immunotherapy for malignant gliomas," Cell Transplant., 18(9):977-983, 2009.
Curran et al., "Recursive partitioning analysis of prognostic factors in three radiation therapy oncology group malignant glioma trials," J. Nat. Cancer Inst., 85(9):704-710, May 1993.
Czerniecki et al., "Targeting HER-2/neu in early breast cancer development using dendritic cells with staged interleukin-12 burst secretion," Cancer Res., 67:1842-1852, Feb. 2007.
Debinsky, "Correspondence re: B. H. Joshi et al., interluekin-13 receptor α chain: a novel tumor-associated transmembrane protein in primary explants of human malignant gliomas. Cancer Res., 60: 1168-1172, 2000," Cancer Res. 61(14):5660-5662, Jul. 2001.
Del Monte "Does the cell No. 10(9) still really fit one gram of tumor tissue?" Cell Cycle., 8(3):505-506, Feb. 2009.
Delamarre et al., "Differential lysosomal proteolysis in antigen-presenting cells determines antigen fate," Science, 307(5715):1630-1634, Mar. 2005.
Dietz, "Engineering dendritic cell grafts for clinical trials in cellular immunotherapy of cancer: example of chronic myelogenous leukemia," Croatian Med. J., 42(4):428-435, Aug. 2001.
Drukker et al., "Characterization of the expression of MHC proteins in human embryonic stem cells," Proc. Natl. Acad. Sci. USA, 99(15):9864-9869, Jul. 2002.
Ehtesham et al., "Intratumoral dendritic cell vaccination elicits potent tumoricidal immunity against malignant glioma in rats," J. Immunother., 26(2):107-116, Mar.-Apr. 2003.
Ehtesham et al., "Recent progress in immunotherapy for malignant glioma: treatment strategies and results from clinical trials," Cancer Control., 11(3):192-207, May-Jun. 2004.
Falk et al., "Allele-specific motifs revealed by sequencing of self-peptides eluted from MHC molecules," J. Immunol., 177(5): 2741-2747, Sep. 2006.
Feltkamp et al., "Efficient MHC class I-peptide binding is required but does not ensure MHC class I-restricted immunogenicity," Mol. lmmunol., 31(18):1391-1401, Dec. 1994.
Feng et al., "P55, an immunogenic but nonprotective 55-kilodalton Borrelia burgdorferi protein in murine lyme disease," Infect. Immun., 64(1):363-365, Jan. 1996.
Friedman et al., "Temozolomide and treatment of malignant glioma," Clin. Cancer Res., 6(7):2585-2597, Jul. 2000.
Galli et al., "Isolation and characterization of tumorigenic, stem-like neural precursors from human glioblastoma," Cancer Res., 64(19):7011-7021, Oct. 2004.
Gao et al., Chapter 16, "Immunotherapy With CTL Restricted by Nonself MHC," Adoptive Immunotherapy, 2005 Edition, 2005, Humana Press Inc., pp. 216-217.
Garcia-Hernandez et al., "Prostate stem cell antigen vaccination induces a long-term protective immune response against prostate cancer in the absence of autoimmunity," Cancer Res., 68(3):861-869, Feb. 2008.
Gascoigne et al., "Co-receptors and recognition of self at the immunological synapse," Curr. Top. Microbiol. Immunol., 340:171-189, 2010.
Gatza et al., "Tumor cell lysate-pulsed dendritic cells are more effective than TCR Id protein vaccines for active immunotherapy of T cell lymphoma," J. Immunol., 169(9):5227-5235, Nov. 2002.
Gearhart, "New potential for human embryonic stem cells," Science, 282(5391):1061-1062, Nov. 1998.
Geiger et al., "Vaccination of pediatric solid tumor patients with tumor lysate-pulsed dendritic cells can expand specific T cells and mediate tumor regression," Cancer Res., 61(23):8513-8519, Dec. 2001.
Geschwind et al., "A genetic analysis of neural progenitor differentiation," Neuron., 29(2):325-39, Feb. 2001.

(56) References Cited

OTHER PUBLICATIONS

Ghods et al., "Spheres isolated from 9L gliosarcoma rat cell line possess chemoresistant and aggressive cancer stem-like cells," Stem Cells, 25(7):1645-1653, Jul. 2007.
Gilboa et al., "Immunotherapy of cancer with dendritic-cell-based vaccines," Cancer Immunol. Immunother., 46(2):82-87, Apr. 1998.
Guichard et al. "Melanoma peptide MART-1(27-35) analogues with enhanced binding capacity to the human class I histocompatibility molecule HLA-A2 by introduction of a β-amino acid residue: implications for recognition by tumor-infiltrating lymphocytes," J. Med. Chem., 43(20):3803-3808, Oct. 2000.
Haas et al., "Cycloxygenase-2 inhibition augments the efficacy of a cancer vaccine," Clin. Cancer Res., 12(1):214-222, Jan. 2006.
Hahn et al., "Short-term dietary administration of celecoxib enhances the efficacy of tumor lysate-pulsed dendritic cell vaccines in treating murine breast cancer," Int. J. Cancer, 118(9):2220-2231, May 2006.
Harada et al., "Melanoma-reactive CD8+ T cells recognize a novel tumor antigen expressed in a wide variety of tumor types," J. Immunother., 24(4):323-333, Jul.-Aug. 2001.
Harding et al., "Quantitation of antigen presenting cell MHC class II/peptide complexes necessary for T-cell stimulation," Nature, 346(6284):574-576, Aug. 1990.
Harizi et al., "Prostaglandin E2 modulates dendritic cell function via EP2 and EP4 receptor subytpes," J. Leukoc. Biol., 73(6):756-763, Jun. 2003.
Hassan et al., "Accurate quantitation of MHC-bound peptides by application of isotopically labeled peptide MHC complexes," J. Proteomics, 109:240-244, Sep. 2014.
Hatano et al., "EphA2 as a glioma-associated antigen: a novel target for glioma vaccines," Neoplasia, 7(8): 717-722, Aug. 2005.
Haynes et al., "Molecular characterization of the B' regulatory subunit gene family of *Arabidopsis* protein phosphatase 2A," Euro. J. Biochem., 260(1):127-136, Feb. 1999.
Heimberger et al., "Bone marrow-derived dendritic cells pulsed with tumor homogenate induce immunity against syngeneic intracerebral glioma," J Neuroimmunol., 103(1):16-24, Feb. 2000.
Hellstrom et al., "Overexpression of HER-2 in Ovarian Carcinomas," Cancer Res., 61(6):2420-2423, Mar. 2001.
Hemmati et al., "Cancerous stem cells can arise from pediatric brain tumors," Proc. Natl. Acad. Sci. USA, 100(25):15178-15183, Dec. 2003.
Hemmer et al., "Contribution of individual amino acids within MHC molecule or antigenic peptide to TCR ligand potency," J. Immunol., 164(2):861-871, Jan. 2000.
Hirschmann-Jax et al., "A distinct 'side population' of cells with high drug efflux capacity in human tumor cells," Proc. Natl. Acad. Sci. USA, 101(39):14228-14233, Sep. 2004.
Hori et al., "Neural progenitor cells lack immunogenicity and resist destruction as allografts," Stem Cells, 21(4):405-416, 2003.
Inoue et al., "Dendritic cells coinjected with tumor cells treated with an anticancer drug to induce tumor rejection," Surg. Today, 33(4):269-276, 2003.
Irvin et al., "T cells enhance stem-like properties and conditional malignancy in gliomas," PLoS One 5(6):e10974, Jun. 2010.
Jager et al., "Simultaneous humoral and cellular immune response against cancer-testis antigen NY-ESO-1: definition of human histocompatibility leukocyte antigen (HLA)-A2-binding peptide epitopes," J. Exp. Med., 187(2):267-270, Jan. 1998.
Ji et al., "Glioma stem cell research for the development of immunotherapy," Neurosurg. Clin. N. Am., 21(1):159-166, Jan. 2010.
Ji et al., "Identification of novel human leukocyte antigen-A0201-restricted, cytotoxic T lymphocyte epitopes on CD133 for cancer stem cell immunotherapy," Stem Cells Transl. Med., 3(3):356-364, Mar. 2014.
Joffre et al., "Cross-presentation by dendritic cells," Nat. Rev. Immunol., 12(8):557-569, Jul. 2012.
Joshi et al., "Interleukin-13 receptor α chain: a novel tumor-associated transmembrane protein in primary explants of human malignant gliomas," Cancer Res., 60:1168-1172, Mar. 2000.

Kalinski et al., "Prostaglandin E2 induces the final maturation of IL-12 deficient CD1a+CD83+ dendritic cells: the levels of IL-12 are determined during the final dendritic cell maturation and are resistant to further modulation," J. Immunol., 161(6):2804-2809, Sep. 1998.
Kelly et al., "Mesothelin-targeted agents in clinical trials and in preclinical development," Mol. Cancer Ther., 11(3):517-525, Mar. 2012.
Khong and Rosenberg, "Pre-existing immunity to tyrosinase-related protein (TRP)-2, a new TRP-2 isoform, and the NY-ESO-1 melanoma antigen in a patient with a dramatic response to immunotherapy," J. Immunol., 168(2):951-956, Jan. 2002.
Kikuchi et al., "Intratumoral injection of dendritic and irradiated glioma cells induces anti-tumor effects in a mouse brain tumor model," Cancer Immunol. Immunother., 51(8):424-430, Oct. 2002.
Kikuchi et al., "Results of a phase I clinical trial of vaccination of glioma patients with fusions of dendritic and glioma cells," Cancer Immunol. Immunother., 50(7):337-344, Sep. 2002.
Kim et al., "Folate binding protein peptide 191-199 presented on dendritic cells can stimulate CTL from ovarian and breast cancer patients," Anticancer Res., 19(48):2097-2916, Jul.-Aug. 1999.
Kimchi-Sarfaty et al., "A "silent" polymorphism in the MDR1 gene changes substrate specificity," Science, 315(5811):525-528, Jan. 2007.
Kioi et al., "Interleukin-13 receptor α2 chain: a potential biomarker and molecular target for ovarian cancer therapy," Cancer, 107(6):1407-1418, Sep. 2006.
Knutson et al., "Technology evaluation: DCVax, Northwest Biotherapeutics," Curr. Opin. Mol. Ther., 4(4):403-407, Aug. 2002.
Koch et al., "Immune-privileged embryonic, Swiss mouse STO and STO cell-derived progenitor cells: major histocompatibility complex and cell differentiation antigen expression patterns resemble those of human embryonic stem cell lines," Immunology, 119(1):98-115, Sep. 2006.
Koido et al., "Assessment of fusion cells from patient-derived ovarian carcinoma cells and dendritic cells as a vaccine for clinical use," Gynecol. Oncol., 99(2):462-471, Nov. 2005.
Kuby et al., Immunology, W. H. Freeman and Co., 523-524, 1992.
La Rosa et al., "Enhanced immune activity of cytotoxic T-lymphocyte epitope analogs derived from positional scanning synthetic combinatorial libraries," Blood, 97(6):1776-1786, Mar. 2001.
Landen et al., "EphA2 as a target for ovarian cancer therapy," Expert Opin. Ther. Targets, 9(6):1179-1187, Dec. 2005.
Lee et al., "Isolation of neural stem cells from the postnatal cerebellum," Nat. Neurosci., 8(6):723-729, Jun. 2005.
Lefranc, "Editorial: on the road to multi-modal and pluri-disciplinary treatment of glioblastomas," Acta. Neurochir. (Wien), 151(2):109-112, Feb. 2009.
Lemmel et al., "Differential quantitative analysis of MHC ligands by mass spectrometry using stable isotope labeling," Nat. Biotechnol., 22(4):450-454, Apr. 2004.
Li et al., "Human embryonic stem cells possess immune-privileged properties," Stem Cells, 22(4):448-456, 2004.
Liau et al., "Treatment of intracranial gliomas with bone marrow-derived dendritic cells pulsed with tumor antigens," J. Neurosurg., 90(6):1115-1124, Jun. 1999.
Liu and Yu, "Cancer vaccines: a novel strategy to sensitize malignant glioma to chemotherapy," Expert Rev. Neurother., 7(10):1235-1237, Oct. 2007.
Liu et al., "AIM-2: a novel tumor antigen is expressed and presented by human glioma cells," J. Immunother., 27(3):220-226, May-Jun. 2004.
Liu et al., "Analysis of gene expression and chemoresistance of CD133+ cancer stem cells in glioblastoma," Mol. Cancer, 5:67, Dec. 2006.
Liu et al., "Cell-mediated immunotherapy: a new approach to the treatment of malignant glioma," Cancer Control, 10(2):138-147, Mar.-Apr. 2003.
Liu et al., "Chemoresistance of stem-like cells isolated from glioblastoma," Proc. Amer. Assoc. Cancer Res, 47:75, abstract #320, 2006.

(56) References Cited

OTHER PUBLICATIONS

Liu et al., "Cytotoxic T cell targeting of TRP-2 sensitizes human malignant glioma to chemotherapy," Oncogene, 24(33):5226-5234, Aug. 2005.
Liu et al., "HER-2, gp100, and MAGE-1 are expressed in human glioblastoma and recognized by cytotoxic T cells," Cancer Res., 64(14):4980-4986, Jul. 2004.
Liu et al., "Molecular and functional analysis of tyrosinase-related protein (TRP)-2 as a cytotoxic T lymphocyte target in patients with malignant glioma," J. Immunother., 26(4):301-312, Jul.-Aug. 2003.
Liu et al., "Sensitization of malignant glioma to chemotherapy through dendritic cell vaccination," Expert Rev. Vaccines, 5(2):233-247, Apr. 2006.
Liu et al., "Small interference RNA modulation of IL-10 in human monocyte-derived dendritic cells enhances the Th1 response," Eur. J. Immunol., 34(6):1680-87, Jun. 2004.
Lupetti et al., "Translation of a retained intron in tyrosinase-related protein (TRP) 2 mRNA generates a new cytotoxic T lymphocyte (CTL)-defined and shared human melanoma antigen not expressed in normal cells of the melanocytic lineage," J. Exp. Med., 188(6):1005-1016, Sep. 1998.
Luptmwan et al., "Dendritic cell immunotherapy for malignant gliomas," Rev. Recent Clin. Trials, 3(1):10-21, Mar. 2008.
Lustgarten et al., "Identification of cross-reactive peptides using combinatorial libraries circumvents tolerance against Her-2/neu-immunodominant epitope," J. Immunol 176(3):1796-1805, Feb. 2006.
Lynch et al., "Flt3 ligand induces tumor regression and antitumor immune responses in vivo," Nat. Med., 3(6):625-631, Jun. 1997.
Maitland and Collins, "Prostate cancer stem cells: a new target for therapy," J. Clin. Oncol., 26(17):2862-2870, Jun. 2008.
Malarkannan et al., "Alloreactive CDB+ T Cells Can Recognize Unusual, Rare, and Unique Processed Peptide/MHC Complexes," J. Immunol.,157(10):4464-4473, Nov. 1996.
Mammolenti et al., "Absence of major histocompatibility complex class I on neural stem cells does not permit natural killer cell killing and prevents recognition by alloreactive cytotoxic T lymphocytes in vitro," Stem Cells, 22(6):1101-1110, 2004.
McKee et al., "How do adjuvants work? Important considerations for new generation adjuvants," Immunity, 27(5):687-690, Nov. 2007.
Mehta-Damani et al., "Generation of antigen-specific CD4+ T cell lines from naïve precursors," Eur. J. Immunol., 25(5):1206-1211, May 1995.
Mehta-Damani et al., "Generation of antigen-specific CD8+ CTLs from naive precursors," J. Immunol., 153(3):996-1003, Aug. 1994.
Meiring et al., "Mass tag-assisted identification of naturally processed HLA class II-presented meningococcal peptides recognized by CD4 + T lymphocytes," J. Immunol., 174(9):5636-5643, May 2005.
Melcher et al., "Dendritic cells for the immunotherapy of cancer," Clin. Oncol., 14(3):185-192, Jun. 2002.
Merrick et al., "Autologous versus allogeneic peptide-pulsed dendritic cells for anti-tumour vaccination: expression of allogeneic MHC supports activation of antigen specific T cells, but impairs early naïve cytotoxic printing and anti-tumour therapy," Cancer Immunol. Immunother., 57(6):897-906, Jun. 2008.
Mi et al., "Induced apoptosis supports spread of adenovirus vectors in tumors," Hum. Gene Ther., 12(10):1343-1352, Jul. 2001.
Miyabayashi et al., "Abstract 5165: Cancer stem cells express specific immunogenic proteins that induce TH17-dominant immunity resulting in regression of parental tumor in vivo," Cancer Res., 70(8 Suppl) 5165, Apr. 2010.
Mizrak et al., "CD133: molecule of the moment," J. Pathol., 214(1):3-9, Jan. 2008.
NCBI GenBank Accession No. NM_006017 (Jul. 13, 2008), 5 pages.
Neefjes et al., "Towards a systems understanding of MHC class I and MHC class II antigen presentation," Nat. Rev. Immunol., 11(12):823-836, Dec. 2011.
Neuzil et al., "Tumour-initiating cells vs. cancer 'stem' cells and CD133: what's in the name?" Biochem. Biophys. Res. Commun., 355(4):855-859, Apr. 2007.
Ngo et al., "Computational complexity, protein structure prediction and the Levinthal paradox," in Merz K.M., Le Grand S.M. (eds) The Protein Folding Problem and Tertiary Structure Prediction, Birkhauser Boston: Boston, MA, pp. 492-495.
Nielsen et al., "Reliable prediction of T-cell epitopes using neural networks with novel sequence representations," Protein Sci., 12(5):1007-1017, May 2003.
Nowak et al., "Synergy between chemotherapy and immunotherapy in the treatment of established murine solid tumors," Cancer Res., 63(15):4490-4496, Aug. 2003.
O'Brien et al., "A human colon cancer cell capable of initiating tumour growth in immunodeficient mice," Nature, 445(7123):106-110, Jan. 2007.
Okada et al., "Autologous glioma cell vaccine admixed with interleukin-4 gene transfected fibroblasts in the treatment of recurrent glioblastoma: preliminary observations in a patient with a favorable response to therapy," J. Neurooncol., 64(1-2):13-20, Aug.-Sep. 2003.
Okada et al., "Bone marrow-derived dendritic cells pulsed with a tumor-specific peptide elicit effective anti-tumor immunity against intracranial neoplasms," Int. J. Cancer, 78(2):196-201, Oct. 1998.
Okada et al., "Induction of CD8+ T-cell responses against novel glioma-associated antigen peptides and clinical activity by vaccinations with α-Type 1 polarized dendritic cells and polyinosinic-polycytidylic acid stabilized by lysine and carboxymethylcellulose in patients with recurrent malignant glioma," J. Clin. Oncol., 29(3):330-336, Jan. 2011.
Okano et al. "Identification of a novel HLA-A *0201-restricted, cytotoxic T lymphocyte epitope in a human glioma-associated antigen, interleukin 13 receptor α2 chain," Clin. Cancer Res., 8(9):2851-2855, Sep. 2002.
Ordonez et al., "Value of mesothelin immunostaining in the diagnosis of mesothelioma," Mod. Pathol., 16(3):192-197, Mar. 2003.
Osada et al., "Dendritic cells activate antitumor immunity for malignant intracranial germ cell tumor: a case report," Jpn J. Clin. Oncol., 31(8):403-406, Aug. 2001.
Parkhurst et al., "Identification of a shared HLA-A*0201-restricted T-cell epitope from the melanoma antigen tyrosinase-related protein 2 (TRP2)," Cancer Res., 58(21):4895-4901, Nov. 1998.
Parkhurst et al., "Improved induction of melanoma-reactive CTL with peptides from the melanoma antigen gp100 modified at HLA-A*0201-binding residues," J. Immunol., 157(6):2539-2548, Sep. 1996.
Parmiani et al., "Cancer immunotherapy with peptide-based vaccines: What have we achieved? Where are we going?," J. Natl. Cancer Inst., 94(11):805-818, Jun. 2002.
Parney et al., "Glioma immunology and immunotherapy," Neurosurgery, 46(4):778-791, Apr. 2000.
Pascolo et al., "A MAGE-A1 HLA-A*0201 epitope identified by mass spectrometry," Cancer Res., 61(10):4072-4077, May 2001.
Pellegatta et al., "Dendritic cell vaccines for cancer stem cells," Methods Mol. Biol., 568:233-247, 2009.
Pellegatta et al., "Neurospheres enriched in cancer stem-like cells are highly effective in eliciting a dendritic cell-mediated immune response against malignant gliomas," Cancer Res., 66(21):10247-November 10252, 2006.
Peoples et al., "Ovarian cancer-associated lymphocyte recognition of folate binding protein peptides," Ann. Surg. Oncol., 5(8):743-750, Dec. 1998.
Phuphanich et al., "Immune response correlation with progression-free survival in glioblastoma following dendritic cell immunotherapy (ICT-107)," J. Clin. Oncol., 28(15 suppl.):2097 (abstract), 2010.
Phuphanich et al., "Immune response correlation with progression-free survival in glioblastoma following dendritic cell immunotherapy (ICT-107)," poster presented at 2010 ASCO Annual Meeting, Jun. 4-8, 2010.
Phuphanich et al., "Phase I trial of a multi-epitope-pulsed dendritic cell vaccine for patients with newly diagnosed glioblastoma," Cancer Immunol. Immunother., 62(1):125-135, Jan. 2013.

(56) References Cited

OTHER PUBLICATIONS

Pinilla et al., "Investigation of antigen-antibody interactions using a soluble, non-support-bound synthetic decapeptide library composed of four trillion (4×1012) sequences," Biochem. J., 301(3):847-853, Aug. 1994.
Pinilla et al., "Rapid identification of high affinity peptide ligands using positional scanning synthetic peptide combinatorial libraries," Biotechniques, 13(6):901-905, Dec. 1992.
Pirtskhalaishvili et al., "Cytokine-mediated protection of human dendritic cells from prostate cancer induced apoptosis is regulated by the Bcl-2 family of proteins," Br. J. Cancer, 83:506-513, 2000.
Pisarra et al., "Human melanocytes and melanomas express novel mRNA isoforms of the tyrosinase-related protein-2/DOPAchrome tautomerase gene: molecular and functional characterization," J. Invest Dermatol., 115(1):48-56, Jul. 2000.
Pollack et al., "Exploitation of immune mechanisms in the treatment of central nervous system cancer," Semin. Pediatr. Neurol., 7(2):131-143, Jun. 2000.
Posnett et al., "A novel method for producing anti-peptide antibodies. Production of site-specific antibodies to the T cell antigen receptor beta-chain," J. Biol. Chem., 263(4):1719-1725, Feb. 1988.
Ramakrishna et al., "Naturally occurring peptides associated with HLA-A2 in ovarian cancer cell lines identified by mass spectrometry are targets of HLA-A2-restricted cytotoxic T cells," Int. Immunol , 15(6):751-763, Jun. 2003.
Reichardt et al., "Idiotype vaccination of multiple myeloma patients using monocyte-derived dendritic cells," Haematologica, 88(10):1139-1149, Oct. 2003.
Reya et al., "Stem cells, cancer, and cancer stem cells," Nature, 414(6859):105-111, Nov. 2001.
Reynolds and Weiss, "Generation of neurons and astrocytes from isolated cells of the adult mammalian central nervous system," Science, 255(5052):1707-1710, Mar. 1992.
Reynolds et al., "A multipotent EGF-responsive striatal embryonic progenitor cell produces neurons and astrocytes," J. Neurosci., 12(11):4565-4574, Nov. 1992.
Richardson et al., "CD133, a novel marker for human prostatic epithelial stem cells," J. Cell Sci., 117(Pt 16):3539-3545, Jul. 2004.
Rissoan et al., "Reciprocal control of T helper cell and dendritic cell differentiation," Science, 283(5405):1183-1186, Feb. 1999.
Rock and Goldberg, "Degradation of cell proteins and the generation of MHC class I-presented peptides," Ann. Rev. Immunol. 17(1):739-779, Apr. 1999.
Rosenberg et al., "Immunologic and therapeutic evaluation of a synthetic peptide vaccine for the treatment of patients with metastatic melanoma," Nat. Med., 4(3):321-327, Mar. 1998.
Rudinger, "Characteristics of the amino acids as components of a peptide hormone sequence," In: Parsons J.A. (eds) Peptide Hormones. Biological Council (The Co-ordinating Committee for Symposia on Drug Action). Palgrave, London, p. 107, 1976.
Salgaller et al., "Recognition of multiple epitopes in the human melanoma antigen gp100 by peripheral blood lymphocytes stimulated in vitro with synthetic peptides," Cancer Res., 55(21):4972-4979, Nov. 1995.
Sanai et al., "Neural stem cells and the origin of gliomas," N. Eng. J Med., 353(8):811-822, Aug. 2005.
Schirle et al., "Combining computer algorithms with experimental approaches permits the rapid and accurate identification of T cell epitopes from defined antigens," J. Immunol. Methods., 257(1):1-16, Nov. 2001.
Sette et al., "Epitope-based vaccines: an update on epitope identification, vaccine design and delivery," Curr. Opin. Immunol., 15(4):461-470, Aug. 2003.
Shin et al., "Antitumor effect of intratumoral administration of dendritic cell combination with vincristine chemotherapy in a murine fibrosarcoma model," Histol. Histopathol., 18(2):435-447, Apr. 2003.
Singh et al., "Cancer stem cells in nervous tumors," Oncogene 23(43):7267-7273, Sep. 2004.
Singh et al., "Identification of a cancer stem cell in human brain tumors," Cancer Res., 63(18):5821-5828, Sep. 2003.
Singh et al., "Identification of human brain tumor initiating cells," Nature, 432(7015):396-401, Nov. 2004.
Singh, "ImmunoCellular Therapeutics, Ltd." presentation at 13th Annual BIO CEO & Investor Conference, Feb. 14, 2011, 23 pages.
Smith et al., "CD133/prominin-1 is a potential therapeutic target for antibody-drug conjugates in hepatocellular and gastric cancers," Br. J. Cancer, 99(1):100-109, Jul. 2008.
Soling and Rainov, "Dendritic cell therapy of primary brain tumors," Mol. Med., 7(10):659-667, Oct. 2001.
Song et al., "Strategies to improve dendritic cell-based immunotherapy against cancer," Yonsei Med. J., 45(Suppl):48-52, 2004.
Steele et al., "The polycomb group proteins, BMI-1 and EZH2, are tumour-associated antigens," Br. J. Cancer, 95(9):1202-1211, Nov. 2006.
Steinbrink et al., "CD4+ and CD8+ anergic T cells induced by interleukin-10-treated human dendritic cells display antigen-specific suppressor activity," Blood, 99(7):2468-2476, Apr. 2002.
Steinman, "Some interfaces of dendritic cell biology," APMIS, 111(7-8):675-697, Jul.-Aug. 2003.
Storkus et al., "Identification of human melanoma peptides recognized by class I restricted tumor infiltrating T lymphocytes," J. Immunol., 151(7):3719-3727, Oct. 1993.
Stupp et al., "Recent Developments in the Management of Malignant Glioma," American Society of Clinical Oncology Educational Book 779-788, 2003.
Takagi et al., "Anti-tumor effects of dendritic and tumor cell fusions are not dependent on expression of MHC class I and II by dendritic cells," Cancer Lett., 213(1):49-55, Sep. 2004.
Tan et al., "Direct quantitation of MHC-bound peptide epitopes by selected reaction monitoring," Proteomics, 11(11):2336-2340, Jun. 2011.
Tanaka et al., "Intratumoral injection of dendritic cells after treatment of anticancer drugs induces tumor-specific antitumor effect in vivo," Int. J. Cancer, 101(3):265-269, Sep. 2002.
Tanaka et al., "Intratumoral injection of immature dendritic cells enhances antitumor effect of hyperthermia using magnetic nanoparticles," Int. J. Cancer 116(4):624-633, Sep. 2005.
Tian et al., "Expression of immunoglobulin superfamily cell adhesion molecules on murine embryonic stem cells," Biol. Reprod., 57(3):561-568, Sep. 1997.
Tong et al., "Combined intratumoral injection of bone marrow-derived dendritic cells and systemic chemotherapy to treat pre-existing murine tumors," Cancer Res., 61(2):7530-7535, Oct. 2001.
Tourdot et al., "A general strategy to enhance immunogenicity of low-affinity HLA-A2.1-associated peptides: implication in the identification of cryptic tumor epitopes," Eur. J. Immunol., 30:3411-3421, Dec. 2000.
Tunici et al., "Brain tumor stem cells: new targets for clinical treatments?," Neurosurg. Focus, 20(4):E27, Apr. 2006.
Tunici et al., "Genetic alterations and in vivo tumorigenicity of neurospheres derived from an adult glioblastoma," Mol. Cancer, 3:25, Oct. 2004.
Urban et al., "A subset of HLA-B27 molecules contains peptides much longer than nonamers," Proc. Natl. Acad. Sci. USA, 91(4):1534-1538, Feb. 1994.
Valmori et al., "Enhanced generation of specific tumor-reactive CTL in vitro by selected Melan-A/MART-1 immunodominant peptide analogues," J. Immunol., 160(4):1750-1758, Feb. 1998.
Van der Burg et al., "Immunogenicity of peptides bound to MHC class I molecules depends on the MHC-peptide complex stability," J. Immunol., 156(9):3308-3314, May 1996.
Van Els et al., "A single naturally processed measles virus peptide fully dominates the HLA-A *0201-associated peptide display and is mutated at its anchor position in persistent viral strains," Eur. J. Immunol., 30(4):1172-11781, Apr. 2000.
Voet and Voet, "Biochemistry," Section 6-3. Chemical Evolution, John Wiley and Sons, 1990, 126-128.
Wang et al., "A naturally processed peptide presented by HLA-A *0201 is expressed at low abundance and recognized by an alloreactive CD8+ cytotoxic T cell with apparent high affinity," J. Immunol., 158(12):5797-804, Jun. 1997.

(56) References Cited

OTHER PUBLICATIONS

Wang et al., "An effective cancer vaccine modality: lentiviral modification of dendritic cells expressing multiple cancer-specific antigens," Vaccine, 24(17):3477-3489, Apr. 2006.
Wang et al., "Identification of TRP-2 as a human tumor antigen recognized by cytotoxic T lymphocytes," J. Exp. Med., 184(6):2207-2216, Dec. 1996.
Wei et al., "Dendritic cells expressing a combined PADRE/MUC4-derived polyepitope DNA vaccine induce multiple cytotoxic T-cell responses," Cancer Biother. Radiopharm., 23(1):121-128, Feb. 2008.
Weigel et al., "Dendritic cells pulsed or fused with AML cellular antigen provide comparable in vivo antitumor protective responses," Exp. Hematol., 34(10):1403-1412, Oct. 2006.
Weigmann et al., "Prominin, a novel microvilli-specific polytopic membrane protein of the apical surface of epithelial cells, is targeted to plasmalemmal protrusions of non-epithelial cells," Proc. Natl. Acad. Sci. USA, 94(23):12425-12430, Nov. 1997.
Westphal et al., "Other experimental therapies for glioma," Recent Results Cancer Res., 171:155-164, 2009.
Wheeler et al., "Cellular immunity in the treatment of brain tumors," Clin. Neurosurg., 51:132-139, 2004.
Wheeler et al., "Clinical responsiveness of glioblastoma multiforme to chemotherapy after vaccination," Clin. Cancer Res., 10(16):5316-5326, Aug. 2004.
Wheeler et al., "Thymic CD8+ T cell production strongly influences tumor antigen recognition and age-dependent glioma mortality," J. Immunol., 171(9):4927-4933, Nov. 2003.
Wheeler et al., "Vaccination elicits correlated immune and clinical responses in glioblastoma multiforme patients," Cancer Res., 68(14):5955-5964, Jul. 2008.
Wu et al., "Embryonic stem cells and their differentiated derivatives have fragile immune privilege but still represent novel targets of immune attack," Stem Cells, 26(8):1939-1950, Aug. 2008.
Wu et al., "Expression of MHC I and NK ligands on human CD133+ glioma cells: possible targets of immunotherapy," J. Neurooncol., 83(2):121-131, Jun. 2007.
Wu et al., "Stimulation of ovarian tumor cell proliferation with monocyte products including interleukin-1, interleukin-6, and tumor necrosis factor-α," Am. J. Obstet. Gynecol., 166(3):997-1007, Mar. 1992.
Xu et al., "Antigen-specific T-cell response from dendritic cell vaccination using cancer stem-like cell-associated antigens," Stem Cells, 27(8):1734-1740, Aug. 2009.
Xu et al., "Hedgehog signaling regulates brain tumor-initiating cell proliferation and portends shorter survival for patients with PTEN-coexpressing glioblastomas," Stem Cells, 26(12):3018-3026, Dec. 2008.
Xu et al., "Isolation of tumour stem-like cells from benign tumours," Br. J. Cancer, 101(2):303-311, Jul. 2009.
Yakirevich et al., "Expression of the MAGE-A4 and NY-ESO-1 Cancer-Testis Antigens in Serous Ovarian Neoplasms," Clin. Cancer Res., 9(17):6453-6460, Dec. 2003.
Yamanaka et al, "Vaccination of recurrent glioma patients with tumour lysate-pulsed dendritic cells elicits immune response: results of a clinical phase I/II trial," Br. J. Cancer, 89(7):1172-1179, Oct. 2003.
Yamazaki et al., "Direct expansion of functional CD25+ CD4+ regulatory T cells by antigen-processing dendritic cells," J. Exp. Med., 198(2):235-247, Jul. 2003.
Yang et al., "Dendritic cells infected with a vaccinia vector carrying the human gp100 gene simultaneously present multiple specificities and elicit high-affinity T cells reactive to multiple epitopes and restricted by HLA-A2 and -A3," J. Immunol., 164(8):4204-4211, Apr. 2000.
Yang et al., "Modulation of major histocompatibility complex Class I molecules and major histocompatibility complex-bound immunogenic peptides induced by interferon-alpha and interferon-gamma treatment of human glioblastoma multiforme," J. Neurosurg., 100(2):310-319, Feb. 2004.

Yasuda et al., "Dendritic cell-tumor cell hybrids enhance the induction of cytotoxic T lymphocytes against murine colon cancer: a comparative analysis of antigen loading methods for the vaccination of immunotherapeutic dendritic cells," Oncol. Rep., 16(6):1317-1324, Dec. 2006.
Yewdell et al., "Making sense of mass destruction. quantitating MHC class I antigen presentation," Nat. Rev. Immunol., 3(12):952-961, Dec. 2003.
Yin et al., "AC133, a novel marker for human hematopoietic stem and progenitor cells," Blood, 90(12):5002-5012, Dec. 1997.
Yin et al., "Expression and regulation of major histocompatibility complex on neural stem cells and their lineages," Stem Cells Dev., 17(1):53-65, Feb. 2008.
Young and Steinman, "Dendritic cells stimulate primary human cytolytic lymphocyte responses in the absence of CD4+ helper T cells," J. Exp. Med., 171(4):1315-1332, Apr. 1990.
Yu et al. "CD133 as a Potential Target of Anti-Cancer Stem Cell Immunotherapy: Identification of an HLA-A*02 Restricted CD133 Epitope. Abstract," J. Immunother., 31(9):928, Nov.-Dec. 2008.
Yu et al. Abstract for the 2th Annual Scientific Meeting of the Society for Immunotherapy of Cancer (SITC). "Phase I Trial of a Multi-epitope Pulsed Dendritic Cell Vaccine Targeting Cancer Stem Cells in Patients With Newly Diagnosed Glioblastoma," J. Immunother., 35(9): 747 and 748, Nov.-Dec. 2012.
Yu et al., "AC133-2, a novel isoform of human AC133 stem cell antigen," J. Biol. Chem., 277(23):20711-20716, Jun. 2002.
Yu et al., "Effective combination of chemotherapy and dendritic cell administration for the treatment of advanced-stage experimental breast cancer," Clin. Cancer Res., 9(1):285-294, Jan. 2003.
Yu et al., "Mahaley Clinical Research Award: chemosensitization of glioma through dendritic cell vaccination," Clin. Neurosurg., 53:345-351, 2006.
Yu et al., "Vaccination of malignant glioma patients with peptide-pulsed dendritic cells elicits systemic cytotoxicity and intracranial T-cell infiltration," Cancer Res., 61(3):842-847, Feb. 2001.
Yu et al., "Vaccination with tumor lysate-pulsed dendritic cells elicits antigen-specific, cytotoxic T-cells in patients with malignant glioma," Cancer Res., 64(14):4973-4979, Jul. 2004.
Yuan et al., "Isolation of cancer stem cells from adult glioblastoma multiforme," Oncogene, 23(58):9392-9400, Dec. 2004.
Zabierowski and Herlyn, "Melanoma stem cells: the dark seed of melanoma," J. Clin. Oncol., 26(17):2890-2894, Jun. 2008.
Zagzag et al., "Downregulation of major histocompatibility complex antigens in invading glioma cells: stealth invasion of the brain," Lab Invest., 85(3):328-341, Mar. 2005.
Zeidler et al., "Tumor cell-derived prostaglandin E2 inhibits monocyte function by interfering with CCR5 and Mac-1," FASEB J., 14(5):661-668, Apr. 2000.
Zhang et al., "Antigenic profiling of glioma cells to generate allogeneic vaccines or dendritic cell-based therapeutics," Clin. Cancer Res., 13(2):566-575, Jan. 2007.
Zhang et al., "Expression of tumor-specific antigen MAGE, GAGE, and BAGE in ovarian cancer tissues and cell lines," BMC Cancer, 10:163, pp. 1-6, Apr. 2010.
Zhang et al., "Extensively cross-reactive anti-HIV-1 neutralizing antibodies induced by gp140 immunization," Proc. Natl. Acad. Sci. USA, 104(24):10193-10198, Jun. 2007.
Zhang et al., "Vaccination with embryonic stem cells generates effective antitumor immunity against ovarian cancer," Int. J. Mol. Med., 31(1):147-153, Jan. 2013.
Zhou et al., "The ABC transporter Berp1/ABCG2 is expressed in a wide variety of stem cells and is a molecular determinant of the side-population phenotype," Nat. Med., 7(9):1028-1034, Sep. 2001.
Zhu et al., "Insertion of the dibasic motif in the flanking region of a cryptic self-determinant leads to activation of the epitope-specific T cells," J. Immunol., 175(4):2252-2260, Aug. 2005.
Zitvogel et al., "Therapy of murine tumors with tumor peptide-pulsed dendritic cells: dependence on T cells, B7 costimulation, and T helper cell-1 associated cytokines," J. Exp. Med. 183:87-97, Jan. 1996.
Zou et al., "Cancer initiating cells or cancer stem cells in the gastrointestinal tract and liver," J. Cell Physiol., 217(3):598-604, Dec. 2008.

(56) References Cited

OTHER PUBLICATIONS

Canadian Office Action in Canadian Patent Application No. 2700436, dated Dec. 2, 2015, 3 pages.
Canadian Office Action in Canadian Patent Application No. 2700436, dated Feb. 3, 2015, 3 pages.
Canadian Office Action in Canadian Patent Application No. 2700436, dated Nov. 7, 2013, 5 pages.
Canadian Office Action in Canadian Patent Application No. 2700579, dated Nov. 6, 2013, 4 pages.
European Office Action in European Patent Application No. 09812172.6, dated Mar. 28, 2014, 4 pages.
European Office Action in European Patent Application No. 09812172.6, dated May 23, 2012, 5 pages.
European Office Action in European Patent Application No. 09812172.6, dated Nov. 6, 2013, 4 pages.
European Office Action in European Patent Application No. 10772898.2, dated Aug. 22, 2013, 6 pages.
European Office Action in European Patent Application No. 10772898.2, dated Dec. 19, 2014, 6 pages.
European Office Action in European Patent Application No. 10772898.2, dated Jun. 11, 2015, 6 pages.
European Office Action in European Patent Application no. 14751889.8, dated Feb. 19, 2018, 4 pages.
European Search Report in European Patent Application No. 07843269.7, dated Feb. 2, 2011, 9 pages.
European Search Report in European Patent Application No. 14751889.8, dated Aug. 1, 2016, 9 pages.
European Search Report in European Patent Application No. 14752122.3, dated Oct. 10, 2016, 4 pages.
International Preliminary Report on Patentability in Application No. PCT/US2007/079846, dated Apr. 9, 2009, 5 pages.
International Preliminary Report on Patentability in Application No. PCT/US2007/079857, dated Apr. 9, 2009, 5 pages.
International Preliminary Report on Patentability in Application No. PCT/US2009/055759, dated Mar. 8, 2011, 7 pages.
International Preliminary Report on Patentability in Application No. PCT/US2010/034082, dated Nov. 9, 2011, 4 pages.
International Preliminary Report on Patentability in Application No. PCT/US2014/016562, dated Aug. 18, 2015, 10 pages.
International Preliminary Report on Patentability in Application No. PCT/US2014/016610, dated Aug. 18, 2015, 10 pages.
International Search Report and Written Opinion in Application No. PCT/US2007/079600, dated Mar. 27, 2008, 10 pages.
International Search Report and Written Opinion in Application No. PCT/US2007/079846, dated Jul. 14, 2008, 10 pages.
International Search Report and Written Opinion in Application No. PCT/US2009/055759, dated Jun. 28, 2010, 12 pages.
International Search Report and Written Opinion in Application No. PCT/US2010/034082, dated Feb. 22, 2011, 9 pages.
International Search Report and Written Opinion in Application No. PCT/US2014/016562, dated Jun. 3, 2014, 37 pages.
International Search Report and Written Opinion in Application No. PCT/US2014/016610, dated Jun. 5, 2014, 24 pages.
International Search Report in Application No. PCT/US2007/079857, dated Apr. 8, 2008, 9 pages.
USPTO Office Action in U.S. Appl. No. 11/862,135, dated Jan. 6, 2010, 12 pages.
USPTO Office Action in U.S. Appl. No. 11/862,135, dated Jul. 23, 2010, 10 pages.
USPTO Office Action in U.S. Appl. No. 11/863,990, dated Aug. 26, 2010, 15 pages.
USPTO Office Action in U.S. Appl. No. 11/863,990, dated Feb. 6, 2014, 12 pages.
USPTO Office Action in U.S. Appl. No. 11/863,990, dated May 12, 2011, 18 pages.
USPTO Office Action in U.S. Appl. No. 11/864,177, dated Aug. 26, 2010, 16 pages.
USPTO Office Action in U.S. Appl. No. 11/864,177, dated May 13, 2011, 18 pages.
USPTO Office Action in U.S. Appl. No. 12/552,945, dated Aug. 16, 2012, 13 pages.
USPTO Office Action in U.S. Appl. No. 12/552,945, dated Jun. 5, 2014, 31 pages.
USPTO Office Action in U.S. Appl. No. 12/552,945, dated Mar. 12, 2012, 20 pages.
USPTO Office Action in U.S. Appl. No. 12/552,945, dated Oct. 22, 2014, 27 pages.
USPTO Office Action in U.S. Appl. No. 12/776,200, dated Apr. 18, 2012, 10 pages.
USPTO Office Action in U.S. Appl. No. 12/776,200, dated Aug. 7, 2012, 14 pages.
USPTO Office Action in U.S. Appl. No. 13/327,125, dated Aug. 20, 2014, 14 pages.
USPTO Office Action in U.S. Appl. No. 13/327,125, dated Jan. 12, 2015, 15 pages.
USPTO Office Action in U.S. Appl. No. 13/365,666, dated May 22, 2014, 18 pages.
USPTO Office Action in U.S. Appl. No. 13/365,666, dated Oct. 6, 2014, 14 pages.
USPTO Office Action in U.S. Appl. No. 13/826,737, dated Jun. 13, 2014, 37 pages.
USPTO Office Action in U.S. Appl. No. 13/826,737, dated May 11, 2015, 25 pages.
USPTO Office Action in U.S. Appl. No. 13/826,737, dated Oct. 24, 2014, 38 pages.
USPTO Office Action in U.S. Appl. No. 13/828,432, dated Dec. 1, 2014, 12 pages.
USPTO Office Action in U.S. Appl. No. 14/766,711, dated Dec. 26, 2017, 17 pages.
USPTO Office Action in U.S. Appl. No. 14/766,711, dated Jun. 2, 2017, 20 pages.
Supplementary European Search Report in European Patent Application No. 09812172.6, dated May 4, 2012, 6 pages.
Supplementary European Search Report in European Patent Application No. 10772898.2, dated Jun. 11, 2013, 4 pages.

\* cited by examiner

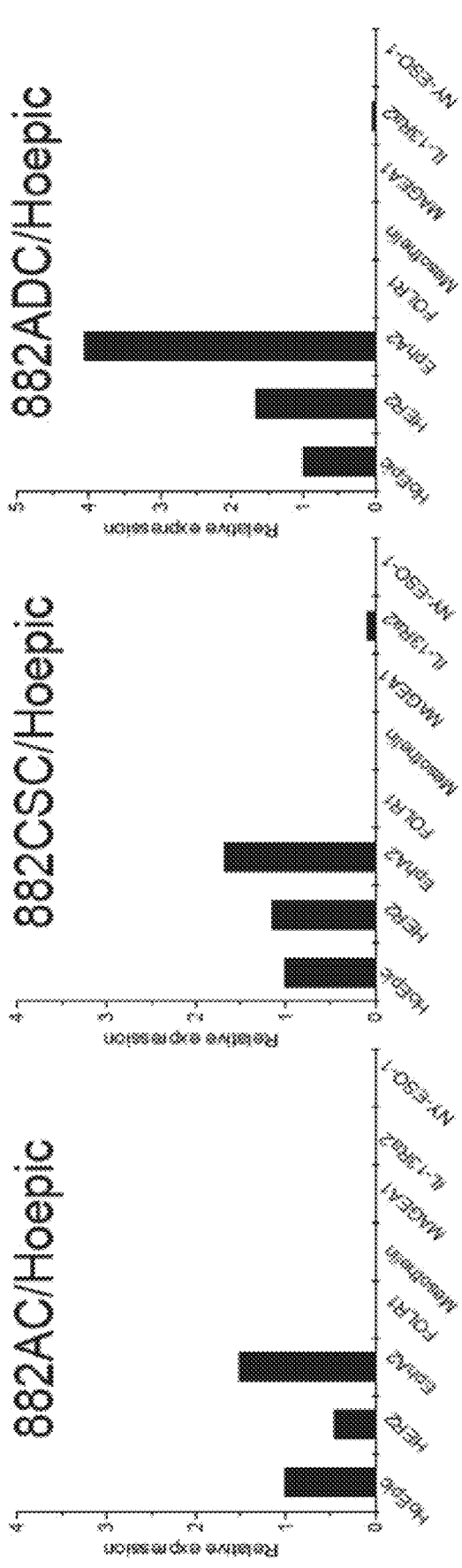

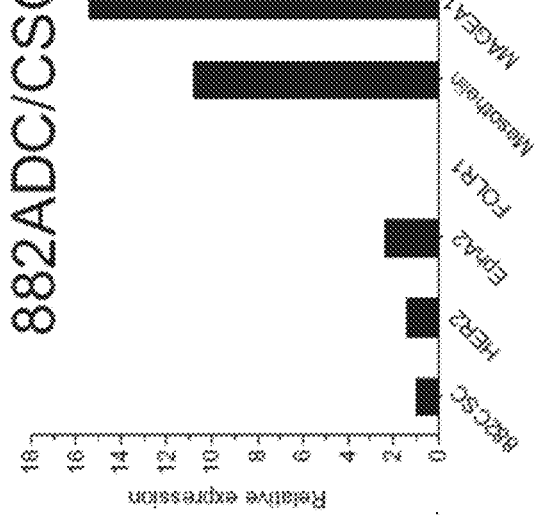
FIG. 2A  
FIG. 2B
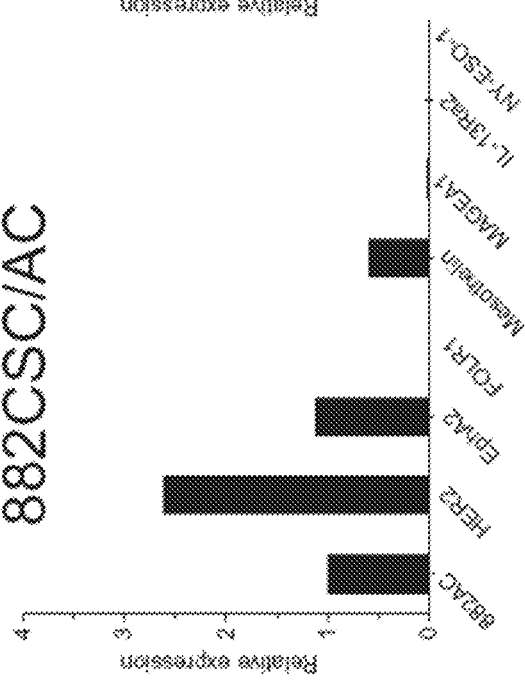
| | 882AC(Ct) | 882CSC(Ct) | 882ADC(Ct) | 882CSC/AC 2^ Δ(ΔCt) | 882ADC/CSC 2^ Δ(ΔCt) |
|---|---|---|---|---|---|
| GAPDH | 22.38 | 22.53 | 25.03 | | |
| HER2 | 29.01 | 27.77 | 29.74 | 2.62 | 1.45 |
| EphA2 | 26.96 | 26.94 | 28.18 | 1.122 | 2.39 |
| Mesothelin | 38.97 | 39.88 | 38.94 | 0.5913 | 10.85 |
| MageA1 | 33.43 | 39.42 | 37.97 | 0.0174 | 15.45 |
| FOLR1 | N/A | N/A | N/A | | |
| IL-13Ra2 | N/A | 36.36 | 39.97 | | 0.4655 |
| NYESO-1 | N/A | N/A | N/A | | |

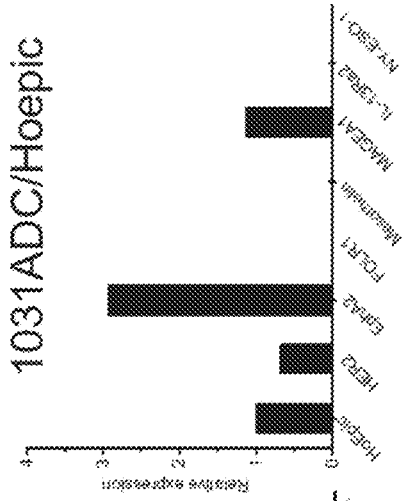
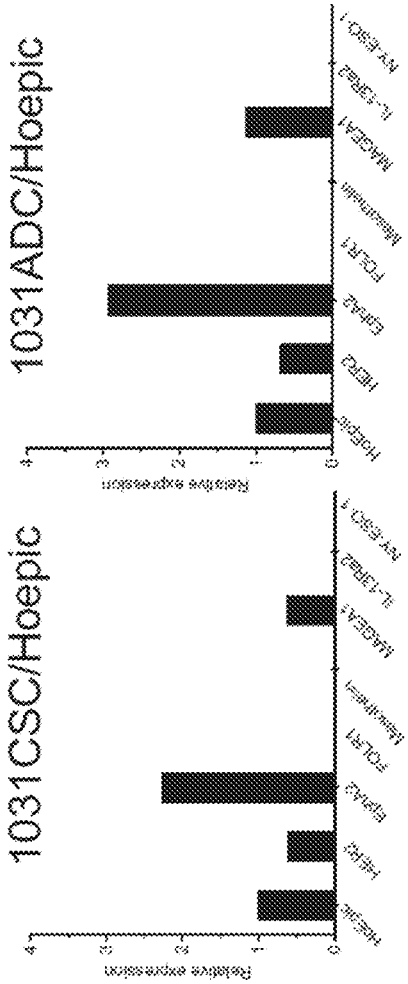
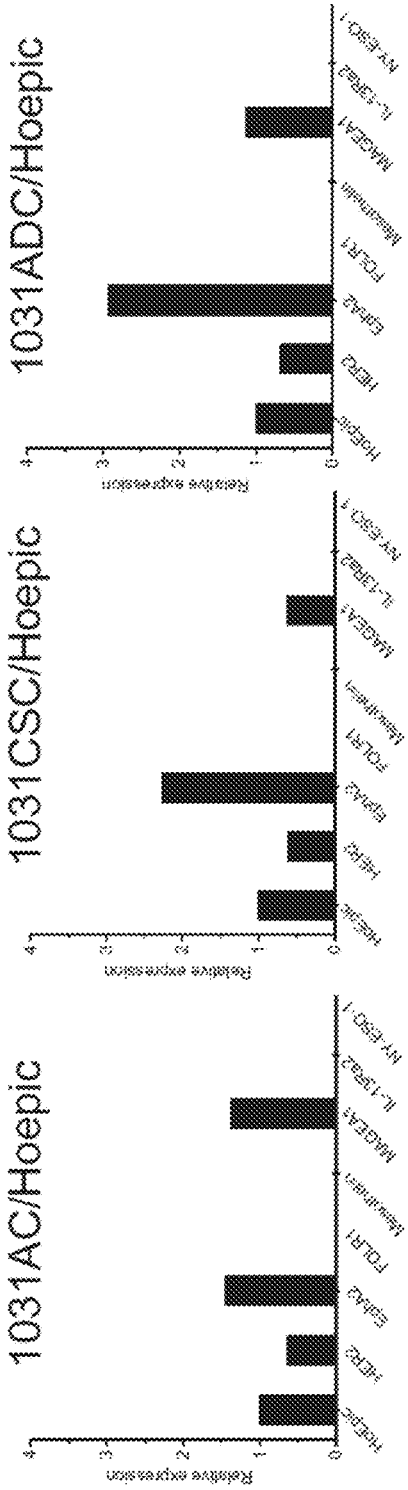
FIG. 3A 1031AC/Hoepic
FIG. 3B 1031CSC/Hoepic
FIG. 3C 1031ADC/Hoepic

| | 1031AC(Ct) | 1031CSC(Ct) | 1031ADC(Ct) | 1031CSC/AC 2^-Δ(ΔCt) | 1031ADC/CSC 2^-Δ(ΔCt) |
|---|---|---|---|---|---|
| GAPDH | 22.63 | 21.96 | 23.11 | | |
| HER2 | 29 | 28.43 | 29.42 | 0.94 | 1.11 |
| EphA2 | 27.04 | 25.75 | 26.52 | 1.54 | 1.3 |
| Mesothelin | 37.66 | 37.08 | 37.79 | 0.94 | 1.35 |
| MageA1 | 36.99 | 37.47 | 37.75 | 0.39 | 1.82 |
| FOLR1 | N/A | N/A | N/A | | |
| IL-13Ra2 | N/A | N/A | N/A | | |
| NYESO-1 | N/A | N/A | N/A | | |

| Peptides | MFI | SD | MFI index | SD |
|---|---|---|---|---|
| HER2p773 | 207.77 | 27.9 | 1.58 | 0.3503 |
| IL-13Ra2p345 | 303.67 | 35.22 | 2.78 | 0.4536 |
| EphA2p883 | 414.96 | 16.81 | 4.17 | 0.2082 |
| NY-ESO-1p157 | 275.8 | 14.16 | 2.44 | 0.1735 |
| FOLR1p191 | 96.84 | 8.49 | 0.2 | 0.109 |
| MAGEA1p278 | 270.02 | 36.85 | 2.36 | 0.4598 |
| Mesothelinp531 | 411.03 | 65.54 | 4.13 | 0.8239 |
| Mart1 | 386.32 | 98.68 | 3.82 | 1.234 |

| | MFI | SD |
|---|---|---|
| T2(UT) | 80.19 | 3.27 |

T2(UT): no peptide, untreated T2 cell

| Gene name | RNA(high)** | RNA(low)* | HR | Logrank P |
|---|---|---|---|---|
| HER2 | 320 | 237 | 1.35(1.06-1.71) | 0.013 |
| EphA2 | 297 | 260 | 1.35(1.07-1.7) | 0.011 |
| FOLR1 | 314 | 243 | 0.77(0.61-0.97) | 0.028 |
| MSLN | 367 | 190 | 1.3(1-1.68) | 0.046 |
| MAGEA1 | 178 | 379 | 1.38(1.08-1.76) | 0.0087 |
| IL-13Ra2 | 323 | 234 | 1.14(0.91-1.44) | 0.26 |
| NYESO-1 | 396 | 161 | 1.22(0.94-1.59) | 0.13 |
|  | RNA(high)**: RNA high expression | RNA(low)*: RNA low expression | HR: Hazard ratio |  |

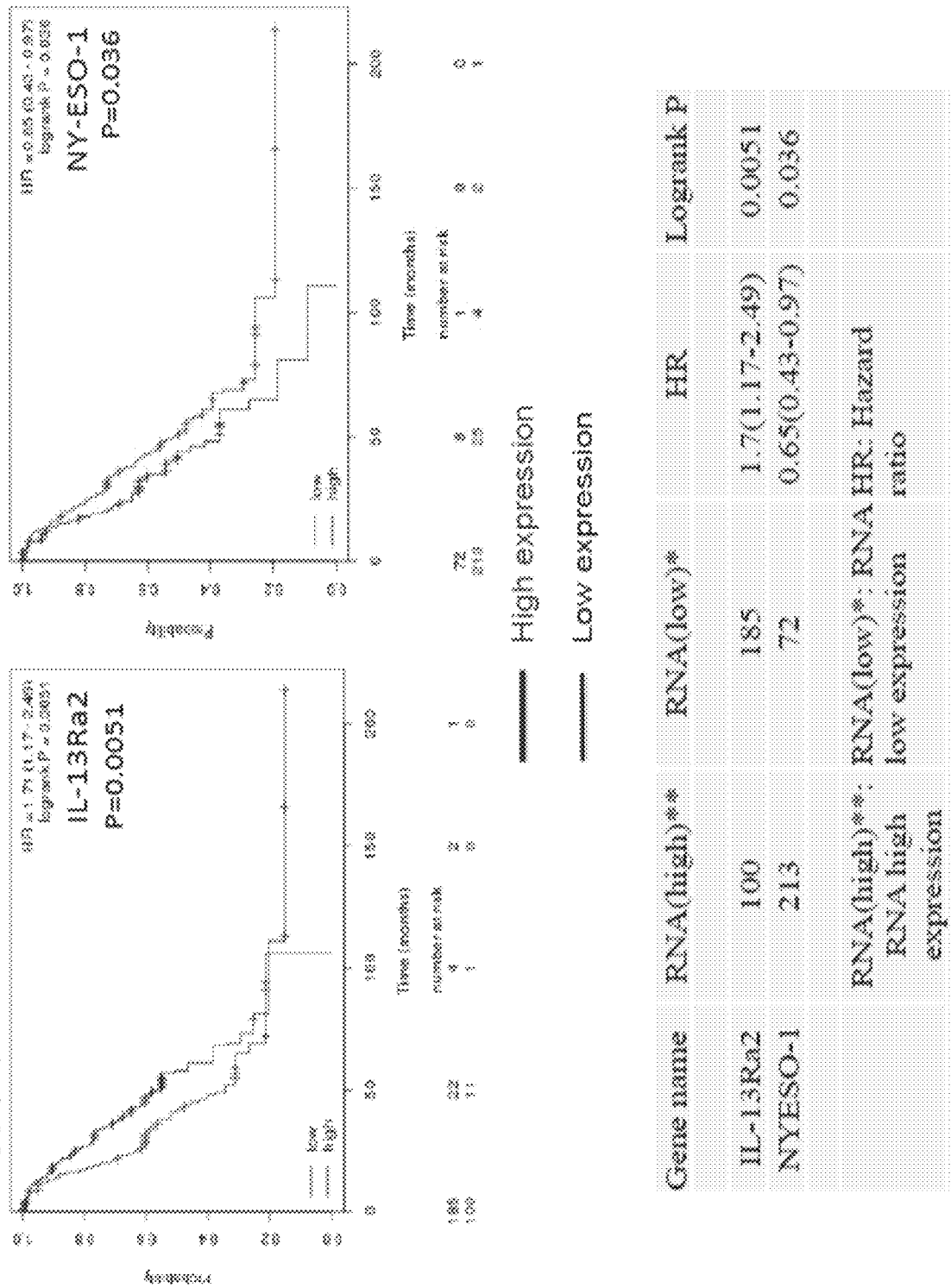

CANCER VACCINES AND VACCINATION METHODS

CROSS-REFERENCE TO RELATED APPLICATIONS

This application is a divisional application of and claims priority under 35 U.S.C. § 120 to U.S. application Ser. No. 14/766,685, filed on Aug. 7, 2015, now U.S. Pat. No. 10,137,182, which is a 371 of International Application No. PCT/US2014/016610, filed on Feb. 14, 2014, which claims priority to U.S. Provisional Patent Application No. 61/764,789, filed on Feb. 14, 2013. The entire contents of each application listed above is incorporated by reference herein.

TECHNICAL FIELD

The disclosure relates generally to multivalent vaccine compositions, methods of making such compositions, as well as methods for the treatment of gynecologic and peritoneal cancers.

BACKGROUND

Epithelial ovarian cancer (EOC) is the most frequent cause of gynecologic cancer-related mortality in women (Jemal, A., et al., Global cancer statistics. CA Cancer J Clin, 2011, 61(2): p. 69-90). It was estimated that in 2008 (the most recent year numbers are available), approximately 21,204 women were diagnosed and 14,362 women died of disease in the US (see, www.cdc.gov/cancer/ovarian/statistics/index.htm). It is estimated that approximately 190,000 new cases will be diagnosed and 115,000 women will die from ovarian cancer per year world-wide. While advances in chemotherapy have been made over the past three decades, the overall 5 year survival for advanced stage disease remains less than 35%.

Initial response rates of advanced ovarian cancer to the standard upfront paclitaxel and carboplatin treatment approach is 75%, with complete clinical response rates near 55%. Unfortunately over 75% of subjects with complete clinical response are destined to relapse and succumb to their disease (Coukos, G. and S. C. Rubin, Chemotherapy resistance in ovarian cancer: new molecular perspectives. Obstet Gynecol, 1998, 91(5 Pt 1): p. 783-92). For most subjects, ovarian cancer will recur within two years, with median time to progression of 20-24 months for optimally surgically cytoreduced subjects and 12-18 months for subjects with suboptimal reduction. Response rates to second line chemotherapy are significantly lower, between 15-30%, depending on the length of progression free survival and the number of previous treatments. Once ovarian cancer has recurred, it is not considered curable and progression to death is usually inevitable, despite aggressive chemotherapy strategies. These facts elucidate the enormous unmet need for the development of alternate therapies in ovarian cancer (Coukos, G. and S. C. Rubin, Gene therapy for ovarian cancer. Oncology (Williston Park), 2001, 15(9): p. 1197-204, 1207; discussion 1207-8; Coukos, G., et al., Immunotherapy for gynaecological malignancies. Expert Opin Biol Ther, 2005, 5(9): p. 1193-210; Coukos, G., M. C. Courreges, and F. Benencia, Intraperitoneal oncolytic and tumor vaccination therapy with replication-competent recombinant virus: the herpes paradigm. Curr Gene Ther, 2003, 3(2): p. 113-25).

Fallopian tube and primary peritoneal cancers have many molecular, histologic, clinical and etiologic similarities to epithelial ovarian carcinoma. More that 90% of fallopian tube cancers are serous adenocarcinomas, which are histologically indistinguishable from papillary serous ovarian carcinoma. Women, diagnosed with fallopian tube cancer and primary peritoneal cancer, are clinically treated using the same surgical and chemotherapeutic approach as epithelial ovarian cancer because of the similarities in their biological behavior (Benedet, J. L., et al., FIGO staging classifications and clinical practice guidelines in the management of gynecologic cancers. FIGO Committee on Gynecologic Oncology. Int J Gynaecol Obstet, 2000, 70(2): p. 209-62). Most of the hereditary and perhaps many of the sporadic ovarian cancers may in fact originate in the fallopian tube, further underlying similarities between the two tumors.

Immunotherapy is a form of cancer treatment that activates the immune system to attack and eradicate cancer cells. Cytotoxic T lymphocytes ("CTL") are critical to a successful antitumor immune response. T cells that attack cancer cells require the presentation of tumor antigens to naïve T cells that undergo activation, clonal expansion, and ultimately exert their cytolytic effector function. Effective antigen presentation is essential to successful CTL effector function. Thus, the development of a successful strategy to initiate presentation of tumor antigens to T cells can be important to an immunotherapeutic strategy for cancer treatment.

With the clinical outcome of many types of cancers being from poor to lethal, there exists a significant need for the development of novel therapeutic treatments.

SUMMARY

This disclosure is based, at least in part, on the recognition that immunizing gynecological and peritoneal cancer patients with antigen presenting cells (APC) loaded with combinations of MHC class I peptide epitopes from at least seven tumor antigens, or with multipeptide mixtures of these peptide epitopes, can induce surprisingly strong therapeutic immune responses that can lead to significantly improved responsiveness to treatment and increased patient survival. The seven tumor antigens are: mesothelin, NY-ESO-1, Folate Binding Protein, HER2/neu, IL-13Rα2, MAGE-A1, and EphA2.

The rationale for using one or more epitopes from these at least these seven antigens stems from the fact that these antigens are involved in a wide range of cellular functions such as tumor growth, tumor differentiation, transformation, signal transduction, cell adhesion, and cell movement. Thus, vaccines comprising peptide epitopes from these antigens will target multiple antigens that will attack different functions of the cancer cell (e.g., ovarian, fallopian, and peritoneal cancer cell). In addition, the use of the mixture of peptide epitopes from these seven antigens prevent the generation of escape mutants that would down regulate a single antigen. Furthermore, as the majority of the seven antigens are highly expressed in ovarian cancer as well as peritoneal and fallopian tube cancers, the combination of peptide epitopes of these seven antigens would provide coverage for all ovarian tumors as well as peritoneal and fallopian tube cancers. Finally, a vaccine comprising epitopes from these seven antigens will target antigens early in the disease that are normally upregulated with progression. Thus, it is believed that the specific combination of epitopes in Table 1 (i.e., SEQ ID NO:17, SEQ ID NO:26, SEQ ID NO:28, SEQ ID NO:40, SEQ ID NO:49, SEQ ID NO:55, and SEQ ID NO:66; or SEQ ID NO:15, SEQ ID NO:26, SEQ ID NO:28, SEQ ID NO:40, SEQ ID NO:49, SEQ ID NO:55, and SEQ ID NO:66) will be useful in treatment of ovarian cancer as well as peritoneal and fallopian tube cancers either as a multipeptide vaccine and/or as a dendritic cell vaccine.

Accordingly, compositions and methods for inducing immune responses in cancer patients against tumor antigens are provided herein. The compositions include multipeptide vaccines comprising HLA class I epitopes from at least the following seven tumor antigens: mesothelin, NY-ESO-1, Folate Binding Protein (FBP), Human Epidermal Growth Factor Receptor 2 (HER-2/neu), IL-13 receptor α2, Melanoma-associated antigen 1 (MAGE-A1), and EPH receptor A2 (EphA2). The compositions also include antigen presenting cells (e.g., dendritic cells) that present epitopes comprising HLA class I epitopes from the above-listed seven tumor associated antigens. The methods described herein use such vaccines for the treatment of gynecological cancer and peritoneal cancer.

In one aspect, the disclosure provides a composition comprising at least one major histocompatibility complex (MHC) class I peptide epitope of at least seven antigens selected from the group consisting of mesothelin, NY-ESO-1, FBP, HER-2/neu, IL-13 receptor α2, MAGE-A1, EphA2, p53, k-Ras, Ep-CAM, MUC1, Survivin, hTERT, and WT1. The epitopes of the at least seven antigens may be stored individually or stored as a mixture of these epitopes. In certain embodiments of this aspect, the composition can comprise a mixture of at least one major histocompatibility complex (MHC) class I peptide epitope of at least eight, nine, or ten antigens. In certain embodiments of this aspect, the MHC class I peptide epitope is an HLA-A2 epitope. In some embodiments, the composition can comprise a mixture of at least one MHC class I peptide epitope of the following seven antigens: Mesothelin, NY-ESO-1, FBP, HER-2/neu, IL-13 receptor α2, MAGE-A1, and EphA2. In some specific embodiments, the composition comprising at least one MHC class I peptide epitope of the seven antigens comprises the following peptide sequences: SLLFLLFSL (SEQ ID NO:15) or VLPLTVAEV (SEQ ID NO:17) from Mesothelin; SLLMWITQC (SEQ ID NO:26) from NY-ESO-1; EIWTHSYKV (SEQ ID NO:28) from FBP; VMAGVGSPYV (SEQ ID NO:40) from HER2/neu; WLPFGFILI (SEQ ID NO:49) from IL-13Rα2; KVLEYVIKV (SEQ ID NO:55) from MAGE-A1; and TLADFDPRV (SEQ ID NO:66) from EphA2. In certain embodiments, the peptides are synthetic.

In another embodiment, the composition of this aspect, further comprises at least one MHC class I peptide epitope from a tumor associated antigen, wherein the tumor associated antigen is not any of mesothelin, NY-ESO-1, FBP, HER-2/neu, IL-13 receptor α2, MAGE-A1, or EphA2. In some specific embodiments, the composition comprising at least one MHC class I peptide epitope of the seven antigens further comprises at least one MHC class I peptide epitope of at least one (e.g., 1, 2, 3, 4, 5, 6, or 7) of the following seven antigens: p53, k-Ras, Ep-CAM, MUC1, Survivin, hTERT, and WT1 (e.g., p53; k-Ras; Ep-CAM; MUC1; Survivin; hTERT; WT1; p53 and k-Ras; p53 and Ep-CAM; p53 and MUC1; p53 and Survivin; p53 and hTERT1; p53 and WT1; k-Ras and Ep-CAM; k-Ras and MUC1; k-Ras and Survivin; k-Ras and hTERT; k-Ras and WT1; Ep-CAM and MUC1; Ep-CAM and Survivin; Ep-CAM and hTERT; Ep-CAM and WT1; MUC1 and Survivin; MUC1 and hTERT; MUC1 and WT1; Survivin and hTERT; Survivin and WT1; hTERT and WT1; p53, k-Ras, and Ep-CAM; p53, Ep-CAM, and MUC1; p53, MUC-1, and Survivin; p53, Survivin, and hTERT; p53, hTERT1, and WT1; p53, WT1, and MUC-1; Survivin, hTERT, and WT1; Ep-CAM, Survivin, hTERT, and WT1; p53, Survivin, hTERT, and WT1; k-Ras, Survivin, hTERT, and WT1; Ep-CAM, k-Ras, Survivin, hTERT, and WT1; p53, k-Ras, Ep-CAM, MUC1, Survivin, and hTERT; -Ras, Ep-CAM, MUC1, Survivin, hTERT, and WT1; p53, k-Ras, Ep-CAM, MUC1, Survivin, hTERT, and WT1).

In some specific embodiments, the composition comprising at least one MHC class I peptide epitope of the seven antigens further comprises two MHC class I peptide epitopes of at least one (e.g., 1, 2, 3, 4, 5, 6, or 7) of the following seven antigens: p53, k-Ras, Ep-CAM, MUC1, Survivin, hTERT, and WT1 (e.g., p53; k-Ras; Ep-CAM; MUC1; Survivin; hTERT; WT1; p53 and k-Ras; p53 and Ep-CAM; p53 and MUC1; p53 and Survivin; p53 and hTERT1; p53 and WT1; k-Ras and Ep-CAM; k-Ras and MUC1; k-Ras and Survivin; k-Ras and hTERT; k-Ras and WT1; Ep-CAM and MUC1; Ep-CAM and Survivin; Ep-CAM and hTERT; Ep-CAM and WT1; MUC1 and Survivin; MUC1 and hTERT; MUC1 and WT1; Survivin and hTERT; Survivin and WT1; hTERT and WT1; p53, k-Ras, and Ep-CAM; p53, Ep-CAM, and MUC1; p53, MUC-1, and Survivin; p53, Survivin, and hTERT; p53, hTERT1, and WT1; p53, WT1, and MUC-1; Survivin, hTERT, and WT1; Ep-CAM, Survivin, hTERT, and WT1; p53, Survivin, hTERT, and WT1; k-Ras, Survivin, hTERT, and WT1; Ep-CAM, k-Ras, Survivin, hTERT, and WT1; p53, k-Ras, Ep-CAM, MUC1, Survivin, and hTERT; -Ras, Ep-CAM, MUC1, Survivin, hTERT, and WT1; p53, k-Ras, Ep-CAM, MUC1, Survivin, hTERT, and WT1).

In certain embodiments, the at least one MHC class I peptide is synthetic. In another embodiment, the composition of this aspect, further comprises at least one (e.g., 1, 2, 3) MHC class I peptide epitope from a tumor associated antigen, wherein the tumor associated antigen is not p53, k-Ras, Ep-CAM, MUC1, Survivin, or hTERT. In certain embodiments, the at least one MHC class I peptide is synthetic. In another embodiment, the composition of this aspect, further comprises at least one (e.g., 1, 2, 3) MHC class I peptide epitope from a tumor associated antigen, wherein the tumor associated antigen is not mesothelin, NY-ESO-1, FBP, HER-2/neu, IL-13 receptor α2, MAGE-A1, EphA2, p53, k-Ras, Ep-CAM, MUC1, Survivin, or hTERT.

In some embodiments, the composition of this aspect, further comprises at least one (e.g., 1, 2, 3, 4) MHC class II peptide epitope. In some embodiments, the composition of this aspect further comprises an adjuvant. In some embodiments, the composition of this aspect, further comprises a pharmaceutically acceptable carrier.

In another aspect, this disclosure features a composition comprising isolated peptides comprising the following amino acid sequences: SLLFLLFSL (SEQ ID NO:15) with two or fewer (e.g., 2, 1, or none) amino acid substitutions within SEQ ID NO:15, or VLPLTVAEV (SEQ ID NO:17) with two or fewer amino acid substitutions within SEQ ID NO:17; SLLMWITQC (SEQ ID NO:26) with two or fewer amino acid substitutions within SEQ ID NO:26; EIWTHSYKV (SEQ ID NO:28) with two or fewer amino acid substitutions within SEQ ID NO:28; VMAGVGSPYV (SEQ ID NO:40) with two or fewer amino acid substitutions within SEQ ID NO:40; WLPFGFILI (SEQ ID NO:49) with two or fewer amino acid substitutions within SEQ ID NO:49; KVLEYVIKV (SEQ ID NO:55) with two or fewer amino acid substitutions within SEQ ID NO:55; and TLADFDPRV (SEQ ID NO:66) with two or fewer amino acid substitutions within SEQ ID NO:66.

The epitopes of the at least seven antigens may be stored individually or stored as a mixture of these epitopes. In some specific embodiments, the composition further comprises at least one MHC class I peptide epitope of at least one (e.g., 1, 2, 3, 4, 5, 6, 7) of the following seven antigens: p53, k-Ras, Ep-CAM, MUC1, Survivin, hTERT, and WT1 (e.g., p53; k-Ras; Ep-CAM; MUC1; Survivin; hTERT; WT1; p53 and k-Ras; p53 and Ep-CAM; p53 and MUC1; p53 and Survivin; p53 and hTERT1; p53 and WT1; k-Ras and Ep-CAM; k-Ras and MUC1; k-Ras and Survivin; k-Ras and hTERT; k-Ras and WT1; Ep-CAM and MUC1; Ep-CAM and Survivin; Ep-CAM and hTERT; Ep-CAM and WT1; MUC1 and Survivin; MUC1 and hTERT; MUC1 and WT1; Survivin and hTERT; Survivin and WT1; hTERT and WT1; p53, k-Ras, and Ep-CAM; p53, Ep-CAM, and MUC1; p53, MUC-1, and Survivin; p53, Survivin, and hTERT; p53, hTERT1, and WT1; p53, WT1, and MUC-1; Survivin, hTERT, and WT1; Ep-CAM, Survivin, hTERT, and WT1; p53, Survivin, hTERT, and WT1; k-Ras, Survivin, hTERT, and WT1; Ep-CAM, k-Ras, Survivin, hTERT, and WT1; p53, k-Ras, Ep-CAM, MUC1, Survivin, and hTERT; -Ras, Ep-CAM, MUC1, Survivin, hTERT, and WT1; p53, k-Ras, Ep-CAM, MUC1, Survivin, hTERT, and WT1). In certain embodiments, the peptides are synthetic. In another embodiment, the composition further comprises at least one MHC class I peptide epitope from a tumor associated antigen, wherein the tumor associated antigen is not mesothelin, NY-ESO-1, FBP, HER-2/neu, IL-13 receptor α2, MAGE-A1, EphA2, p53, k-Ras, Ep-CAM, MUC1, Survivin, or hTERT. In some embodiments, the composition further comprises at least one MHC class II peptide epitope. In some embodiments, the composition further comprises an adjuvant. In some embodiments, the composition further comprises a pharmaceutically acceptable carrier.

In another aspect, this disclosure features a composition comprising isolated dendritic cells, wherein the dendritic cells present peptide sequences on their cell surface, wherein the peptide sequences comprise at least one (e.g., 1, 2, 3, 4, 5, 6, 7, 8, 9, 10) MHC class I peptide epitope of at least seven of the following antigens: Mesothelin, NY-ESO-1, FBP, HER-2/neu, IL-13 receptor α2, MAGE-A1, EphA2, p53, k-Ras, Ep-CAM, MUC1, Survivin, hTERT, and WT1 (e.g., Mesothelin, NY-ESO-1, FBP, HER-2/neu, IL-13 receptor α2, MAGE-A1, and EphA2; Mesothelin, NY-ESO-1, FBP, HER-2/neu, IL-13 receptor α2, MAGE-A1, EphA2, and survivin; Mesothelin, NY-ESO-1, FBP, HER-2/neu, IL-13 receptor αa2, MAGE-A1, EphA2, and hTERT; Mesothelin, NY-ESO-1, FBP, HER-2/neu, IL-13 receptor α2, MAGE-A1, EphA2, and WT1; Mesothelin, NY-ESO-1, FBP, HER-2/neu, IL-13 receptor α2, MAGE-A1, EphA2, and Ep-CAM; Mesothelin, NY-ESO-1, FBP, HER-2/neu, IL-13 receptor α2, MAGE-A1, EphA2, and MUC1; FBP, Her-2, NY-ESO-1, IL-13Rα2, Survivin, hTERT, and WT1). In some embodiments, the MHC class I peptide epitope is an HLA-A2 peptide epitope. In a specific embodiment, the MHC class I peptide epitope is an HLA-A0201 peptide epitope. In certain embodiments, the dendritic cells present peptide sequences comprising MHC class I peptide epitopes of at least, eight, nine, or ten of the antigens.

In certain embodiments, the MHC class I peptide epitopes comprise the following peptide sequences: SLLFLLFSL (SEQ ID NO:15) or VLPLTVAEV (SEQ ID NO:17) from Mesothelin; SLLMWITQC (SEQ ID NO:26) from NY-ESO-1; EIWTHSYKV (SEQ ID NO:28) from FBP; VMAGVGSPYV (SEQ ID NO:40) from HER2/neu; WLPFGFILI (SEQ ID NO:49) from IL-13Rα2; KVLEY-VIKV (SEQ ID NO:55) from MAGE-A1; and TLADFDPRV (SEQ ID NO:66) from EphA2. In some embodiments, the dendritic cells acquired the peptide epitopes in vitro by exposure to synthetic peptides comprising the peptide epitopes. In certain embodiments, the composition further comprises dendritic cells that present at least one MHC class I epitope of at least one of the following seven antigens: p53, k-Ras, Ep-CAM, MUC1, Survivin, hTERT, and WT1. In some embodiments, the composition further comprises at least one MHC class I epitope from a tumor associated antigen, wherein the tumor associated antigen is not mesothelin, NY-ESO-1, FBP, HER-2/neu, IL-13 receptor α2, MAGE-A1, EphA2, p53, k-Ras, Ep-CAM, MUC1, Survivin, hTERT, or WT1. In some embodiments, the peptide sequences are synthetic.

In another aspect, the disclosure features a solution comprising isolated dendritic cells presenting the following MHC class I peptide epitopes on their cell surface: SLL-FLLFSL (SEQ ID NO:15) or VLPLTVAEV (SEQ ID NO:17) from Mesothelin; SLLMWITQC (SEQ ID NO:26) from NY-ESO-1; EIWTHSYKV (SEQ ID NO:28) from FBP; VMAGVGSPYV (SEQ ID NO:40) from HER2/neu; WLPFGFILI (SEQ ID NO:49) from IL-13Rα2; KVLEY-VIKV (SEQ ID NO:55) from MAGE-A1; and TLADFDPRV (SEQ ID NO:66) from EphA2. In certain embodiments this solution also includes one or more of: Plasmalyte-A (20-40%—e.g., 20%, 25%, 30%, 35%, 40%), dextrose (1-8% e.g., 1%, 2%, 3%, 4%, 5%, 6%, 7%, 8%)/NaCl (0.2 to 0.6M—e.g., 0.2, 0.3, 0.4, 0.5, 0.6), DMSO (5 to 10% e.g., 5%, 6%, 7%, 8%, 9%, 10%), dextran (0.2% to 2%—e.g., 0.2%, 0.4%, 0.5%, 0.6%, 0.7%, 0.8%, 0.9%, 1%, 1.2%, 1.5%, 2%) and human serum albumin (1% to 7.5%—e.g., 1%, 2%, 3%, 4%, 4.5%, 5%, 5.5%, 6%, 6.5%, 7%, 7.5%). In a specific embodiment, the solution comprises 31.25% Plasmalyte-A; 31.25% dextrose (5%)/0.45 M NaCl; 7.5% DMSO; 1% dextran; and 5% human serum albumin. In some embodiments, the solution contains $1 \times 10^7$ to $1.5 \times 10^7$ dendritic cells. In some embodiments, the solution has a volume of 1 mL.

In yet another aspect, the disclosure features a method of treating a gynecological or peritoneal cancer. The method involves administering to a subject in need thereof an effective amount of a composition described herein. In certain embodiments, the gynecological cancer is epithelial ovarian cancer or fallopian tube cancer. In some embodiments, the peritoneal cancer is primary peritoneal cancer. In some embodiments, the method further involves administering a second agent prior to, at substantially the same time as, or subsequent to, administering the subject with the composition, wherein the second agent is any agent that is useful in the treatment of the gynecological or peritoneal cancer. Combination therapy may allow lower doses of multiple agents and/or modified dosing regimens, thus reducing the overall incidence of adverse effects. In some embodiments, the method further involves administering a chemotherapeutic agent prior to, at substantially the same time as, or subsequent to, administering the subject with the composition. In certain embodiments, the subject is administered the chemotherapeutic agent 0.5 hours to 3 days (0.5 hours, 1 hour, 2 hours, 3 hours, 4 hours, 5 hours, 6 hours, 8 hours, 10 hours, 12 hours, 14 hours, 15 hours, 18 hours, 20 hours, 1 day, 1.5 days, 2 days, 2.5 days, 3 days) prior to or subsequent to administering the subject with the composition. In a specific embodiment, the chemotherapeutic agent is cyclophosphamide. In other embodiments, the chemotherapeutic agent is paclitaxel, altretamine, capecitabine, etoposide, gemcitabine, ifosfamide, irinotecan, doxorubicin, melphalan, pemetrexed, toptecan, or vinorelbine.

In another aspect, the disclosure features a process that includes the steps of: obtaining bone marrow derived mononuclear cells from a patient; culturing the mononuclear cells in vitro under conditions in which mononuclear cells become adherent to a culture vessel; selecting adherent mononuclear cells; culturing the adherent mononuclear cells in the presence of one or more cytokines under conditions in which the cells differentiate into antigen presenting cells; and culturing the antigen presenting cells in the presence of peptides, wherein the peptides comprise amino acid sequences corresponding to at least one MHC class I peptide epitope of at least seven of the following sixteen antigens: Mesothelin, NY-ESO-1, FBP, HER-2/neu, IL-13 receptor α2, MAGE-A1 EphA2, p53, k-Ras, Ep-CAM, MUC1, Survivin, hTERT, and WT1, under conditions in which the cells present the peptides on major histocompatibility class I molecules.

In some embodiments, the synthetic peptides comprise at least one MHC class I peptide epitope of the following antigens: Mesothelin, NY-ESO-1, FBP, HER-2/neu, IL-13 receptor α2, MAGE-A1 and EphA2. In certain embodiments, the one or more cytokines comprise granulocyte macrophage colony stimulating factor and interleukin-4 (IL-4). In other embodiments, the one or more cytokines comprise tumor necrosis factor-α (TNF-α). In certain embodiments, the bone marrow derived cells are obtained from a patient diagnosed with epithelial ovarian cancer, primary peritoneal cancer, or fallopian tube carcinoma. In a specific embodiment, the synthetic peptides comprise the following sequences: SLLFLLFSL (SEQ ID NO:15) or VLPLTVAEV (SEQ ID NO:17) from Mesothelin; SLLMWITQC (SEQ ID NO:26) from NY-ESO-1; EIWTHSYKV (SEQ ID NO:28) from FBP; VMAGVGSPYV (SEQ ID NO:40) from HER2/neu; WLPFGFILI (SEQ ID NO:49) from IL-13Rα2; KVLEYVIKV (SEQ ID NO:55) from MAGE-A1; and TLADFDPRV (SEQ ID NO:66) from EphA2.

"Gynecological cancer" means cervical, ovarian, uterine, vaginal, vulvar, or fallopian tube cancer.

By "ovarian cancer" is meant a cancerous growth arising from the ovaries. The term encompasses epithelial ovarian tumors, germ cell ovarian tumors, sex cord stromal ovarian tumors as well as metastatic cancers that spread to the ovaries.

"Epitope" means a short peptide derived from a protein antigen, wherein the peptide binds to a major histocompatibility complex (MHC) molecule and is recognized in the MHC-bound context by a T cell. The epitope may bind an MHC class I molecule (e.g., HLA-A1, HLA-A2 or HLA-A3) or an MHC class II molecule.

"Treatment" and "treating," as used herein refer to both therapeutic treatment and prophylactic or preventative measures, wherein the object is to inhibit or slow down (lessen) the targeted disorder (e.g., cancer, e.g., ovarian cancer) or symptom of the disorder, or to improve a symptom, even if the treatment is partial or ultimately unsuccessful. Those in need of treatment include those already diagnosed with the disorder as well as those prone or predisposed to contract the disorder or those in whom the disorder is to be prevented. For example, in tumor (e.g., cancer) treatment, a therapeutic agent can directly decrease the pathology of tumor cells, or render the tumor cells more susceptible to treatment by other therapeutic agents or by the subject's own immune system.

A "dendritic cell" or "DC" is an antigen presenting cell (APC) that typically expresses high levels of MHC molecules and co-stimulatory molecules, and lacks expression of (or has low expression of) markers specific for granulocytes, NK cells, B lymphocytes, and T lymphocytes, but can vary depending on the source of the dendritic cell. DCs are able to initiate antigen specific primary T lymphocyte responses in vitro and in vivo, and direct a strong mixed leukocyte reaction (MLR) compared to peripheral blood leukocytes, splenocytes, B cells and monocytes. Generally, DCs ingest antigen by phagocytosis or pinocytosis, degrade it, present fragments of the antigen at their surface and secrete cytokines.

Unless defined otherwise, technical and scientific terms used herein have the same meaning as commonly understood by one of ordinary skill in the art to which this disclosure belongs. Singleton et al., Dictionary of Microbiology and Molecular Biology 3rd ed., J. Wiley & Sons (New York, N.Y. 2001); March, Advanced Organic Chemistry Reactions, Mechanisms and Structure 5th ed., J. Wiley & Sons (New York, N.Y. 2001); Sambrook and Russel, Molecular Cloning: A Laboratory Manual 3rd ed., Cold Spring Harbor Laboratory Press (Cold Spring Harbor, N.Y. 2001); and Lutz et al., Handbook of Dendritic Cells: Biology, Diseases and Therapies, J. Wiley & Sons (New York, N.Y. 2006), provide one skilled in the art with a general guide to many of the terms used in the present application. Although methods and materials similar or equivalent to those described herein can be used in the practice or testing of the present invention, suitable methods and materials are described below. All publications, patent applications, patents, and other references mentioned herein are incorporated herein by reference in their entirety. In case of conflict, the present specification, including definitions, will control. In addition, the materials, methods, and examples are illustrative only and not intended to be limiting.

Other features and advantages of the invention will be apparent from the following detailed description, the drawings, and from the claims.

BRIEF DESCRIPTION OF THE DRAWINGS

FIG. 1A is a bar graph showing the RNA expression of the antigens from which the peptides of Exemplary Vaccine 1 are derived in human ovarian cancer cell (882AC) relative to human ovarian epithelial cell (HoEpic) based on quantitative real-time PCR analysis.

FIG. 1B is a bar graph showing the RNA expression of the antigens from which the peptides of Exemplary Vaccine 1 are derived in cancer stem cell (882CSC) relative to human ovarian epithelial cell (HoEpic) based on quantitative real-time PCR analysis.

FIG. 1C is a bar graph showing the RNA expression of the antigens from which the peptides of Exemplary Vaccine 1 are derived in ovarian cancer daughter cell (882ADC) relative to human ovarian epithelial cell (HoEpic) based on quantitative real-time PCR analysis.

FIG. 2A is a bar graph showing the RNA expression of the antigens from which the peptides of Exemplary Vaccine 1 are derived in human ovarian cancer stem cell (882CSC) relative to human ovarian cancer cell (882AC).

FIG. 2B is a bar graph showing the RNA expression of the antigens of Exemplary Vaccine 1 in human ovarian cancer daughter cell (882ADC) relative to human ovarian cancer stem cell (882CSC).

FIG. 3A is a bar graph showing the RNA expression of the antigens from which the peptides of Exemplary Vaccine 1 are derived in human ovarian cancer cells (1031ADC) relative to human ovarian epithelial cell (HoEpic) based on quantitative real-time PCR analysis.

FIG. 3B is a bar graph showing the RNA expression of the antigens from which the peptides of Exemplary Vaccine 1 are derived in cancer stem cells (1031CSC) relative to human ovarian epithelial cell (HoEpic) based on quantitative real-time PCR analysis.

FIG. 3C is a bar graph showing the RNA expression of the antigens from which the peptides of Exemplary Vaccine 1 are derived in ovarian cancer daughter cells (1031ADC) relative to human ovarian epithelial cell (HoEpic) based on quantitative real-time PCR analysis.

FIG. 9A is a graph depicting overall survival (OS) based on RNA expression of IL-13Rα2 in human ovarian cancer patients (Dataset: GSE 9891, 285 human ovarian cancer patients). In this figure, the high expression curve is the bottom curve in the graph.

FIG. 9B is a graph depicting overall survival (OS) based on RNA expression of NY-ESO-1 in human ovarian cancer patients (Dataset: GSE 9891, 285 human ovarian cancer patients). In this figure, the high expression curve is the upper curve in the graph.

DETAILED DESCRIPTION

Figure 4A:
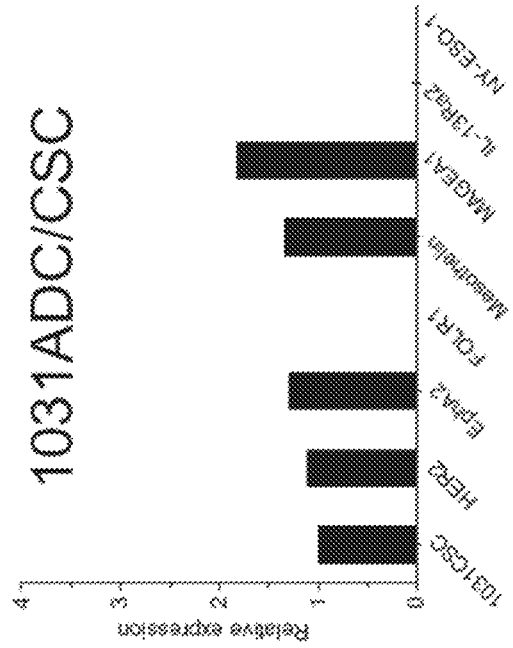
FIG. 4A is a bar graph showing the RNA expression of the antigens from which the peptides of Exemplary Vaccine 1 are derived in human ovarian cancer stem cell (1031CSC) relative to human ovarian cancer cell (1031AC).

This disclosure relates in part to compositions that are useful to treat gynecological and peritoneal cancers. The compositions described herein include antigen presenting cells (e.g., dendritic cells) presenting epitopes from at least seven tumor-associated antigens (i.e., mesothelin, NY-ESO-1, Folate Binding Protein (FBP), Human Epidermal Growth Factor Receptor 2 (HER-2/neu), IL-13 receptor α2, Melanoma-associated antigen 1(MAGE-A1), and EPH receptor A2 (EphA2)) that elicit therapeutic and tumor-specific immune responses. The compositions described herein also include multipeptide mixtures of epitopes comprising at least seven of the above-listed tumor-associated antigens. These compositions target multiple tumor cell functions and stimulate a more heterogeneous immune response than would be elicited with epitopes from a single antigen and thus, are particularly beneficial for targeting tumors. Often, a tumor will evolve to turn off the expression of a particular tumor associated antigen, creating "escape mutants". Thus, an immune response against multiple tumor antigens is more likely to provide effective therapy to deal with such mutants, and can provide significant therapeutic benefits for various patient populations. In addition, the compositions described herein provide the ability to treat all gynecological and peritoneal tumors. A further advantage of the compositions described herein is that they target antigens that are expressed early in the disease that are upregulated with progression of the disease.

Table 1 provides a listing of the seven antigens and exemplary MHC class I peptide epitopes of Exemplary Vaccine 1.

TABLE 1

| Antigen | A2 peptide epitope(s) | Ag Expression in Ovarian Cancer | Immunogenicity in vitro | Function |
| --- | --- | --- | --- | --- |
| Mesothelin | SLLFLLFSL (SEQ ID NO: 15); VLPLTVAEV (SEQ ID NO: 17) | 67-100% | Yes | Facilitate metastasis; Maintain viability |

TABLE 1-continued

| Antigen | A2 peptide epitope(s) | Ag Expression in Ovarian Cancer | Immunogenicity in vitro | Function |
|---|---|---|---|---|
| NY-ESO-1 | SLLMWITQC (SEQ ID NO: 26) | 11-20% | Yes | unknown |
| Folate Binding Protein | EIWTHSYKV (SEQ ID NO: 28) | >90% | Yes | Tumor growth advantage |
| HER2/neu | VMAGVGSPYV (SEQ ID NO: 40) | 100%-Stage III/IV | Yes | Signal transduction |
| IL-13Rα2 | WLPFGFILI (SEQ ID NO: 49) | 83% | Yes | Gain of function, IL13 responsiveness |
| MAGE-A1 | KVLEYVIKV (SEQ ID NO: 55) | 30-55% | Yes | unknown |
| EphA2 | TLADFDPRV (SEQ ID NO: 66) | 76% | Yes | Receptor tyrosine kinase (RTK) |

This disclosure also relates in part to methods for treating gynecological (e.g., ovarian, fallopian tube) and peritoneal (e.g., primary peritoneal) cancers by administering a multi-peptide vaccine comprising mixtures of epitopes from at least the seven tumor antigens disclosed above, or by administering antigen presenting cells presenting unique combinations of epitopes from the tumor antigens disclosed above. The combinations of epitopes from the antigens can be administered to the patients either as a multipeptide vaccine, or can be presented on the surface of antigen presenting cells (e.g., dendritic cells). Vaccination with antigen presenting cells is safe and elicits a cytotoxic T cell response that leads to the elimination of tumor cells expressing one or more of these antigens.

The compositions and methods of this application feature at least one epitope of at least the following seven antigens: mesothelin, NY-ESO-1, FBP, HER-2/neu, IL-13 receptor α2, MAGE-A1 and EphA2. The compositions and methods may also feature one or more epitopes of at least one, two, three, four, five, six, or seven of the following antigens: p53, k-Ras, Epithelial Cell Adhesion Molecule (Ep-CAM), Mucin 1(MUC1), Survivin, human Telomerase Reverse Transcriptase (hTERT), and WT1; these epitopes may be MHC class I (e.g., HLA-A2) and/or class II epitopes. In one embodiment, the application features combinations or mixtures of one or more MHC class I epitopes of the following seven antigens: mesothelin, NY-ESO-1, FBP, HER-2/neu, IL-13 receptor α2, MAGE-A1, and EphA2. In a specific embodiment, the epitopes are peptides that bind HLA-A2.

Table 2 lists the amino acid sequences of the above-listed antigens. Table 3 provides non-limiting examples of epitopes of these antigens.

Antigens

Mesothelin

Mesothelin is a differentiation antigen present on normal mesothelial cells and overexpressed in several human tumors, including mesothelioma, ovarian cancer, and pancreatic adenocarcinoma. The mesothelin gene encodes a precursor protein that is processed to yield the 40-kDa protein, mesothelin, which is attached to the cell membrane by a glycosylphosphatidyl inositol linkage and a 31-kDa shed fragment named megakaryocyte-potentiating factor. This protein is thought to play a role in cancer metastasis by mediating cell adhesion by binding to MUC16/CA-125.

Table 2 provides an amino acid sequence of the 622 amino acid human mesothelin protein (also available in GenBank under accession no. NP_001170826.1). Exemplary sequences of mesothelin HLA epitopes are provided in Table 3.

NY-ESO-1

Although NY-ESO-1 is expressed in normal adult tissues solely in the testicular germ cells of normal adults, it is expressed in various cancers including melanoma, lung, breast, and ovarian cancers.

Human NY-ESO-1 is 180 amino acids in length. Table 2 provides an amino acid sequence of human NY-ESO-1 (also available in GenBank under accession no. CAA05908.1). Exemplary sequences of NY-ESO-1 HLA epitopes are listed in Table 3.

FBP

Folate Binding Protein exhibits a strong affinity for human folic acid. Folate binding protein is overexpressed in cancers including ovarian, endometrial, breast, lung, colorectal, and renal cell carcinomas.

Human FBP is 257 amino acids in length. Table 2 provides an amino acid sequence of human FBP (also available in GenBank under accession no. NP_057941.1). Exemplary sequences of FBP HLA epitopes are provided in Table 3.

HER-2

HER-2 (also known as HER-2/neu, and c-erbB2) is a 1255 amino acid transmembrane glycoprotein with tyrosine kinase activity. HER-2 is overexpressed in a variety of tumor types. This protein promotes tumor growth by activating a variety of cell signaling pathways including MAPK, PI3K/Akt, and PKC.

Table 2 provides an amino acid sequence of human HER-2 (also available in GenBank under accession no. NP_004439.2). Exemplary sequences of HER-2 HLA are listed in Table 3.

IL-13 Receptor α2

IL-13 receptor α2 is a non-signaling component of the multimeric IL-13 receptor. Stimulation of this receptor activates production of TFG-β1, which inhibits cytotoxic T cell function. The human IL-13 receptor α2 amino acid sequence, which is 380 amino acids in length, is shown in Table 2 (also available in Genbank under accession no. NP_000631.1). An exemplary sequence of an IL-13 receptor α2 HLA epitope is shown in Table 3.

MAGE A1

MAGE-A1 is a protein found in testicular germ cells and plays an important role in spermatogenesis. MAGE-A1 is also expressed in several cancers including brain, ovarian, lung, and liver.

The MAGE-A1 protein is 309 amino acids in length. Table 2 provides an amino acid sequence of human MAGE-1 (also available in GenBank under accession no. NP_004979.3). Exemplary sequences of a MAGE-A1 HLA epitopes are shown in Table 3.

EphA2

EphA2 belongs to the ephrin receptor subfamily of the protein-tyrosine kinase family. EPH and EPH-related receptors have been implicated in mediating developmental events, particularly in the nervous system. Receptors in the EPH subfamily typically have a single kinase domain and an extracellular region containing a Cys-rich domain and two fibronectin type III repeats. The ephrin receptors are divided into 2 groups based on the similarity of their extracellular domain sequences and their affinities for binding ephrin-A and ephrin-B ligands. EphA2 binds ephrin-A ligands and is a transcriptional target of the Ras-MAPK pathway. It is thought to play a role in tumor cell invasion by regulating integrins and focal adhesion kinase (FAK) dephosphorylation.

Table 2 provides a sequence of human EphA2 which has 976 amino acids (also available in GenBank under accession no. NP_004422.2). Exemplary sequences of EphA2 HLA epitopes are provided in Table 3.

p53 p53 is a tumor suppressor protein that is crucial in multicellular organisms, where it regulates the cell cycle and, thus, functions as a tumor suppressor that is involved in preventing cancer. p53 has been referred to as "the guardian of the genome" because of its role in conserving stability by preventing genome mutation. p53 is a transcription factor that can bind to promoter regions of hundreds of genes where it either activates or suppresses gene expression. p53 serves as a tumor suppressor by inducing cell cycle arrest, apoptosis, senescence and DNA repair. In normal cells, p53 is frequently undetectable due to fast ubiquitination by mdm-2 and subsequent proteasomal degradation. However, upon DNA damage and several other stresses, including oncogenic stress, the amount of p53 is increased due to disruption of its degradation. Notably, inactivation of p53 is one of the characteristics of cancer. Indeed, p53 has a wide spectrum of mutation types and p53 is found mutated in approximately half of all tumors.

Table 2 provides a sequence of human p53 which has 393 amino acids (also available in GenBank under accession no. NP_000537.3). Table 3 lists exemplary p53 epitopes.

K-Ras

Kirsten rat sarcoma viral oncogene homolog also known as KRAS is a protein that performs essential functions in normal tissue signaling. Like other members of the Ras family, the KRAS protein is a GTPase and is an early player in many signal transduction pathways. KRAS is usually tethered to cell membranes because of the presence of an isoprenyl group on its C-terminus. The mutation of a KRAS gene is an essential step in the development of many cancers.

Table 2 provides a sequence of human k-Ras which is 188 amino acids in length (also available in GenBank under accession no. NP_004976.2). Table 3 lists exemplary k-Ras HLA epitopes.

Ep-CAM

EpCAM is a pan-epithelial differentiation antigen that is expressed on almost all carcinomas. It is a single-pass type I membrane protein. Table 2 provides a sequence of human Ep-CAM which is 314 amino acids in length (also available in GenBank under accession no. NP_002345.2). Table 3 lists exemplary Ep-CAM HLA epitopes

MUC1

MUC1 is a glycoprotein with extensive O-linked glycosylation of its extracellular domain. MUC1 lines the apical surface of epithelial cells of several organs such as the lungs, stomach, intestines, and eyes. MUC1 protects the body from infection by preventing pathogen from reaching the cell surface by capturing the pathogen in oligosaccharides in the extracellular domain. Overexpression of MUC1 is often associated with colon, breast, ovarian, lung and pancreatic cancers.

Table 2 provides a sequence of human survivin which is 264 amino acids in length (also available in GenBank under accession no. NP_001018016.1). Table 3 provides exemplary MUC1 HLA epitopes.

Survivin

Survivin is a member of the inhibitor of apoptosis family. Survivin inhibits caspase activation, thereby leading to negative regulation of apoptosis or programmed cell death. Survivin is expressed highly in most human tumours and fetal tissue, but is completely absent in terminally differentiated cells. This fact makes survivin an ideal target for cancer therapy as cancer cells are targeted while normal cells are left alone.

Table 2 provides a sequence of human survivin which is 137 amino acids in length (also available in GenBank under accession no. NP_001012270.1). Exemplary HLA epitopes of survivin are listed in Table 3.

hTERT

Telomerase reverse transcriptase is a catalytic subunit of the enzyme telomerase. Telomerase is a ribonucleoprotein polymerase that lengthens telomeres. Telomeres protect the ends of the chromosomes from destruction and normal cell death. The telomerase protein plays a role in normal cell death because it is usually repressed, resulting in progressive shortening of telomeres. When telomerase begins to function abnormally, the cell can become immortal. This process is thought to be important in the development of several types of cancer.

Table 2 provides a sequence of human TERT which is 1069 amino acids in length (also available in GenBank under accession no. NP_001180305.1). Table 3 lists exemplary hTERT HLA epitopes.

WT1

WT1 is a zinc finger transcription factor that plays an essential role in the development of the urogenital system. It is overexpressed in several types of leukemia and solid tumors. Table 2 provides a sequence of human WT1 which is 449 amino acids in length (also available in GenBank under accession no. AAA61299.1). Exemplary HLA epitopes of WT1 are listed in Table 3.

TABLE 2

Amino Acid Sequences of Antigens

| Tumor antigen | Amino acid sequence |
|---|---|
| Mesothelin | MALPTARPLL GSCGTPALGS LLFLLFSLGW VQPSRTLAGE TGQEAAPLDG VLANPPNISS LSPRQLLGFP CAEVSGLSTE RVRELAVALA QKNVKLSTEQ LRCLAHRLSE PPEDLDALPL DLLLFLNPDA FSGPQACTRF FSRITKANVD LLPRGAPERQ RLLPAALACW GVRGSLLSEA DVRALGGLAC DLPGRFVAES AEVLLPRLVS CPGPLDQDQQ EAARAALQGG GPPYGPPSTW SVSTMDALRG LLPVLGQPII RSIPQGIVAA WRQRSSRDPS WRQPERTILR PRFRREVEKT ACPSGKKARE IDESLIFYKK WELEACVDAA LLATQMDRVN AIPPFTYEQLD VLKHKLDELY PQGYPESVIQ HLGYLFLKMS PEDIRKWNVT SLETLKALLE VNKGHEMSPQ VATLIDRFVK GRGQLDKDTL DTLTAFYPGY LCSLSPEELS SVPPSSIWAV RPQDLDTCDP RQLDVLYPKA RLAFQNMNGS EYFVKIQSFL GGAPTEDLKA LSQQNVSMDL ATFMKLRTDA VLPLTVAEVQ KLLGPHVEGL KAEERHRPVR DWILRQRQDD LDTLGLGLQG GIPNGYLVLD LSMQEALSGT PCLLGPGPVL TVLALLLAST LA (SEQ ID NO: 1) |
| NY-ESO-1 | MQAEGRGTGG STGDADGPGG PGIPDGPGGN AGGPGEAGAT GGRGPRGAGA ARASGPGGGA PRGPHGGAAS GLNGCCRCGA RGPESRLLEF YLAMPFATPM EAELARRSLA QDAPPLPVPG VLLKEFTVSG NILTIRLTAA DHRQLQLSIS SCLQQLSLLM WITQCFLPVF LAQPPSGQRR (SEQ ID NO: 2) |
| FBP | MAQRMTTQLL LLLVWVAVVG EAQTRIAWAR TELLNVCMNA KHHKEKPGPE DKLHEQCRPW RKNACCSTNT SQEAHKDVSY LYRFNWNHCG EMAPACKRHF IQDTCLYECS PNLGPWIQQV DQSWRKERVL NVPLCKEDCE QWWEDCRTSY TCKSNWHKCA NWTSGFNKCA VGAACQPPHF YFPTPTVLCN EIWTHSYKVS NYSRGSGRCI QMWFDPAQGN PNEEVARFYA AAMSGAGPWA AWPFLLSLAL MLLWLLS (SEQ ID NO: 3) |
| HER-2 | MELAALCRWG LLLLALLPPGA ASTQVCTGTD MKLRLPASPE THLDMLRHLY QGCQVVQGNL ELTYLPTNAS LSFLQDIQEV QGYVLIAHNQ VRQVPLQRLR IVRGTQLFED NYALAVLDNG DPLNNTTPVT GASPGGLREL QLRSLTEILK GGVLIQRNPQ LCYQDTILWK DIFHKNNQLA LTLIDTNRSR ACHPCSPMCK GSRCWGESSE DCQSLTRTVC AGGCARCKGP LPTDCCHEQC AAGCTGPKHS DCLACLHFNH SGICELHCPA LVTYNTDTFE SMPNPEGRYT FGASCVTACP YNYLSTDVGS CTLVCPLHNQ EVTAEDGTQR CEKCSKPCAR VCYGLGMEHL REVRAVTSAN IQEFAGCKKI FGSLAFLPES FDGDPASNTA PLQPEQLQVF ETLEEITGYL YISAWPDSLP DLSVFQNLQV IRGRILHNGA YSLTLQGLGI SWLGLRSLRE LGSGLALIHH NTHLCFVHTV PWDQLFRNPH QALLHTANRP EDECVGEGLA CHQLCARGHC WGPGPTQCVN CSQFLRGQEC VEECRVLQGL PREYVNARHC LPCHPECQPQ NGSVTCFGPE ADQCVACAHY KDPPFCVARC PSGVKPDLSY MPIWKFPDEE GACQPCPINC THSCVDLDDK GCPAEQRASP LTSIISAVVG ILLVVVLGVV FGILIKRRQQ KIRKYTMRRL LQETELVEPL TPSGAMPNQA QMRILKETEL RKVKVLGSGA FGTVYKGIWI PDGENVKIPV AIKVLRENTS PKANKEILDE AYVMAGVGSP YVSRLLGICL TSTVQLVTQL MPYGCLLDHV RENRGRLGSQ DLLNWCMQIA KGMSYLEDVR LVHRDLAARN VLVKSPNHVK ITDFGLARLL DIDETEYHAD GGKVPIKWMA LESILRRRFT HQSDVWSYGV TVWELMTFGA KPYDGIPARE IPDLLEKGER LPQPPICTID VYMIMVKCWM IDSECRPRFR ELVSEFSRMA RDPQRFVVIQ NEDLGPASPL DSTFYRSLLE DDDMGDLVDA EEYLVPQQGF FCPDPAPGAG GMVHHRHRSS STRSGGGDLT LGLEPSEEEA PRSPLAPSEG AGSDVFDGDL GMGAAKGLQS LPTHDPSPLQ RYSEDPTVPL PSETDGYVAP LTCSPQPEYV NQPDVRPQPP SPREGPLPAA RPAGATLERP KTLSPGKNGV VKDVFAFGGA VENPEYLTPQ GGAAPQPHPP PAFSPAFDNL YYWDQDPPER GAPPSTFKGT PTAENPEYLG LDVPV (SEQ ID NO: 4) |
| IL-13 receptor α2 | MAFVCLAIGC LYTFLISTTF GCTSSSDTEI KVNPPQDFEI VDPGYLGYLY LQWQPPLSLD HFKECTVEYE LKYRNIGSET WKTIITKNLH YKDGFDLNKG IEAKIHTLLP WQCTNGSEVQ SSWAETTYWI SPQGIPETKV QDMDCVYYNW QYLLCSWKPG IGVLLDTNYN LFWYEGLDH ALQCVDYIKA DGQNIGCRFP YLEASDYKDF YICVNGSSEN KPIRSSYFTF QLQNIVKPLP PVYLTFTRES SCEIKLKWSI PLGPIPARCF DYEIEIREDD TTLVTATVEN ETYTLKTTNE TRQLCFVVRS KVNIYCSDDG IWSEWSDKQC WEGEDLSKKT LLRFWLPFGF ILILVIFVTG LLLRKPNTYP KMIPEFFCDT (SEQ ID NO: 5) |
| MAGE-A1 | MSLEQRSLHC KPEEALEAQQ EALGLVCVQA ATSSSSPLVL GTLEEVPTAG STDPPQSPQG ASAFPTTINF TRQRQPSEGS SSREEEGPST SCILESLFRA VITKKVADLV GFLLLKYRAR EPVTKAEMLE SVIKNYKHCF PEIFGKASES LQLVFGIDVK EADPTGHSYV LVTCLGLSYD GLLGDNQIMP KTGFLIIVLV MIAMEGGHAP EEEIWEELSV MEVYDGREHS AYGEPRKLLT QDLVQEKYLE YRQVPDSDPA RYEFLWGPRA LAETSYKVL EYVIKVSARV RFFFPSLREA ALREEEEGV (SEQ ID NO: 6) |
| EphA2 | MELQAARACF ALLWGCALAA AAAQGKEVV LLDFAAAGGE LGWLTHPYGK GWDLMQNIMN DMPIYMYSVC NVMSGDQDNW LRTNWVYRGE AERIFIELKF TVRDCNSFPG GASSCKETFN LYYAESDLDY GTNFQKRLFT KIDTIAPDEI TVSSDFEARH VKLNVEERSV GPLTRKGFYL AFQDIGACVA LLSVRVYYKK CPELLQGLAH FPETIAGSDA PSLATVAGTC VDHAVVPPGG EEPRMHCAVD GEWLVPIGQC LCQAGYEKVE DACQACSPGF FKFEASESPC LECPEHTLPS PEGATSCECE EGFFRAPQDP ASMPCTRPPS APHYLTAVGM GAKVELRWTP PQDSGGREDI VYSVTCEQCW PESGECGPCE ASVRYSEPPH GLTRTSVTVS DLEPHMNYTF TVEARNGVSG LVTSRSFRTA SVSINQTEPP KVRLEGRSTT SLSVSWSIPP PQQSRVWKYE VTYRKKGDSN SYNVRRTEGF SVTLDDLAPD TTYLVQVQAL TQEGQGAGSK VHEFQTLSPE GSGNLAVIGG VAVGVVLLLV LAGVGFFIHR RRKNQRARQS PEDVYFSKSE QLKPLKTYVD PHTYEDPNQA VLKFTTEIHP SCVTRQKVIG AGEFGEVYKG MLKTSSGKKE VPVAIKTLKA GYTEKQRVDF LGEAGIMGQF SHHNIIRLEG VISKYKPMMI ITEYMENGAL DKFLREKDGE FSVLQLVGML RGIAAGMKYL ANMNYVHRDL AARNILVNSN LVCKVSDFGL SRVLEDDPEA TYTTSGGKIP IRWTAPEAIS YRKFTSASDV WSFGIVMWEV MTYGERPYWE LSNHEVMKAI NDGFRLPTPM |

TABLE 2-continued

Amino Acid Sequences of Antigens

| Tumor antigen | Amino acid sequence |
|---|---|
| | DCPSAIYQLM MQCWQQERAR RPKFADIVSI LDKLIRAPDS LKTLADFDPR VSIRLPSTSG SEGVPFRTVS EWLESIKMQQ YTEHFMAAGY TAIEKVVQMT NDDIKRIGVR LPGHQKRIAY SLLGLKDQVN TVGIPI (SEQ ID NO: 7) |
| p53 | MEEPQSDPSV EPPLSQETFS DLWKLLPENN VLSPLPSQAM DDLMLSPDDI EQWFTEDPGP DEAPRMPEAA PPVAPAPAAP TPAAPAPAPS WPLSSSVPSQ KTYQGSYGFR LGFLHSGTAK SVTCTYSPAL NKMFCQLAKT CPVQLWVDST PPPGTRVRAM AIYKQSQHMT EVVRRCPHHE RCSDSDGLAP PQHLIRVEGN LRVEYLDDRN TFRHSVVVPY EPPEVGSDCT TIHYNYMCNS SCMGGMNRRP ILTIITLEDS SGNLLGRNSF EVRVCACPGR DRRTEEENLR KKGEPHHELP PGSTKRALPN NTSSSPQPKK KPLDGEYFTL QIRGRERFEM FRELNEALEL KDAQAGKEPG GSRAHSSHLK SKKGQSTSRH KKLMFKTEGP DSD (SEQ ID NO: 8) |
| k-Ras | MTEYKLVVVG AGGVGKSALT IQLIQNHFVD EYDPTIEDSY RKQVVIDGET CLLDILDTAG QEEYSAMRDQ YMRTGEGFLC VFAINNTKSF EDIHHYREQI KRVKDSEDVP MVLVGNKCDL PSRTVDTKQA QDLARSYGIP FIETSAKTRQ GVDDAFYTLV REIRKHKEKM SKDGKKKKKK SKTKCVIM (SEQ ID NO: 9) |
| Ep-CAM | MAPPQVLAFG LLLAAATATF AAAQEECVCE NYKLAVNCFV NNNRQCQCTS VGAQNTVICS KLAAKCLVMK AEMNGSKLGR RAKPEGALQN NDGLYDPDCD ESGLFKAKQC NGTSMCWCVN TAGVRRTDKD TEITCSERVR TYWIIIELKH KAREKPYDSK SLRTALQKEI TTRYQLDPKF ITSILYENNV ITIDLVQNSS QKTQNDVDIA DVAYYFEKDV KGESLFHSKK MDLTVNGEQL DLDPGQTLIY YVDEKAPEFS MQGLKAGVIA VIVVVVIAVV AGIVVLVISR KKRMAKYEKA EIKEMGEMHR ELNA (SEQ ID NO: 10) |
| MUC1 | MTPGTQSPFF LLLLLTVLTA TTAPKPATVV TGSGHASSTP GGEKETSATQ RSSVPSSTEK NAFNSSLEDP STDYYQELQR DISEMFLQIY KQGGFLGLSN IKFRPGSVVV QLTLAFREGT INVHDVETQF NQYKTEAASR YNLTISDVSV SDVPFPFSAQ SGAGVPGWGI ALLVLVCVLV ALAIVYLIAL AVCQCRRKNY GQLDIFPARD TYHPMSEYPT YHTHGRYVPP SSTDRSPYEK VSAGNGGSSL SYTNPAVAAT SANL (SEQ ID NO: 11) |
| Survivin | MGAPTLPPAW QPFLKDHRIS TFKNWPFLEG CACTPERMAE AGFIHCPTEN EPDLAQCFFC FKELEGWEPD DDPMQRKPTI RRKNLRKLRR KCAVPSSSWL PWIEASGRSC LVPEWLHHFQ GLFPGATSLP VGPLAMS (SEQ ID NO: 12) |
| hTERT | MPRAPRCRAV RSLLRSHYRE VLPLATFVRR LGPQGWRLVQ RGDPAAFRAL VAQCLVCVPW DARPPPAAPS FRQVSCLKEL VARVLQRLCE RGAKNVLAFG FALLDGARGG PPEAFTTSVR SYLPNTVTDA LRGSGAWGLL LRRVGDDVLV HLLARCALFV LVAPSCAYQV CGPPLYQLGA ATQARPPPHA SGPRRRLGCE RAWNHSVREA GVPLGLPAPG ARRRGGSASR SLPLPKRPRR GAAPEPERTP VGQGSWAHPG RTRGPSDRGF CVVSPARPAE EATSLEGALS GTRHSHPSVG RQHHAGPPST SRPPRPWDTP CPPVYAETKH FLYSSGDKEQ LRPSFLLSSL RPSLTGARRL VETIFLGSRP WMPGTPRRLP RLPQRYWQMR PLFLELLGNH AQCPYGVLLK THCPLRAAVT PAAGVCAREK PQGSVAAPEE EDTDPRRLVQ LLRQHSSPWQ VYGFVRACLR RLVPPGLWGS RHNERRFLRN TKKFISLGKH AKLSLQELTW KMSVRDCAWL RRSPGVGCVP AAEHRLREEI LAKFLHWLMS VYVVELLRSF FYVTETTFQK NRLFFYRKSV WSKLQSIGIR QHLKRVQLRE LSEAEVRQHR EARPALLTSR LRFIPKPDGL RPIVNMDYVV GARTFRREKR AERLTSRVKA LFSVLNYERA RRPGLLGASV LGLDDIHRAW RTFVLRVRAQ DPPPELYFVK VDVTGAYDTI PQDRLTEVIA SIIKPQNTYC VRRYAVVQKA AHGHVRKAFK SHVSTLTDLQ PYMRQFVAHL QETSPLRDAV VIEQSSSLNE ASSGLFDVFL RFMCHHAVRI RGKSYVQCQG IPQGSILSTL LCSLCYGDME NKLFAGIRRD GLLLRLVDDF LLVTPHLTHA KTFLSYARTS IRASLTFNRG FKAGRNMRRK LFGVLRLKCH SLFLDLQVNS LQTVCTNIYK ILLLQAYRFH ACVLQLPFHQ QVWKNPTFFL RVISDTASLC YSILKAKNAG MSLGAKGAAG PLPSEAVQWL CHQAFLLKLT RHRVTYVPLL GSLRTAQTQL SRKLPGTTLT ALEAAANPAL PSDFKTILD (SEQ ID NO: 13) |
| WT1 | MGSDVRDLNA LLPAVPSLGG GGGCALPVSG AAQWAPVLDF APPGASAYGS LGGPAPPPAP PPPPPPPPHS FIKQEPSWGG AEPHEEQCLS AFTVHFSGQF TGTAGACRYG PFGPPPPSQA SSGQARMFPN APYLPSCLES QPAIRNQGYS TVTFDGTPSY GHTPSHHAAQ FPNHSFKHED PMGQQGSLGE QQYSVPPPVY GCHTPTDSCT GSQALLLRTP YSSDNLYQMT SQLECMTWNQ MNLGATLKGV AAGSSSSVKW TEGQSNHSTG YESDNHTTPI LCGAQYRIHT HGVFRGIQDV RRVPGVAPTL VRSASETSEK RPFMCAYPGC NKRYFKLSHL QMHSRKHTGE KPYQCDFKDC ERRFSRSDQL KRHQRRHTGV KPFQCKTCQR KFSRSDHLKT HTRTHTGKTS EKPFSCRWPS CQKKFARSDE LVRHHNMHQR NMTKLQLAL (SEQ ID NO: 14) |

TABLE 3

Tumor Antigen Peptides

| Tumor antigen | Position in sequence | Peptide sequence |
|---|---|---|
| Mesothelin | 20-28 | SLLFLLFSL (SEQ ID NO: 15) |
| Mesothelin | 23-31 | FLLFSLGWV (SEQ ID NO: 16) |
| Mesothelin | 530-538 | VLPLTVAEV (SEQ ID NO: 17) |
| Mesothelin | 547-556 (wt) | KLLGPHVEGL (SEQ ID NO: 18) |
| Mesothelin | 547-556 (554L) | KLLGPHVLGL (SEQ ID NO: 19) |
| Mesothelin | 547-556 (554L/556V) | KLLGPHVLGV (SEQ ID NO: 20) |
| Mesothelin | 547-556 (548M/554L/556V) | KMLGPHVLGV (SEQ ID NO: 21) |
| Mesothelin | 547-556 (548M/554L) | KMLGPHVLGL (SEQ ID NO: 22) |
| Mesothelin | 547-556 (548I/554L) | KILGPHVLGL (SEQ ID NO: 23) |
| Mesothelin | 547-556 (547Y/554L/556V) | YLLGPHVLGV (SEQ ID NO: 24) |
| Mesothelin | 547-556 (547Y/554L) | YLLGPHVLGL (SEQ ID NO: 25) |
| NY-ESO-1 | 157-165 | SLLMWITQC (SEQ ID NO: 26) |
| NY-ESO-1 | 158-166 | LLMWITQCF (SEQ ID NO: 27) |
| FBP | 191-199 | EIWTHSTKV (SEQ ID NO: 28) |
| FBP | 245-253 | LLSLALMLL (SEQ ID NO: 29) |
| HER-2 | 5-13 | ALCRWGLLL (SEQ ID NO: 30) |
| HER-2 | 8-16 | RWGLLLALL (SEQ ID NO: 31) |
| HER-2 | 63-71 | TYLPTNASL (SEQ ID NO: 32) |
| HER-2 | 106-114 | QLFEDNYAL (SEQ ID NO: 33) |
| HER-2 | 369-377 | KIFGSLAFL (SEQ ID NO: 34) |
| HER-2 | 435-443 | ILHNGAYSL (SEQ ID NO: 35) |
| HER-2 | 654-662 | IISAVVGIL (SEQ ID NO: 36) |
| HER-2 | 665-673 | VVLGVVFGI (SEQ ID NO: 37) |
| HER-2 | 689-697 | RLLQETELV (SEQ ID NO: 38) |
| HER-2 | 754-762 | VLRENTSPK (SEQ ID NO: 39) |
| HER-2 | 773-782 | VMAGVGSPYV (SEQ ID NO: 40) |
| HER-2 | 780-788 | PYVSRLLGI (SEQ ID NO: 41) |
| HER-2 | 789-797 | CLTSTVQLV (SEQ ID NO: 42) |
| HER-2 | 799-807 | QLMPYGCLL (SEQ ID NO: 43) |
| HER-2 | 835-842 | YLEDVRLV (SEQ ID NO: 44) |
| HER-2 | 851-859 | VLVKSPNHV (SEQ ID NO: 45) |
| HER-2 | 883-899 | KVPIKWMALESILRRRF (SEQ ID NO: 46) |

TABLE 3-continued

Tumor Antigen Peptides

| Tumor antigen | Position in sequence | Peptide sequence |
|---|---|---|
| HER-2 | 952-961 | YMIMVKCWMI (SEQ ID NO: 47) |
| HER-2 | 971-979 | ELVSEFSRM (SEQ ID NO: 48) |
| IL-13 receptor α2 | 345-354 | WLPFGFILI (SEQ ID NO: 49) |
| MAGE-A1 | 102-112 | ITKKVADLVGF (SEQ ID NO: 50) |
| MAGE-A1 | 135-143 | NYKHCFPEI (SEQ ID NO: 51) |
| MAGE-A1 | 160-169 | KEADPTGHSY (SEQ ID NO: 52) |
| MAGE-A1 | 161-169 | EADPTGHSY (SEQ ID NO: 53) |
| MAGE-A1 | 230-238 | SAYGEPRKL (SEQ ID NO: 54) |
| MAGE-A1 | 278-286 | KVLEYVIKV (SEQ ID NO: 55) |
| EphA2 | 12-20 | LLWGCALAA (SEQ ID NO: 56) |
| EphA2 | 58-66 | IMNDMPIYM (SEQ ID NO: 57) |
| EphA2 | 120-128 | NLYYAESDL (SEQ ID NO: 58) |
| EphA2 | 162-170 | KLNVEERSV (SEQ ID NO: 59) |
| EphA2 | 253-261 | WLVPIGQCL (SEQ ID NO: 60) |
| EphA2 | 391-399 | GLTRTSVTV (SEQ ID NO: 61) |
| EphA2 | 546-554 | VLLLVLAGV (SEQ ID NO: 62) |
| EphA2 | 550-558 | VLAGVGFFI (SEQ ID NO: 63) |
| EphA2 | 806-814 | VMWEVMTYG (SEQ ID NO: 64) |
| EphA2 | 873-881 | KLIRAPDSL (SEQ ID NO: 65) |
| EphA2 | 883-891 | TLADFDPRV (SEQ ID NO: 66) |
| EphA2 | 925-933 | FMAAGYTAI (SEQ ID NO: 67) |
| EphA2 | 961-969 | SLLGLKDQV (SEQ ID NO: 68) |
| p53 | 65-73 wt | RMPEAAPPV (SEQ ID NO: 69) |
| p53 | 103-111 L2 m | YLGSYGFRL (SEQ ID NO: 70) |
| p53 | 139-147 wt | KTCPVQLWV (SEQ ID NO: 71) |
| p53 | 139-147 L2 m | KLCPVQLWV (SEQ ID NO: 72) |
| p53 | 139-147 L2B3 m | KLBPVQLWV (SEQ ID NO: 73) |
| p53 | 149-157 wt | STPPPGTRV (SEQ ID NO: 74) |
| p53 | 149-157 L2 m | SLPPPGTRV (SEQ ID NO: 75) |
| p53 | 149-157 M2 m | SMPPPGTRV (SEQ ID NO: 76) |
| p53 | 187-197 wt | GLAPPQHLIRV (SEQ ID NO: 77) |
| p53 | 217-225 wt | VVPYEPPEV (SEQ ID NO: 78) |
| p53 | 264-272 wt | LLGRNSFEV (SEQ ID NO: 79) |
| p53 | 264-272 7W m | LLGRNSWEV (SEQ ID NO: 80) |
| k-Ras | 5-17 wt | KLVVVGAGGVGKS (SEQ ID NO: 81) |
| k-Ras | 5-17 D8 | KLVVVGADGVGKS (SEQ ID NO: 82) |
| k-Ras | 5-14 D8 | KLVVVGADGV (SEQ ID NO: 83) |

TABLE 3-continued

Tumor Antigen Peptides

| Tumor antigen | Position in sequence | Peptide sequence |
|---|---|---|
| k-Ras | 5-14 V8 | KLVVVGAVGV (SEQ ID NO: 84) |
| k-Ras | 5-14 C8 | KLVVVGACGV (SEQ ID NO: 85) |
| k-Ras | 4-12 V9 | YKLVVVGAV (SEQ ID NO: 86) |
| EpCAM | 6-14 | VLAFGLLLA (SEQ ID NO: 87) |
| EpCAM | 174-184 | YQLDPKFITSI (SEQ ID NO: 88) |
| EpCAM | 184-193 | ILYENNVITI (SEQ ID NO: 89) |
| EpCAM | 255-264 | KAPEFSMQGL (SEQ ID NO: 90) |
| EpCAM | 263-271 | GLKAGVIAV (SEQ ID NO: 91) |
| MUC1 | 12-20 | LLLLTVLTV (SEQ ID NO: 92) |
| MUC1 | 950-958, V5N7 | ST(A)PPVHNV (SEQ ID NO: 93) |
| Survivin | 18-28 | RISTFKNWPFL (SEQ ID NO: 94) |
| Survivin | 53-67 M57 | DLAQMFFCFKELEGW (SEQ ID NO: 95) |
| Survivin | 95-104 | ELTLGEFLKL (SEQ ID NO: 96) |
| Survivin | 96-104 wt | LTLGEFLKL (SEQ ID NO: 97) |
| Survivin | 96-104 M2 m | LMLGEFLKL (SEQ ID NO: 98) |
| hTERT | I540-548 | ILAKFLHWL (SEQ ID NO: 99) |
| hTERT | 572-580Y | YLFFYRKSV (SEQ ID NO: 100) |
| hTERT | 988Y | YLQVNSLQTV (SEQ ID NO: 101) |
| hTERT | 30-38 wt | RLGPQGWRL (SEQ ID NO: 102) |
| hTERT | 30-38 V9 m | RLGPQGWRV (SEQ ID NO: 103) |
| hTERT | 865-873 | RLVDDFLLV (SEQ ID NO: 104) |
| WT1 | 37-45 | VLDFAPPGA (SEQ ID NO: 105) |
| WT1 | 126-134 | RMFPNAPYL (SEQ ID NO: 106) |
| WT1 | R1Y WT1$_{126}$ | YMFPNAPYL (SEQ ID NO: 107) |
| WT1 | 187-195 | SLGEQQYSV (SEQ ID NO: 108) |
| WT1 | 235-243 | CMTWNQMNL (SEQ ID NO: 109) |

As noted above, the epitopes listed in Table 3 are exemplary. One of ordinary skill in the art would be able to identify other epitopes for these tumor associated antigens. In addition, the ordinary artisan would readily recognize that the epitopes listed in Table 3 can be modified by amino acid substitutions to alter HLA binding (e.g., to improve HLA binding). The epitopes may be modified at one, two, three, four, five, or six positions and tested for HLA binding activity. Based on such routine binding assays, those with the desired binding activity and those capable of inducing suitable T cell responsiveness can be selected for use.

The antigenic peptides described herein can be used in multipeptide vaccines or for loading antigen presenting cells which can then be used for vaccination. These epitopes stimulate a T cell mediated immune response (e.g., a cytotoxic T cell response) by presentation to T cells on MHC molecules. Therefore, useful peptide epitopes of Mesothelin, NY-ESO-1, FBP, HER-2/neu, IL-13 receptor α2, MAGE-A1, EphA2, p53, k-Ras, Ep-CAM, MUC1, Survivin, hTERT, and WT1 include portions of their amino acid sequences that bind to MHC molecules and in that bound state are presented to T cells.

Humans have three different genetic loci that encode MHC class I molecules (designated human leukocyte antigens (HLA)): HLA-A, HLA-B, and HLA-C. HLA-A*01, HLA-A*02, and HLA-A*11 are examples of different MHC class I alleles that can be expressed from these loci. Humans also have three different loci for MHC class II genes: HLA-DR, HLA-DQ, and HLA-DP. Peptides that bind to MHC class I molecules are generally 8-10 amino acids in length. Peptides that bind to MHC class II molecules are generally 13 amino acids or longer (e.g., 12-17 amino acids long).

T cell epitopes can be identified by a number of different methods. Naturally processed MHC epitopes can be identified by mass spectrophotometric analysis of peptides eluted from antigen-loaded APC (e.g., APC that have taken up antigen, or that have been engineered to produce the protein intracellularly). After incubation at 37° C., cells are lysed in detergent and the MHC protein is purified (e.g., by affinity chromatography). Treatment of the purified MHC with a suitable chemical medium (e.g., under acidic conditions, e.g., by boiling in 10% acetic acid, as described in Sanchez et al., Proc. Natl. Acad. Sci. USA, 94(9): 4626-4630, 1997) results in the elution of peptides from the MHC. This pool of peptides is separated and the profile compared with peptides from control APC treated in the same way. The peaks unique to the protein expressing/fed cells are analyzed (for example by mass spectrometry) and the peptide fragments identified. This protocol identifies peptides generated from a particular antigen by antigen processing, and provides a straightforward means of isolating these antigens.

Alternatively, T cell epitopes are identified by screening a synthetic library of peptides that overlap and span the length of the antigen in an in vitro assay. For example, peptides that are 9 amino acids in length and that overlap by 5 amino acids can be used. The peptides are tested in an antigen presentation system that includes antigen presenting cells and T cells. T cell activation in the presence of APCs presenting the peptide can be measured (e.g., by measuring T cell proliferation or cytokine production) and compared to controls, to determine whether a particular epitope is recognized by the T cells.

Another way to identify T cell epitopes is by algorithmic analysis of sequences that have predictive binding to HLA (see, e.g., www.immuneepitope.org) followed by binding studies and confirmation with in vitro induction of peptide specific CD8 T cells.

The T cell epitopes described herein can be modified to increase immunogenicity. One way of increasing immunogenicity is by the addition of dibasic amino acid residues (e.g., Arg-Arg, Arg-Lys, Lys-Arg, or Lys-Lys) to the N- and C-termini of peptides. Another way of increasing immunogenicity is by amino acid substitutions to either enhance Major Histocompatibility Complex (MHC) binding by modifying anchor residues ("fixed anchor epitopes"), or enhance binding to the T cell receptor (TCR) by modifying TCR interaction sites ("heteroclitic epitopes") (see, e.g., Sette and Fikes, Current Opinion in Immunology, 2003, 15:461-5470). In some embodiments, the epitopes described herein can be modified at one, two, three, four, five, or six positions. Even non-immunogenic or low affinity peptides can be made immunogenic by modifying their sequence to introduce a tyrosine in the first position (see, e.g., Tourdot et al., Eur. J lmmunol., 2000, 30:3411-3421).

The peptides can also include internal mutations that render them "superantigens" or "superagonists" for T cell stimulation. Superantigen peptides can be generated by screening T cells with a positional scanning synthetic peptide combinatorial library (PS-CSL) as described in Pinilla et al., Biotechniques, 13(6):901-5, 1992; Borras et al., J. Immunol. Methods, 267(1):79-97, 2002; U.S. Publication No. 2004/0072246; and Lustgarten et al., J. Immun. 176: 1796-1805, 2006. In some embodiments, a superagonist peptide is a peptide shown in Table 2, above, with one, two, three, or four amino acid substitutions which render the peptide a more potent immunogen.

Antigenic peptides can be obtained by chemical synthesis using a commercially available automated peptide synthesizer. Chemically synthesized peptides can be precipitated and further purified, for example by high performance liquid chromatography (HPLC). Alternatively, the peptides can be obtained by recombinant methods using host cell and vector expression systems. "Synthetic peptides" includes peptides obtained by chemical synthesis in vitro as well as peptides obtained by recombinant expression. When tumor antigen peptides are obtained synthetically, they can be incubated with antigen presenting cells in higher concentrations (e.g., higher concentrations than would be present in a tumor antigen cell lysates, which includes an abundance of peptides from non-immunogenic, normal cellular proteins). This permits higher levels of MHC-mediated presentation of the tumor antigen peptide of interest and induction of a more potent and specific immune response, and one less likely to cause undesirable autoimmune reactivity against healthy non-cancerous cells.

Multipeptide Vaccines

In formulating a multipeptide vaccine it is not only important to identify and characterize tumor-associated antigens expressed on the cancer of interest, but also the combinations of different epitopes from the tumor-associated antigens that increase the likelihood of a response to more than one epitope for the patient. To counter the tumor's ability to evade therapies directed against it, the present disclosure utilizes a variety of specific peptides in the vaccine. Specifically, combinations or mixtures of at least one epitope of the following seven tumor-associated antigens are particularly useful for immunotherapeutic treatments: Mesothelin, NY-ESO-1, FBP, HER-2/neu, IL-13 receptor α2, MAGE-A1, and EphA2. The effectiveness of a multipeptide vaccine comprising epitopes of the above seven antigens can be further improved by including in such a multivalent vaccine at least one epitope from at least one, two, three, four, five, six, or seven of the following tumor-associated antigens: p53, k-Ras, Ep-CAM, MUC1, Survivin, hTERT, and WT1. More than one epitope from the same protein can be used in the multipeptide vaccine. For example, the vaccine may contain at least one, at least two, at least three, or at least four different epitopes from any of the fourteen tumor associated antigens listed above. In addition one or more epitopes from antigens other than the fourteen listed above can also be used (e.g., CT45, SP-17, SCP-1).

The multipeptide vaccines described herein encompass a mixture of isolated peptides comprising the following amino acid sequences: SLLFLLFSL (SEQ ID NO:15) with four or fewer, three or fewer, two or fewer, or one amino acid substitution(s) within SEQ ID NO:15, or VLPLTVAEV (SEQ ID NO:17) with four or fewer, three or fewer, two or fewer, or one amino acid substitution(s) within SEQ ID NO:17; SLLMWITQC (SEQ ID NO:26) with four or fewer, three or fewer, two or fewer, or one amino acid substitution(s) within SEQ ID NO:26; EIWTHSYKV (SEQ ID NO:28) with four or fewer, three or fewer, two or fewer, or one amino acid substitution(s) within SEQ ID NO:28; VMAGVGSPYV (SEQ ID NO:40) with four or fewer, three or fewer, two or fewer, or one amino acid substitution(s) within SEQ ID NO:40; WLPFGFILI (SEQ ID NO:49) with four or fewer, three or fewer, two or fewer, or one amino acid substitution(s) within SEQ ID NO:49; KVLEYVIKV (SEQ ID NO:55) with four or fewer, three or fewer, two or fewer, or one amino acid substitution(s) within SEQ ID NO:55; and TLADFDPRV (SEQ ID NO:66) with four or fewer, three or fewer, two or fewer, or one amino acid substitution(s) within SEQ ID NO:66.

Certain multipeptide vaccines described herein comprise a mixture of peptides corresponding to the following epitopes: SLLFLLFSL (SEQ ID NO:15) or VLPLTVAEV (SEQ ID NO:17) from Mesothelin; SLLMWITQC (SEQ ID NO:26) from NY-ESO-1; EIWTHSYKV (SEQ ID NO:28)

from FBP; VMAGVGSPYV (SEQ ID NO:40) from HER2/neu; WLPFGFILI (SEQ ID NO:49) from IL-13Rα2; KVLEYVIKV (SEQ ID NO:55) from MAGE-A1; and TLADFDPRV (SEQ ID NO:66) from EphA2.

The multipeptide vaccines of the present disclosure can contain mixtures of epitopes from HLA-A2 restricted epitopes alone; HLA-A2 restricted epitopes in combination with at least one HLA-A1 or HLA-A3 restricted epitope; HLA-A2 restricted epitopes in combination with at least one HLA-DR, HLA-DQ, and/or HLA-DP restricted epitope; or HLA-A2 restricted epitopes in combination with at least one HLA-A1 or HLA-A3 restricted epitope and at least one HLA-DR, HLA-DQ, and/or HLA-DP restricted epitope. The MHC class I and MHC class II epitopes can be from the same antigen or different antigens.

For the treatment of gynecological cancers (e.g., ovarian, fallopian tube) or peritoneal cancer, the multipeptide vaccine can comprise at least one epitope from the following seven antigens: Mesothelin, NY-ESO-1, FBP, HER-2/neu, IL-13 receptor α2, MAGE-A1, and EphA2. For example, a multipeptide vaccine for use in treating a gynecological or peritoneal cancer can comprise the following HLA-A2 restricted epitope peptides: SLLFLLFSL (SEQ ID NO:15) or VLPLTVAEV (SEQ ID NO:17) from Mesothelin; SLLMWITQC (SEQ ID NO:26) from NY-ESO-1; EIWTHSYKV (SEQ ID NO:28) from FBP; VMAGVGSPYV (SEQ ID NO:40) from HER2/neu; WLPFGFILI (SEQ ID NO:49) from IL-13Rα2; KVLEYVIKV (SEQ ID NO:55) from MAGE-A1; and TLADFDPRV (SEQ ID NO:66) from EphA2. The vaccine can also include at least one HLA-A1 restricted epitope sequences such as EADPTGHSY (SEQ ID NO:127) (MAGE-A1 epitope) and/or at least one HLA-A3 restricted epitope sequences such as SLFRAVITK (SEQ ID NO:128) (MAGE-A1 epitope) and VLRENTSPK (SEQ ID NO:129) (Her-2/neu epitope). A vaccine for use in treating ovarian, fallopian tube, or peritoneal cancer can further include at least one MHC class II epitopes (e.g., AKFVAAWTLKAAA (SEQ ID NO:130), the pan-DR epitope (PADRE); AQYIKANSKFIGITEL (SEQ ID NO:131), a modified tetanus toxoid peptide). In addition, a vaccine for the treatment of gynecological cancers (e.g., ovarian, fallopian tube) or peritoneal cancer can also include one or more epitopes (class I (e.g., HLA-A2) and/or class II) from at least one, two, three, four, five, six, or seven of the following tumor-associated antigens: p53, k-Ras, Ep-CAM, MUC1, Survivin, hTERT, and WT1.

The multipeptide mixture can be administered with adjuvants to render the composition more immunogenic. Adjuvants include, but are not limited to, Freund's adjuvant, GM-CSF, Montanide (e.g., Montanide IMS 1312, Montanide ISA 206, Montanide ISA 50V, and Montanide ISA-51), 1018 ISS, aluminium salts, Amplivax®, AS15, BCG, CP-870,893, CpG7909, CyaA, dSLIM, flagellin or TLR5 ligands derived from flagellin, FLT3 ligand, IC30, IC31, Imiquimod (ALDARA®), resiquimod, ImuFact IMP321, Interleukins such as IL-2, IL-4, IL-7, IL-12, IL-13, IL-15, IL-21, IL-23, Interferon-α or -β, or pegylated derivatives thereof, IS Patch, ISS, ISCOMATRIX, ISCOMs, JuvImmune, LipoVac, MALP2, MF59, monophosphoryl lipid A, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, virosomes and other virus-like particles, YF-17D, VEGF trap, R848, beta-glucan, Pam3Cys, Aquila's QS21 stimulon, mycobacterial extracts and synthetic bacterial cell wall mimics, Ribi's Detox, Quil, Superfos, cyclophosphamide, sunitinib, bevacizumab, celebrex, NCX-4016, sildenafil, tadalafil, vardenafil, sorafenib, temozolomide, temsirolimus, XL-999, CP-547632, pazopanib, VEGF Trap, ZD2171, AZD2171, and anti-CTLA4 antibodies. CpG immunostimulatory oligonucleotides can be used to enhance the effects of adjuvants in a vaccine setting. In one embodiment, the multipeptide vaccine is administered with Montanide ISA-51 and/or GM-CSF.

The multipeptide compositions of the present disclosure can be administered parenterally (e.g., subcutaneous, intradermal, intramuscular, intraperitoneal) or orally. The peptides and optionally other molecules (e.g., adjuvants) can be dissolved or suspended in a pharmaceutically acceptable carrier. In addition, the multipeptide compositions of the present disclosure can contain buffers and/or excipients. The peptides can also be administered together with immune stimulating substances, such as cytokines.

The peptides for use in the vaccine can be synthesized, for example, by using the Fmoc-polyamide mode of solid-phase peptide synthesis which is disclosed by Lu et al (1981) J. Org. Chem. 46, 3433 and the references therein. The peptides described herein can be purified by any one, or a combination of, techniques such as recrystallization, size exclusion chromatography, ion-exchange chromatography, hydrophobic interaction chromatography, and reverse-phase high performance liquid chromatography using e.g. acetonitrile/water gradient separation. Analysis of peptides can be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

The peptides disclosed herein can have additional N- and/or C-terminally located stretches of amino acids that do not necessarily form part of the peptide that functions as the actual epitope for MHC molecules but can, nevertheless, be important for efficient introduction of the peptide into cells. The peptides described herein can also be modified to improve stability and/or binding to MHC molecules to elicit a stronger immune response. Methods for such an optimization of a peptide sequence are well known in the art and include, for example, the introduction of reverse peptide bonds or non-peptide bonds. Peptides comprising the sequences described herein can be synthesized with additional chemical groups present at their amino and/or carboxy termini, to enhance, for example, the stability, bioavailability, and/or affinity of the peptides. For example, hydrophobic groups such as carbobenzoxyl, dansyl, t-butyloxycarbonyl, acetyl, or a 9-fluorenylmethoxy-carbonyl group can be added to the peptides' amino terminus. Additionally, hydrophobic, t-butyloxycarbonyl, or amido groups can be added to the peptides' carboxy terminus. Further, all peptides described herein can be synthesized to alter their steric configuration. For example, the D-isomer of one or more of the amino acid residues of the peptides can be used, rather than the usual L-isomer. Still further, at least one of the amino acid residues of the peptides can be substituted by one of the well-known, non-naturally occurring amino acid residues. Alterations such as these can serve to increase the stability, bioavailability and/or binding action of the peptides of the disclosure. The peptides described herein can also be modified with polyethyleneglycol (PEG) and other polymers to extend their half-lives.

Once each peptide is prepared, it can be solubilized, sterile-filtered, and either stored by itself or mixed with the other peptides of the multipeptide vaccine and stored, at low temperatures (e.g., −80° C.) and protected from light.

Preparation of Antigen Presenting Cells

Antigen-presenting cells (APCs) are cells that display antigens complexed with major histocompatibility complex (WIC) proteins on their surfaces. T cells cannot recognize, and therefore do not react to, "free" antigen. APCs process antigens and present them to T cells. T cells may recognize these complexes using their T-cell receptors (TCRs). Examples of APCs include dendritic cells, macrophages, B cells, and certain activated epithelial cells. Dendritic cells (DCs) include myeloid dendritic cells and plasmacytoid dendritic cells. APCs, suitable for administration to subjects (e.g., cancer patients), can be isolated or obtained from any tissue in which such cells are found, or can be otherwise cultured and provided.

APCs (e.g., DCs) can be found, by way of example, in the bone marrow or PBMCs of a mammal, in the spleen of a mammal, or in the skin of a mammal (i.e., Langerhans cells, which possess certain qualities similar to that of DC, may be found in the skin). For example, bone marrow can be harvested from a mammal and cultured in a medium that promotes the growth of DC. GM-CSF, IL-4 and/or other cytokines (e.g., TNF-α), growth factors and supplements can be included in this medium. After a suitable amount of time in culture in medium containing appropriate cytokines (e.g., suitable to expand and differentiate the DCs into mature DCs, e.g., 4, 6, 8, 10, 12, or 14 days), clusters of DC are cultured in the presence of epitopes of antigens of interest (e.g., in the presence of a mixture of at least one epitope from: mesothelin, NY-ESO-1, FBP, HER-2/neu, IL-13 receptor α2, MAGE-A1, EphA2; and optionally, epitopes from at least one, at least two, at least three, at least four, at least five, at least six, or at least seven of the following antigens: p53, k-Ras, Ep-CAM, MUC1, Survivin, hTERT and WT1) and harvested for use in a cancer vaccine using standard techniques.

The epitopes used for culturing with the APCs will depend on the type of cancer. For example, for treatment of gynecological (e.g., ovarian or fallopian tube cancers) or peritoneal cancer, one can choose at least one epitope (e.g., HLA-A2 epitope) from the following antigens: mesothelin, NY-ESO-1, FBP, HER-2/neu, IL-13 receptor α2, MAGE-A1, and EphA2. For example, the epitopes comprise: SLLFLLFSL (SEQ ID NO:15) with four or fewer, three or fewer, two or fewer, or one amino acid substitution(s) within SEQ ID NO:15, or VLPLTVAEV (SEQ ID NO:17) with four or fewer, three or fewer, two or fewer, or one amino acid substitution(s) within SEQ ID NO:17; SLLMWITQC (SEQ ID NO:26) with four or fewer, three or fewer, two or fewer, or one amino acid substitution(s) within SEQ ID NO:26; EIWTHSYKV (SEQ ID NO:28) with four or fewer, three or fewer, two or fewer, or one amino acid substitution(s) within SEQ ID NO:28; VMAGVGSPYV (SEQ ID NO:40) with four or fewer, three or fewer, two or fewer, or one amino acid substitution(s) within SEQ ID NO:40; WLPFGFILI (SEQ ID NO:49) with four or fewer, three or fewer, two or fewer, or one amino acid substitution(s) within SEQ ID NO:49; KVLEYVIKV (SEQ ID NO:55) with four or fewer, three or fewer, two or fewer, or one amino acid substitution(s) within SEQ ID NO:55; and TLADFDPRV (SEQ ID NO:66) with four or fewer, three or fewer, two or fewer, or one amino acid substitution(s) within SEQ ID NO:66. In another embodiment, the epitopes comprise: SLLFLLFSL (SEQ ID NO:15) or VLPLTVAEV (SEQ ID NO:17) from Mesothelin; SLL-MWITQC (SEQ ID NO:26) from NY-ESO-1; EIWTHSYKV (SEQ ID NO:28) from FBP; VMAGVGSPYV (SEQ ID NO:40) from HER2/neu; WLPFGFILI (SEQ ID NO:49) from IL-13Rα2; KVLEY-VIKV (SEQ ID NO:55) from MAGE-A1; and TLADFDPRV (SEQ ID NO:66) from EphA2. Optionally, one could also include epitopes from at least one, at least two, at least three, at least four, at least five, at least six, or at least seven, of the following antigens: p53, k-Ras, Ep-CAM, MUC1, Survivin, hTERT and WT1. In certain embodiments, the epitope that is used is an HLA-A2 epitope. In addition to the HLA-A2 epitopes, the APCs can also be expanded in the presence of MHC class II epitopes and/or other HLA epitopes (e.g., HLA-A1 and/or HLA-A3). Epitopes of the antigens (e.g., isolated, purified peptides, or synthetic peptides) can be added to cultures at a concentration of 1 µg/ml-50 µg/ml per epitope, e.g., 2, 5, 10, 15, 20, 25, 30, or 40 µg/ml per epitope. Subject-specific APC vaccines (e.g., DC vaccines) are produced, carefully labeled, and stored. Single doses of the peptide-loaded (e.g., 1 to $50 \times 10^6$ cells) APCs (e.g., DCs) can be cryopreserved in human serum albumin containing 10% dimethyl sulphoxide (DMSO) or in any other suitable medium for future use. In one embodiment, the APC-based vaccine is the Exemplary Vaccine 1 (a DC vaccine) disclosed in Example 4.

In one exemplary method of preparing APC (e.g., DC), the APC are isolated from a subject (e.g., a human) according to the following procedure. Mononuclear cells are isolated from blood using leukapheresis (e.g., using a COBE Spectra Apheresis System). The mononuclear cells are allowed to become adherent by incubation in tissue culture flasks for 2 hours at 37° C. Nonadherent cells are removed by washing. Adherent cells are cultured in medium supplemented with granulocyte macrophage colony stimulating factor (GM-CSF) (800 units/ml, clinical grade, Immunex, Seattle, Wash.) and interleukin-4 (IL-4)(500 units/ml, R&D Systems, Minneapolis, Minn.) for five days. On day five, TNF-α is added to the culture medium for another 3-4 days. On day 8 or 9, cells are harvested and washed, and incubated with peptide antigens for 16-20 hours on a tissue rotator. In one embodiment, the epitopes comprise: SLLFLLFSL (SEQ ID NO:15) with four or fewer, three or fewer, two or fewer, or one amino acid substitution(s) within SEQ ID NO:15, or VLPLTVAEV (SEQ ID NO:17) with four or fewer, three or fewer, two or fewer, or one amino acid substitution(s) within SEQ ID NO:17; SLLMWITQC (SEQ ID NO:26) with four or fewer, three or fewer, two or fewer, or one amino acid substitution(s) within SEQ ID NO:26; EIWTHSYKV (SEQ ID NO:28) with four or fewer, three or fewer, two or fewer, or one amino acid substitution(s) within SEQ ID NO:28; VMAGVGSPYV (SEQ ID NO:40) with four or fewer, three or fewer, two or fewer, or one amino acid substitution(s) within SEQ ID NO:40; WLPFGFILI (SEQ ID NO:49) with four or fewer, three or fewer, two or fewer, or one amino acid substitution(s) within SEQ ID NO:49; KVLEYVIKV (SEQ ID NO:55) with four or fewer, three or fewer, two or fewer, or one amino acid substitution(s) within SEQ ID NO:55; and TLADFDPRV (SEQ ID NO:66) with four or fewer, three or fewer, two or fewer, or one amino acid substitution(s) within SEQ ID NO:66. In another embodiment, the epitopes comprise: SLLFLLFSL (SEQ ID NO:15) or VLPLTVAEV (SEQ ID NO:17) from Mesothelin; SLLMWITQC (SEQ ID NO:26) from NY-ESO-1; EIWTHSYKV (SEQ ID NO:28) from FBP; VMAGVGSPYV (SEQ ID NO:40) from HER2/neu; WLPFGFILI (SEQ ID NO:49) from IL-13Rα2; KVLEYVIKV (SEQ ID NO:55) from MAGE-A1; and TLADFDPRV (SEQ ID NO:66) from EphA2. Peptide antigens are added to the cultures at a concentration of about 10 µg/ml to about 20 µg/ml per epitope.

Various other methods can be used to isolate the APCs, as would be recognized by one of skill in the art. DCs occur in low numbers in all tissues in which they reside, making isolation and enrichment of DCs a requirement. Any of a number of procedures entailing repetitive density gradient separation, fluorescence activated cell sorting techniques, positive selection, negative selection, or a combination thereof, are routinely used to obtain enriched populations of isolated DCs. Guidance on such methods for isolating DCs can be found, for example, in O'Doherty et al., J. Exp. Med., 178: 1067-1078, 1993; Young and Steinman, J. Exp. Med., 171: 1315-1332, 1990; Freudenthal and Steinman, Proc. Nat. Acad. Sci. USA, 57: 7698-7702, 1990; Macatonia et al., Immunol., 67: 285-289, 1989; Markowicz and Engleman, J. Clin. Invest., 85: 955-961, 1990; Mehta-Damani et al., J. Immunol., 153: 996-1003, 1994; and Thomas et al., J. Immunol., 151: 6840-6852, 1993. One method for isolating DCs from human peripheral blood is described in U.S. Pat. No. 5,643,786.

The DCs prepared according to methods described herein present epitopes corresponding to the antigens at a higher average density than epitopes present on dendritic cells exposed to a tumor lysate (e.g., an ovarian cancer lysate). The relative density of one or more antigens on antigen presenting cells can be determined by both indirect and direct means. The primary immune response of naïve animals is roughly proportional to the antigen density of antigen presenting cells (Bullock et al., J. Immunol., 170: 1822-1829, 2003). Relative antigen density between two populations of antigen presenting cells can therefore be estimated by immunizing an animal with each population, isolating B or T cells, and monitoring the specific immune response against the specific antigen by, e.g., tetramer assays, ELISPOT, or quantitative PCR.

Relative antigen density can also be measured directly. In one method, the antigen presenting cells are stained with an antibody that binds specifically to the MHC-antigen complex, and the cells are then analyzed to determine the relative amount of antibody binding to each cell (see, e.g., Gonzalez et al., Proc. Natl. Acad. Sci. USA, 102:4824-4829, 2005). Exemplary methods to analyze antibody binding include flow cytometry and fluorescence activated cell sorting. The results of the analysis can be reported e.g., as the proportion of cells that are positive for staining for an individual MHC-antigen complex or the average relative amount of staining per cell. In some embodiments, a histogram of relative amount of staining per cell can be created.

In some embodiments, antigen density can be measured directly by direct analysis of the peptides bound to MHC, e.g., by mass spectrometry (see, e.g., Purcell and Gorman, Mol. Cell. Proteomics, 3:193-208, 2004). Typically, MHC-bound peptides are isolated by one of several methods. In one method, cell lysates of antigen presenting cells are analyzed, often following ultrafiltration to enrich for small peptides (see, e.g., Falk et al., J. Exp. Med., 174:425-434, 1991; Rotzxhke et al., Nature, 348:252-254, 1990). In another method, MHC-bound peptides are isolated directly from the cell surface, e.g., by acid elution (see, e.g., Storkus et al., J. Immunother., 14:94-103, 1993; Storkus et al., J. Immunol., 151:3719-27, 1993). In another method, MHC-peptide complexes are immunoaffinity purified from antigen presenting cell lysates, and the MHC-bound peptides are then eluted by acid treatment (see, e.g., Falk et al., Nature, 351:290-296). Following isolation of MHC-bound peptides, the peptides are then analyzed by mass spectrometry, often following a separation step (e.g., liquid chromatography, capillary gel electrophoresis, or two-dimensional gel electrophoresis). The individual peptide antigens can be both identified and quantified using mass spectrometry to determine the relative average proportion of each antigen in a population of antigen presenting cells. In some methods, the relative amounts of a peptide in two populations of antigen presenting cells are compared using stable isotope labeling of one population, followed by mass spectrometry (see, e.g., Lemmel et al., Nat. Biotechnol., 22:450-454, 2004).

Administration of Antigen Presenting Cell-Based Vaccine

The APC-based vaccine can be delivered to a patient (e.g., a patient having a gynecological cancer or a peritoneal cancer) or test animal by any suitable delivery route, which can include injection, infusion, inoculation, direct surgical delivery, or any combination thereof. In some embodiments, the cancer vaccine is administered to a human in the deltoid region or axillary region. For example, the vaccine is administered into the axillary region as an intradermal injection. In other embodiments, the vaccine is administered intravenously.

An appropriate carrier for administering the cells can be selected by one of skill in the art by routine techniques. For example, the pharmaceutical carrier can be a buffered saline solution, e.g., cell culture media, and can include DMSO for preserving cell viability. In certain embodiments, the cells are administered in an infusible cryopreservation medium. The composition comprising the cells can include DMSO and hetastarch as cryoprotectants, Plasmalyte A and/or dextrose solutions and human serum albumin as a protein component.

The quantity of APC appropriate for administration to a patient as a cancer vaccine to effect the methods described herein and the most convenient route of such administration are based upon a variety of factors, as can the formulation of the vaccine itself. Some of these factors include the physical characteristics of the patient (e.g., age, weight, and sex), the physical characteristics of the tumor (e.g., location, size, rate of growth, and accessibility), and the extent to which other therapeutic methodologies (e.g., chemotherapy, and beam radiation therapy) are being implemented in connection with an overall treatment regimen. Notwithstanding the variety of factors one should consider in implementing the methods of the present disclosure to treat a disease condition, a mammal can be administered with from about $10^5$ to about $10^8$ APC (e.g., 10' APC) in from about 0.05 mL to about 2 mL solution (e.g., saline) in a single administration. Additional administrations can be carried out, depending upon the above-described and other factors, such as the severity of tumor pathology. In one embodiment, from about one to about five administrations of about $10^6$ APC is performed at two-week intervals.

DC vaccination can be accompanied by other treatments. For example, a patient receiving DC vaccination can also be receiving chemotherapy, radiation, and/or surgical therapy before, concurrently, or after DC vaccination. Chemotherapy is used to shrink and slow cancer growth. Chemotherapy is recommended for most women having gynecological (e.g., ovarian cancer and fallopian tube cancer) or peritoneal cancer after the initial surgery for cancer; however, sometimes chemotherapy is given to shrink the cancer before surgery. The number of cycles of chemotherapy treatment depends on the stage of the disease. Chemotherapy may neutralize antitumor immune response generated through vaccine therapy. In addition, chemotherapy can be combined safely with immunotherapy, with possibly additive or synergistic effects, as long as combinations are designed rationally. Examples of chemotherapeutic agents that can be used in treatments of patients with gynecological (e.g., ovarian, fallopian tube cancers) or peritoneal cancers include, but are not limited to, carboplatin, cisplatin, cyclophosphamide, docetaxel, doxorubicin, etoposide, gemcitabine, oxaliplatin, paclitaxel, TAXOL™, topotecan, and vinorelbine. In one embodiment, a patient is treated with cyclophosphamide (intravenously 200 mg/kg) prior to APC (e.g., DC) vaccination. For example, a patient can be intravenously injected with cyclophosphasmide (200 mg/kg) one day before, or between 24 hours and one hour before, APC (e.g., DC) vaccination. Cyclophosphamide is an alkylating drug that is used for treating several types of cancer. Cyclophosphamide is an inactive pro-drug; it is converted and activated by the liver into two chemicals, acrolein and phosphoramide. Acrolein and phosphoramide are the active compounds, and they slow the growth of cancer cells by interfering with the actions of deoxyribonucleic acid (DNA) within the cancerous cells. Cyclophosphamide is, therefore, referred to as a cytotoxic drug. Methods of treating cancer using DC vaccination in conjunction with chemotherapy are described, e.g., in Wheeler et al., U.S. Pat. No. 7,939,090. In some embodiments, a patient receiving DC vaccination has already received chemotherapy, radiation, and/or surgical treatment for the gynecological or peritoneal cancer.

In addition to, or separate from chemotherapeutic treatment, a patient receiving DC vaccination can be treated with any other treatments that are beneficial for gynecological or peritoneal cancer. For example, a patient (e.g., one having ovarian, fallopian tube or peritoneal cancer) can be treated prior to, concurrently, or after DC vaccination with a COX-2 inhibitor, as described, e.g., in Yu and Akasaki, WO 2005/037995. In another embodiment, a patient receiving DC vaccination can be treated with bevacizumab (Avastin®) prior to, concurrently, or after DC vaccination.

Immunological Testing

The antigen-specific cellular immune responses of vaccinated subjects can be monitored by a number of different assays, such as tetramer assays and ELISPOT. The following sections provide examples of protocols for detecting responses with these techniques. Additional methods and protocols are available. See e.g., Current Protocols in Immunology, Coligan, J. et al., Eds., (John Wiley & Sons, Inc.; New York, N.Y.).

Tetramer Assay

Tetramers comprised of recombinant MHC molecules complexed with a peptide can be used to identify populations of antigen-specific T cells. To detect T cells specific for antigens such as HER-2, FBP and mesothelin, fluorochrome labeled specific peptide tetramer complexes (e.g., phycoerythrin (PE)-tHLA) containing peptides from these antigens can be synthesized and provided by Beckman Coulter (San Diego, Calif.). Specific CTL clone CD8 cells can be resuspended in a buffer, e.g., at $10^5$ cells/50 µl FACS buffer (phosphate buffer plus 1% inactivated FCS buffer). Cells can be incubated with 1 µl tHLA for a sufficient time, e.g., for 30 minutes at room temperature, and incubation can be continued for an additional time, e.g., 30 minutes at 4° C. with $10_11.1$ anti-CD8 mAb (Becton Dickinson, San Jose, Calif.). Cells can be washed twice, e.g., in 2 ml cold FACS buffer, before analysis by FACS (Becton Dickinson).

ELISPOT Assay

ELISPOT assays can be used to detect cytokine secreting cells, e.g., to determine whether cells in a vaccinated patient secrete cytokine in response to antigen, thereby demonstrating whether antigen-specific responses have been elicited. ELISPOT assay kits are supplied, e.g., from R & D Systems (Minneapolis, Minn.) and can be performed as described by the manufacturer's instructions.

Responder (R) $1 \times 10^5$ patients' PBMC cells from before and after vaccination are plated in 96-well plates with nitrocellulose membrane inserts coated with capture Ab. Stimulator (S) cells (TAP-deficient T2 cells pulsed with antigen) are added at the R: S ratio of 1:1. After a 24-hour incubation, cells are removed by washing the plates 4 times. The detection Ab is added to each well. The plates are incubated at 4° C. overnight and the washing steps will be repeated. After a 2-hour incubation with streptavidin-AP, the plates are washed. Aliquots (100 µl) of BCIP/NBT chromogen are added to each well to develop the spots. The reaction is stopped, e.g., after 60 minutes, e.g., by washing with water. The spots can be scanned and counted with a computer-assisted image analysis (Cellular Technology Ltd, Cleveland, Ohio). When experimental values are significantly different from the mean number of spots against non-pulsed T2 cells (background values), as determined by a two-tailed Wilcoxon rank sum test, the background values can be subtracted from the experimental values.

In vitro Induction of CTL in Patient-Derived PBMCs

The following protocol can be used to produce antigen specific CTL in vitro from patient-derived PBMC. To generate dendritic cells, the plastic adherent cells from PBMCs can be cultured in AIM-V® medium supplemented with recombinant human GM-CSF and recombinant human IL-4 at 37° C. in a humidified $CO_2$ (5%) incubator. Six days later, the immature dendritic cells in the cultures can be stimulated with recombinant human TNF-α for maturation. Mature dendritic cells can then be harvested on day 8, resuspended in PBS at $1 \times 10^6$ per mL with peptide (2 µg/mL), and incubated for 2 hours at 37° C. Autologous CD8+ T cells can be enriched from PBMCs using magnetic microbeads (Miltenyi Biotech, Auburn, Calif.). CD8+ T cells ($2 \times 10^6$ per well) can be co-cultured with $2 \times 10^5$ per well peptide-pulsed dendritic cells in 2 mL/well of AIM-V® medium supplemented with 5% human AB serum and 10 units/mL rhIL-7 (Cell Sciences) in each well of 24-well tissue culture plates. About 20 U/ml of IL-2 can be added 24 h later at regular intervals, 2 days after each restimulation.

On day 7, lymphocytes can be restimulated with autologous dendritic cells pulsed with peptide in AIM-V® medium supplemented with 5% human AB serum, rhIL-2, and rhIL-7 (10 units/mL each). About 20 U/ml of IL-2 can be added 24 h later at regular intervals, 2 days after each restimulation. On the seventh day, after the three rounds of restimulation, cells can be harvested and tested the activity of CTL. The stimulated CD8+ cultured cells (CTL) can be co-cultured with T2 cells (a human TAP-deficient cell line) pulsed with 2 µg/ml Her-2, FBP, mesothelin or IL13 receptor α2 peptides. After 24 hours incubation, IFN-γ in the medium can be measured by ELISA assay.

Pharmaceutical Compositions

In various embodiments, the present disclosure provides pharmaceutical compositions, e.g., including a pharmaceutically acceptable carrier along with a therapeutically effective amount of the vaccines described herein that include multipeptide vaccines and dendritic cells loaded with the antigens described herein. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier can be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it can come in contact, meaning that it must not carry a risk of toxicity, irritation, allergic response, immunogenicity, or any other complication that excessively outweighs its therapeutic benefits.

In various embodiments, the pharmaceutical compositions described herein can be formulated for delivery via any route of administration. "Route of administration" can refer to any administration pathway, whether or not presently known in the art, including, but not limited to, aerosol, nasal, transmucosal, transdermal, or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions can be in the form of solutions or suspensions for infusion or for injection, or as lyophilized powders.

The pharmaceutical compositions described herein can be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 21st edition, Williams & Wilkins Pa., USA) (2005). In one embodiment, a therapeutically effective amount of the vaccine can comprise about $10^6$ to about $10^8$ tumor antigen-pulsed DC (e.g., $10^6$, $0.5 \times 10^7$, $10^7$, $0.5 \times 10^8$, $10^8$). In some embodiments, a therapeutically effective amount is an amount sufficient to reduce or halt tumor growth, and/or to increase survival of a patient.

Kits

The present disclosure is also directed to kits to treat cancers (e.g., ovarian cancer, peritoneal cancer). The kits are useful for practicing the inventive method of treating cancer with a vaccine comprising dendritic cells loaded with the antigens or multipeptide vaccines as described herein. The kit is an assemblage of materials or components, including at least one of the compositions described herein. Thus, in some embodiments, the kit includes a set of peptides for preparing cells for vaccination. The kit can also include agents for preparing cells (e.g., cytokines for inducing differentiation of DC in vitro). The disclosure also provides kits containing a composition including a vaccine comprising dendritic cells (e.g., cryopreserved dendritic cells) loaded with the antigens as described herein.

The exact nature of the components configured in the kits described herein depends on their intended purpose. For example, some embodiments are configured for the purpose of treating ovarian cancers. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Optionally, the kit also contains other useful components, such as, diluents, buffers, pharmaceutically acceptable carriers, syringes, catheters, applicators, pipetting or measuring tools, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in cancer treatments or in vaccinations. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing for example, a vaccine comprising dendritic cells loaded with epitopes from the antigens as described herein. The packaging material generally has an external label which indicates the contents and/or purpose of the kit and/or its components.

EXAMPLES

The following examples are provided to better illustrate the claimed disclosure and are not to be interpreted as limiting the scope of the disclosure. To the extent that specific materials are mentioned, it is merely for purposes of illustration and is not intended to limit the disclosure. One skilled in the art can develop equivalent means or reactants without the exercise of inventive capacity and without departing from the scope of the disclosure.

Example 1

Summary of Overall Study Design

This study is conducted in agreement with the directives and guidelines of the Declaration of Helsinki and the International Conference on Harmonization Guidance for Industry on Good Clinical Practice Consolidated Guidance (ICH GCP-E6).

Before initiation of the study, the Protocol and the patient informed consent form (ICF) is submitted for review and approval to an Institutional Review Board (IRB).

Patients with histologically confirmed FIGO stage III or IV epithelial ovarian cancer (EOC), primary peritoneal cancer (PPC), or fallopian tube carcinoma (FTC) who have no evidence of disease (NED) by CT or PET/CT and are in remission are screened for selecting subjects for treatment with an autologous vaccine (Exemplary Vaccine 1) consisting of the patient's DCs pulsed with synthetic MHC class I epitope peptides from seven tumor stem cell associated antigens (i.e., Mesothelin, NY-ESO-1, FBP, Her2/neu, IL13Rα2, MAGE-A1, and EphA2).

The screening inclusion and exclusion criteria for this study are listed below.

Screening Inclusion Criteria:
1. Subject must understand and sign the study specific informed consent
2. Subject must be currently in clinical remission by clinical and radiological criteria (RECIST 1.1 criteria). [>15 weeks should have elapsed for subjects in primary remission and >12 weeks for those who are in secondary remission]
3. Presence of ascites or pleural effusions are not exclusionary if these are asymptomatic and do not have positive cytology
4. ECOG performance status of 0 or 1
5. Life expectancy >6 months
6. HLA-A2 positivity
7. Adequate renal, hepatic and bone marrow function based on screening laboratory assessments. Baseline hematologic studies and chemistry profiles must meet the following criteria:
   a) hemoglobin (Hgb) >9.9 g/dL
   b) hematocrit >30%
   c) absolute neutrophil count (ANC) >1000/mm$^3$
   d) platelet count >100,000/mm$^3$
   e) blood urea nitrogen (BUN) <30 mg/dL
   f) creatinine <2 mg/dL
   g) alkaline phosphatase (ALP), aspartate aminotransferase (AST) and alanine aminotransferase (ALT) <4× upper limit of normal (ULN)
   h) prothrombin time (PT) and activated partial thromboplastin time (PTT) <1.6× unless therapeutically warranted
8. Written informed consent, Release of Medical Records Form and Health Insurance Portability and Accountability Act (HIPAA) reviewed and signed by patient or legally authorized representatives.

Screening Exclusion Criteria:
1. Subjects with any evidence of metastases as confirmed by imaging.
2. Subjects receiving investigational study drug for any indication or immunological-based treatment for any reason
3. Subjects with concurrent conditions that would jeopardize the safety of the subject or compliance with the protocol
4. Subject has a chronic or acute hepatitis C or B infection
5. Subject has positive test result at the screening visit for one or more of the following: HTLV-1/2 and/or Anti-HIV 1 Antibody (α-HIV-1)
6. Subject requires or is likely to require more than a two-week course of corticosteroids for intercurrent illness. Subject must complete the course of corticosteroids 2 weeks before screening to meet eligibility.
7. Subject has renal insufficiency as defined by a serum creatinine >2.0 mg/dl or BUN >30 mg/dl. Note: If creatinine is greater than 1.5×ULN, creatinine clearance must be greater than 60 ml/min.
8. Subject with liver failure as defined by a serum total bilirubin >2.0 and/or serum transaminases >3× the upper limits of normal.
9. Subject has hematopoietic failure at baseline as defined by one of the following:
   Platelets <100,000/mm$^3$
   WBC <2,500/mm$^3$
   Absolute Neutrophil Count (ANC) <1,000/mm$^3$
   Absolute lymphocyte count <200/mm$^3$
   Hematocrit <30%
10. Subject has an acute infection requiring active treatment with antibiotics/antivirals; Acute therapy must have been completed within seven days prior to study enrollment.
11. Subject is receiving medication(s) that might affect immune function. Use of H2 antagonists are prohibited as are all antihistamines five days before and five days after each injection of study vaccine. However, NSAIDS including COX-2 inhibitors, acetaminophen or aspirin are permitted.

After signing informed consent and completion of screening procedures, patients undergo ~10-15 liter apheresis on day −30 to −15 at the study site to isolate peripheral blood mononuclear cells (PBMCs) to be used for preparation of study treatment.

The apheresis product is used to prepare autologous dendritic cells which are then pulsed with epitopes from the seven synthetic tumor stem cell associated antigens. Subjects receive five doses of 5-10×10$^6$ autologous dendritic cells pulsed with epitopes from the seven synthetic tumor stem cell associated antigens intradermally on days 0, 21, 42, 63, and 84 and Cyclophosphamide 200 mg/m$^2$ the day before each vaccine. Subsequent induction vaccines are administered every three weeks during the Vaccine Induction Phase.

All subjects will have end of study (EOS) evaluation approximately 30 days following the fifth vaccine on day ~114. Subjects who remain "No Evidence of Disease" (NED) have the option to enter the enter the Maintenance Phase where they will have the option to undergo maintenance therapy continuing the treatments every 4 weeks until depletion of vaccine or confirmation of progressive disease (PD).

Treatment schedules and safety and efficacy assessments are the same for all patients. Safety will be monitored throughout the study.

The study duration is expected to be 20 to 24 months. The study duration for each patient is dependent on the amount of study treatment produced for the patient, disease progression, occurrence of unacceptable toxicities and time needed for apheresis and preparation of study treatment. After enrollment apheresis will take place. This is followed by Vaccine production. Patients then can enter the Vaccine Induction Phase. The optional maintenance vaccination will continue until depletion of study treatment or confirmation of PD, whichever comes first. The study will continue until all patients complete their end of study (EOS) assessments.

Subjects are contacted every 6 months for 5 years for survival. This follow up can be contact by phone or in writing and it begins after the last completed clinic visit.

Figure 11:
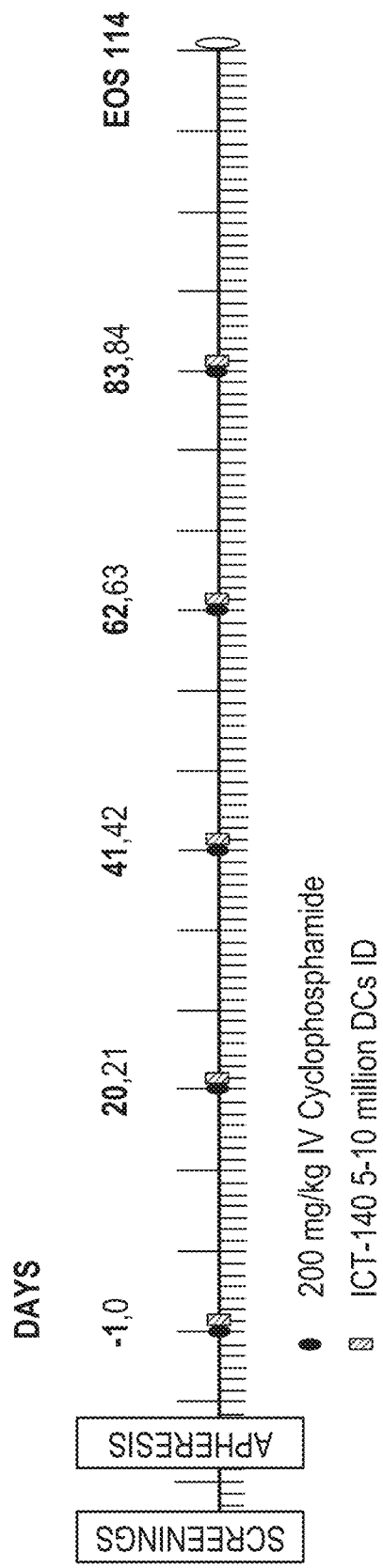
FIG. 11 is a schematic representation of a timeline of a Study.

A schematic representation of the timeline of the Study is depicted in FIG. 11.

Example 2

Preparation of Autologous Dendritic Cells (DC)

Human leukocyte antigen A2 (HLA-A2 or A2) positive patients with ovarian cancer, primary peritoneal cancer, or fallopian tube carcinoma are identified. Peripheral blood mononuclear cells (PBMCs) are isolated from such patients between days −30 to −15 using leukapheresis. The COBE Spectra Apheresis System is used to harvest the mononuclear cell layer. Leukapheresis yields about 10$^{10}$ peripheral blood mononuclear cells (PBMC). If these cells are not to be processed to prepare DCs shortly after they are harvested, the product is packaged in insulated led containers with temperature monitors to ensure that a temperature range of 2 18° C. is maintained.

For processing the PBMCs to prepare DCs, the PBMCs are allowed to become adherent for two hours at 37° C. in a tissue culture flask and washed in HB SS. PBMC are seeded at a density of $1.4 \times 10^6$ cells/cm$^2$ in 185-cm$^2$ culture flasks (Nunc, Roskilde, Denmark) and allowed to adhere for 2 h at 37° C. Non-adherent cells are removed by washing four times. Adherent cells are cultured in RPMI 1640 supplemented with GM-CSF (Berlex) and IL-4 (R&D systems) for 5 days. On day 5, 50 ng/ml clinical grade TNF-α (R&D systems) is added to the culture medium for another 3-4 days. On days 8-9, DCs are harvested and washed three times. The minimum number of DCs required to produce the study treatment is $7 \times 10^9$.

Example 3

Preparation of Vaccines

Dendritic cells, prepared as described in Example 2, are washed three times in dPBS, resuspended at 5-10×10$^6$ cells/ml in complete media and then co-incubated with tumor associated antigen peptides (20 µg/ml per antigen, reconstituted in 10% DMSO). The dendritic cells are incubated with the peptides at 37°/5% CO$_2$ for 16-20 hours on a tissue rotator to facilitate interaction.

After production, each DC preparation is tested for viability and microbial growth, and undergoes additional quality testing prior to freezing. A certificate of analysis will be produced for each batch (one certificate of analysis for each patient). The DC preparation is then frozen as follows: DC are resuspended in cryo tubes at various concentrations (1×10$^7$ cells per ml in autologous freezing medium (10% DMSO and 90% autologous serum), then immediately transferred to 2 ml cryo tubes (cryo tube vials, Nunc, Brand Products, Roskilde, Denmark), slowly frozen to −80° C. by using a cryo-freezing container (Nalgene cryo 1° C. freezing container, rate of cooling −1° C./min (Fisher Scientific, Calif.)) and finally transferred into the gas phase of liquid nitrogen until use.

The study treatments will be labeled in such a way to clearly identify the patient. It is imperative that only the patient's own (autologous) study treatment be administered to the same individual patient. For these reasons, the blood specimen is procured and handled according to a strict protocol to ensure optimal quality of the specimen and minimum transport time to and from the processing facility, as well as to ensure the unique identification of the specimen at all times including injection back into the patient.

Example 4

Exemplary Vaccine 1

Exemplary Vaccine 1 is an autologous vaccine consisting of the patient's own DCs pulsed with 20 µg/ml of at least seven of the synthetic peptides listed in Table 4 from the following tumor antigens: mesothelin, NY-ESO-1, FBP, Her2/neu, interleukin-13 receptor α2, MAGE-A1, and EphA2. Subject specific Exemplary Vaccine 1 will be produced for each subject.

TABLE 4

Tumor Antigen Peptides

| Antigen | HLA-A2 epitope |
|---|---|
| mesothelin | SLLFLLFSL (SEQ ID NO: 15) or VLPLTVAEV (SEQ ID NO: 17) |
| NY-ESO-1 | SLLMWITQC (SEQ ID NO: 26) |
| MAGE-1 | KVLEYVIKV (SEQ ID NO: 55) |
| FBP | EIWTHSYKV (SEQ ID NO: 28) |
| EphA2 | TLADFDPRV (SEQ ID NO: 66) |
| HER-2 | VMAGVGSPYV (SEQ ID NO: 40) |
| IL-13R α2 | WLPFGFILI (SEQ ID NO: 49) |

Exemplary Vaccine 1 is prepared and supplied as a solution for intradermal vaccine injection. The volume of Exemplary Vaccine 1 is 1 mL per vial; the volume administered to the patient is 1 mL. The concentration of pulsed dendritic cells in Exemplary Vaccine 1 is $1.1 \times 10^7$ cells/mL. The vaccine contains the following excipients: 31.25% Plasmalyte-A; 31.25% dextrose (5%)/0.45 NaCl; 7.5% DMSO; 1% dextran 40; and 5% human serum albumin. The vaccines are stored in liquid nitrogen storage or other climate led container capable of maintaining temperature at or below 130° C. and with adequate temperature monitoring until needed for use. The vaccine must be used within one hour of thawing It is to be understood that Exemplary Vaccine 1 may be administered with other HLA-A2 epitopes of the seven tumor antigens than those listed in Table 4. In addition, MHC class II epitopes can also be administered in combination with Exemplary Vaccine 1.

Example 5

Preparation of Study Vaccine

Preparation should not begin until it is confirmed that the patient is at the study site and ready to receive study treatment. Upon confirmation, a single study vaccine (2 mL cryovial) corresponding to the patient's autologous cells is thawed in a 37° C. sterile water bath. The study vaccine is loaded into a tuberculin syringe (27 g needle) and is used within one hour of thawing.

Example 6

Protocol for Administering the Vaccine

All patients receive cyclophosphasmide (intravenously 200 mg/kg) every 3 weeks, one day before each vaccination per institutional procedures.

Induction Vaccination (Vaccines 1 to 5):

Eligible patients will receive one intradermal injection of their patient-specific vaccine (Exemplary Vaccine 1) once every 3 weeks for 12 weeks during the Vaccine Induction Phase. Vaccination is given on days 1, 20, 41, 62, and 83.

Maintenance Vaccination (Vaccines 6 and above):

Subject may undergo maintenance vaccinations after end of study (EOS) assessment. During the maintenance vaccination phase subjects receive vaccinations monthly (every 4 weeks) until depletion of vaccine or confirmation of progressive disease (PD), whichever comes first.

Administration

Vaccines will be administered as intradermal injections in the groin region. Following administration of vaccine, the patient is observed for at least 60 minutes for potential reactions. Such reactions are assessed and recorded as adverse events (AEs), as appropriate.

Example 7

Immunological Testing

The patient's cellular antitumor response is assessed by a tetramer assay and enzyme-linked immunosorbent spot (ELISPOT) assay.

The tetramer assay will be used to assess responses to all peptides from: Mesothelin, NY-ESO-1, FBP, Her2/neu, IL13Ra2, MAGE-A1, and EphA2.

The first sample is taken from the apheresis product. For follow up samples (i.e., (every 3 weeks before each cyclophosphamide infusion and at EOS), approximately 80 mL blood samples is collected per time point and shipped to a central laboratory for analysis. Tetramer analysis, in vitro stimulation and ELISPOT will be done with tetramers and HLA peptides appropriate to the patient specific HLA type.

Example 8

Analysis of Expression of Tumor Antigens in Human Ovarian Tumor Samples

Objective: To utilize flow cytometry-based analysis for antigen profiling of primary human ovarian cancer cells to determine if Exemplary Vaccine 1 includes suitable candidate proteins for immunotherapeutic targeting.

Materials & Methods: Patients were entered into an Institutional Review Board-approved protocol and signed an informed consent prior to tissue collection. For enzymatic digestion of solid tumors, tumor specimen was diced into RPMI-1640, washed and centrifuged at 800 rpm for 5 min at 15-22° C., resuspended in enzymatic digestion buffer (0.2 mg/ml collagenase and 30 units/ml DNase in RPMI-1640) before overnight rotation at room temperature. Cells were then washed and cryopreserved as single cell suspensions for later use. Some solid tumor samples were physically dissociated using a Bellco Cellector device. For antigen profiling, seven solid tumor samples were enzymatically digested overnight and two were physically dissociated. On the day of study, cells were thawed and stained with indicated antibodies for extracellular protein analysis or fixed and permeabilized for staining of intracellular antigens. Multiparameter phenotypic analysis was performed on gated viable tumor cells (EpCAM$^+$, 7AAD negative, CD45 negative) using antibodies specific for the following proteins: folate receptor alpha (FR) (also known as folate binding protein (FBP)), mesothelin, HER2/neu, IL-13R$\alpha$2, EphA2, NY-ESO-1, and MAGE-1 and compared to staining achieved using isotype antibody. Antigen positive established tumor cell lines were used as positive control whenever possible. Acquisition was performed on a BD Canto II flow cytometer and analysis performed using Flo-Jo software.

The antibodies used for the flow cytometric immunofluorescence analysis were as follows: antibodies against human CD45, EpCAM, HER2 and IL-13R$\alpha$2 were purchased from Biolegend (San Diego, Calif.); antibodies against FR/FBP and mesothelin were from R&D Systems (Minneapolis, Minn.); antibody against EphA2 was from Millipore (Billerica, MA); antibody against NY-ESO-1 was from Invitrogen (Camarillo, Calif.); and antibody against MAGE-1 was from Epitomics (Burlingame, Calif.). 7-AAD viability staining solution was purchased from BD Bioscience.

The flow cytometric immunofluorescence analysis was performed as follows: cells were resuspended in FACS buffer consisting of PBS with 2% FBS (Gemini Bioproducts). $10^6$ cells in 100 μl were directly stained with fluorochrome-conjugated mAbs at 4° C. for 40 min in the dark. For unconjugated antibodies, second fluoro-chrome-conjugated antibodies were stained for another 20 minutes. For viability gating, cells were briefly stained with 7-AAD solution and analyzed for nonviable cell exclusion using a FACS Cantor II (BD Biosciences). Intracellular staining was according to eBiosciences protocol (San Diego, Calif.). Results: In the study of nine primary human ovarian cancers, 38.6%±13.4% of all viable cells from solid tumor cell suspensions were EpCAM$^+$ tumor cells, while 28.6%±15.3% were CD45$^+$ leukocytes (Table 5). Leukocytes were comprised of CD14$^+$ monocytes, T lymphocytes, and low numbers of B lymphocytes, as well as other (non-T, B, mono) cells not defined within the applied antibody cocktail.

TABLE 5

Composition of cells from primary solid ovarian

| | | | | | | | | % of viable leukocytes | | | |
|---|---|---|---|---|---|---|---|---|---|---|---|
| | Date | % viable of total | | | % of viable cells | | | T | B | | |
| Sample | collected | total | tumor | leuco | CD45+ | EpCam+ | CD45− | cells | cells | mono | other |
| 1796 | Mar. 21, 2011 | 20.6 | 19.6 | 55.1 | 10.2 | 39.5 | 89.8 | 4.7 | 1.6 | 60.1 | 33.6 |
| 1797 | Mar. 22, 2011 | 56.5 | 51.3 | 72.0 | 34.5 | 29.1 | 65.5 | 24.4 | 7.6 | 36.0 | 31.9 |
| 1807 | May 17, 2011 | 52.1 | 68.0 | 78.9 | 24.3 | 49.3 | 75.7 | 9.3 | 0.5 | 44.8 | 45.4 |
| 1836 | Aug. 24, 2011 | 53.9 | 57.2 | 46.6 | 25.8 | 30.7 | 74.2 | 5.2 | 0.5 | 67.6 | 26.3 |
| 1884 | Apr. 18, 2012 | 71.6 | 85.1 | 43.1 | 20.1 | 32.9 | 79.9 | 30.8 | 9.7 | 18.4 | 41.1 |
| 1913 | Sep. 24, 2012 | 56.2 | 86.4 | 85.2 | 23.5 | 23.7 | 76.5 | 29.9 | ND | 27.9 | 24.9 |
| 1922* | Apr. 22, 2013 | 74.5 | 67.3 | 81.5 | 51.3 | 35.6 | 48.7 | 62.4 | ND | 14.7 | 12.8 |
| 1934 | Dec. 12, 2012 | 85.1 | 86.1 | 88.5 | 13.7 | 68.4 | 86.3 | 47.5 | ND | 20.3 | 21.5 |

TABLE 5-continued

Composition of cells from primary solid ovarian

| | | % viable of total | | | % of viable cells | | | % of viable leukocytes | | | |
|---|---|---|---|---|---|---|---|---|---|---|---|
| Sample | Date collected | total | tumor | leuco | CD45+ | EpCam+ | CD45− | T cells | B cells | mono | other |
| 1938* | Apr. 22, 2013 | 47.1 | 30.5 | 79.5 | 54.0 | 38.0 | 46.0 | 23.8 | ND | 61.5 | 6.7 |
| average | | 57.5 | 61.3 | 70.0 | 28.6 | 38.6 | 71.4 | 26.4 | 4.0 | 39.0 | 27.2 |
| STD EV | | 18.59 | 24.23 | 17.22 | 15.33 | 13.32 | 15.33 | 19.35 | 4.35 | 20.31 | 12.52 |
| SEM | | 6.20 | 8.08 | 5.74 | 5.11 | 4.44 | 5.11 | 6.45 | 1.45 | 6.77 | 4.17 |

Note:
This table contains samples prepared by enzyme digestion of solid tumor only except as noted (*)

Among viable tumor cells, a variety of cell surface or intracellular antigens were detected by flow cytometry. The expression of the antigens is shown in Table 6 below.

TABLE 6

Expression of tumor antigens in human ovarian tumor samples (%)

| Tumor | FR/FBP | Mesothelin | Her-2 | IL-13Rα2 | EphA2 | NY-ESO-1 | MAGE1 |
|---|---|---|---|---|---|---|---|
| 1796TuTcE | 99.20 | 4.72 | 72.30 | 35.60 | 17.60 | 19.20 | 7.39 |
| 1797TuTcE | 99.50 | 4.29 | 99.80 | 24.60 | 4.57 | 60.80 | 0.59 |
| 1807TuTcE | 99.90 | 6.53 | 89.90 | 34.00 | 9.76 | 44.50 | 0.85 |
| 1836TuTcE | 96.90 | 61.50 | 93.90 | 34.30 | 42.30 | 27.30 | 0.27 |
| 1884TuTcE | 98.20 | 4.50 | 42.00 | 18.60 | 12.90 | 11.50 | 14.50 |
| 1913TuTcE | 98.40 | 28.30 | 85.60 | 35.60 | 12.40 | 34.30 | 5.79 |
| 1922Bellco | 99.00 | 20.40 | 82.50 | 20.60 | 28.30 | 38.40 | 3.96 |
| 1934TuTcE | 88.30 | 2.58 | 12.30 | 3.42 | 8.27 | 5.65 | 29.10 |
| 1938Bellco | 94.20 | 14.50 | 96.70 | 62.40 | 22.60 | 36.60 | 24.30 |
| average | 97.07 | 16.37 | 75.00 | 29.90 | 17.63 | 30.92 | 9.64 |
| SD | 3.71 | 17.98 | 27.61 | 15.28 | 11.14 | 16.13 | 10.09 |
| SEM | 1.24 | 5.99 | 9.20 | 5.09 | 3.71 | 5.38 | 3.36 |

Among all nine samples tested, high frequencies (>70%) of EpCAM+ cells were FR/FBP+ and HER2+ (Table 6). Mesothelin, IL-13Rα2, NY-ESO-1, EphA2, and MAGE-1 were expressed at lower frequencies than FR and HER2. MAGE-1 and mesothelin expression was highly variable among specimens tested with some cells showing no detectable levels of expression.

Table 7 provides the values for mean fluorescence intensity (MFI) of the antibodies to the Exemplary Vaccine 1 antigens in comparison to their matched isotype antibody control (Iso). Antigens that were expressed on the greatest frequency of EpCAM+ tumor cells, such as FR/FBP and HER2, were also expressed at the highest level, as shown by analysis of MFI.

TABLE 7

Expression of tumor antigens in human ovarian tumor samples (MFI)

| Tumor | FR/FBP (Iso) | Mesothelin (Iso) | Her-2 (Iso) | IL-13Rα2 (Iso) | EphA2 (Iso) | NY-ESO-1 (Iso) | MAGE1 (Iso) |
|---|---|---|---|---|---|---|---|
| 1796TuTcE | 1982 | 178 | 300 | 142 | 96.1 | 262 | 189 |
| | (43.8) | (117) | (43.8) | (43.8) | (43.8) | (94.3) | (54.5) |
| 1797TuTcE | 7788 | 99.6 | 5340 | 118 | 65.7 | 344 | 165 |
| | (30.7) | (76.2) | (30.7) | (30.7) | (30.7) | (77.2) | (41.4) |
| 1807TuTcE | 4897 | 104 | 467 | 187 | 104 | 295 | 194 |
| | (55.3) | (71.3) | (55.3) | (55.3) | (55.3) | (86.8) | (55.8) |
| 1836TuTcE | 13400 | 861 | 815 | 159 | 153 | 289 | 153 |
| | (50.5) | (149) | (50.5) | (50.5) | (50.5) | (80.5) | (48.9) |
| 1884TuTcE | 1775 | 159 | 156 | 99.2 | 88.5 | 124 | 330 |
| | (49) | (133) | (49) | (49) | (49) | (68.6) | (48.8) |
| 1913TuTcE | 2767 | 326 | 473 | 148 | 93.6 | 290 | 201 |
| | (44.6) | (150) | (44.6) | (44.6) | (44.6) | (140) | (57.3) |
| 1922Bellco | 1603 | 300 | 338 | 78.6 | 102 | 333 | 261 |
| | (24.1) | (150) | (24.1) | (24.1) | (24.1) | (92) | (47.3) |
| 1934TuTcE | 810 | 164 | 139 | 99.6 | 114 | 120 | 399 |
| | (58) | (129) | (58) | (58) | (58) | (76.2) | (52.6) |
| 1938Bellco | 588 | 151 | 687 | 207 | 91.5 | 675 | 516 |
| | (37) | (122) | (37) | (37) | (37) | (166) | (192) |

TABLE 7-continued

Expression of tumor antigens in human ovarian tumor samples (MFI)

| Tumor | FR/FBP (Iso) | Mesothelin (Iso) | Her-2 (Iso) | IL-13Rα2 (Iso) | EphA2 (Iso) | NY-ESO-1 (Iso) | MAGE1 (Iso) |
|---|---|---|---|---|---|---|---|
| average | 3956.67 | 260.29 | 968.33 | 137.60 | 100.93 | 303.56 | 267.56 |
|  | (43.67) | (121.28) | (43.67) | (43.67) | (43.67) | (97.96) | (66.51) |
| SD | 4207.19 | 238.55 | 1654.63 | 42.76 | 23.60 | 161.48 | 123.79 |
|  | (11.25) | (29.27) | (11.25) | (11.25) | (11.25) | (32.87) | (47.31) |
| SEM | 1402.40 | 79.52 | 551.54 | 14.25 | 7.87 | 53.83 | 41.26 |
|  | (3.75) | (9.76) | (3.75) | (3.75) | (3.75) | (10.96) | (15.77) |

Conclusions: The above results suggest an opportunity for immune-based therapy for ovarian cancer. In particular, expression levels of FR/FBP and HER2 suggest that these molecules may allow for near universal therapy among ovarian cancer patients. FR is a strong candidate antigen for targeting based on its near ubiquitous expression among ovarian cancer cells within a tumor and among different patients. Mesothelin, IL-13Rα2, NY-ESO-1, MAGE-1, and EphA2 also represent reasonable targets for immune-based therapy for ovarian cancer.

In sum, these data provide a rationale for targeting antigens including FR/FBP, HER2, mesothelin, IL-13Rα, NY-ESO-1, MAGE-1, and EphA2 for women with ovarian cancer.

Example 9

Quantitative Real-Time PCR-Based Analysis of Gene Expression In Human Ovarian Cancer Cells, Cancer Stem Cells, and Ovarian Cancer Daughter Cells Objective: To compare the gene expression of the antigens of Exemplary Vaccine 1 in human ovarian cancer cells, cancer stem cells, and ovarian cancer daughter cells using real-time PCR (RT-PCR).

Materials & Methods:
1. Antigens: Her-2, IL-13Rα2, mesothelin, EphA2, FOLR1, MAGE-A1, NY-ESO-1
2. PCR gene probes and reagents:
   HER2 gene expression assay, Life Technologies, Part # Hs01001580_ml;
   MAGE-A1 gene expression assay, Life Technologies, Part # Hs00607097_ml;
   IL-13Rα2 gene expression assay, Life Technologies, Part # Hs00152924_ml;
   EphA2, gene expression assay, Life Technologies, Part # Hs00171656_ml;
   FOLR1, gene expression assay, Life Technologies, Part # Hs01124179_gl;
   NY-ESO-1, gene expression assay, Life Technologies, Part # Hs00265824_ml;
   Mesothelin, gene expression assay, Life Technologies, Part # Hs00245879_ml;
   GAPDH gene expression assay, Life Technologies, Part # Hs02758991_gl;
   TaqMan™ gene expression master mix; Life Technologies, part #4369016;
   Rneasy® Mini Kit RNA isolation (cat #74104, Qiagen); and
   High Capacity® cDNA Reverse Transcription Kit with RNase Inhibitor (cat #4374966, Life Technologies)
3. Cell Lines: human ovarian cancer cells (AC) 882 AC and 1031AC, cancer stem cells (CSC) 882CSC and 1031 CSC, ovarian cancer daughter cells (ADC) 882 ADC and 1031 ADC
4. Human Ovarian Cancer Cells (AC) Culture
   Ovarian cancer cell lines 882AC and 1031 AC were cultured in McCoy's 5A medium (Mediatech, Herndon, Va.) supplied with 10% fetal bovine serum (Omega Scientific, Inc.) and Pen Strep Glutamine (100×) (Invitrogen). All cells were cultured in 5% $CO_2$ and at 37° C. in a cell incubator (Forma Scientific, Inc.).
5. Human Ovarian Cancer Stem Cells (CSC) Culture
   Human ovarian cancers cells (882AC,1031AC) were grown in Dulbecco's modified Eagle's medium DMEM/F12 medium (Invitrogen) containing 10% fetal bovine serum (FBS) as growth medium and plated at a density of 1×10⁶ cells per 75 cm² cell culture flask (Corning Inc.). The cells attached and grew as a monolayer in flasks. The monolayers were then switched into DMEM/F12 medium supplemented with B-27 (Invitrogen, Carlsbad, Calif.), 20 ng/ml of basic fibroblast growth factor, and 20 ng/ml of endothelial-derived growth factor (Peprotech, Rocky Hill, N.J.).
6. Human Ovarian Cancer Daughter Cells (ADC) Culture
   Human ovarian cancer stem cells (882CSC,1031CSC) were grown in Dulbecco's modified Eagle's medium DMEM/F12 medium (Invitrogen) containing 10% fetal bovine serum (FBS) as growth medium and plated at a density of 1×10⁶ cells per 75 cm² cell culture flask (Corning Inc.). The cells attached and grew as a monolayer in flasks in about 2-3 weeks.
7. RNA Extraction, cDNA Synthesis, and qPCR
   Total RNA was extracted from cell lines 882AC, 882CSC, 882ADC, and 1031 AC, 1031CSC, and 1031ADC using Rneasy Mini Kit (Qiagen) according to the manufacturer's instructions. The complementary DNA was synthesized using High-Capacity® cDNA Reverse Transcription (cat #4374966), Life Technologies, Calif.) following the manufacturer's protocol.

The real-time PCR reactions were performed according to the manufacturer's instructions. The reaction consisted of 8.0 µl cDNA (42 ng), 10 µl TaqMan® PCR Master Mix, 1.0 µl nuclease-free water and the following 1.0 µl TaqMan® PCR probes (20×) for seven genes: Hs01001580_ml (HER2), Hs00607097_ml(MAGE-A1), Hs00152924_ml (IL-13Rα2), Hs00171656_ml(EphA2), Hs01124179_gl (FOLR1), Hs00265824_ml(NY-ESO-1), Hs00245879_ml (mesothelin) as well as an internal control Hs02758991 gl (GAPDH). The reactions were performed on Bio-Rad iQ™5 Real Time PCR system with the following thermal cycles: one cycle of 50° C. for 2 minutes and 95° C. for 10 minutes, followed by 40 cycles with a denaturation at 95° C. for 15 seconds and an annealing/extension at 56° C. for 60 seconds, extension at 72° C. for 30 seconds and a final extension step at 72° C. for 5 min. A melting curve was determined at the end of each reaction to verify the specificity of the PCR reaction. Ct Data analysis was performed using the Bio-Rad software supplied with the IQ™5 Cycler system.

8. Data Analysis Using [2^-Δ(ΔCt)] Method

Relative quantities for each antigen gene were calculated using the comparative [2^-Δ(ΔCt)] method. The Ct value represents the cycle number at which the fluorescence passes the defined threshold. Delta Ct values (delta $Ct=Ct_{test\ gene}-Ct_{mean\ of\ control\ genes}$) were used to compare the difference of gene expression. Ct values of antigens gene expression levels were normalized to GAPDH and comparative Ct method [2^-Δ(ΔCt)] was used to evaluate the gene expression.

Results: The relative gene expression of HER2 in 882AC (FIG. 1A), 882CSC (FIG. 1B), and 882ADC (FIG. 1C) were 0.4414, 1.16 and 1.67, respectively, suggesting that the HER2 gene was expressed at a high level in ovarian cancer stem cells (CSC) and ovarian cancer daughter cells (ADC). The relative gene expression of EphA2 in 882AC (FIG. 1A), 882CSC (FIG. 1B), and 882ADC (FIG. 1C) were 1.51, 1.69 and 4.06, respectively, suggesting that EphA2 gene expression was expressed at a high level in ovarian cancer cells (AC), cancer stem cells (CSC), and ovarian cancer daughter cells (ADC). The relative gene expression of mesothelin was low in 882AC, 882CSC, and 882ADC. The relative gene expression of IL13Rα2 was low in 882CSC and 882ADC, and is undetectable in 882AC. The gene expression of FOLR1 was low in control cells and undetectable in 882AC, 882CSC, and 882ADC. Finally, the gene expression of NY-ESO-1 was undetectable in the control cells, as well as in 882AC, 882CSC, and 882ADC.

Next, the expression level of the above genes were compared amongst 882AC, 882CSC and 882ADC. As shown in FIG. 2, the relative gene expression of HER2 and EphA2 in ovarian cancer stem cells (882CSC) was higher than that in ovarian cancer cells (882AC), whereas the relative gene expression of mesothelin and MAGE-A1 in 882CSC was lower than that in 882AC. FOLR1 and NY-ESO-1 were undetectable in 882AC, 882CSC, and 882ADC. The relative gene expression of IL13Rα2 was low in both 882CSC and 882ADC, and was undetectable in 882AC.

The relative gene expression of HER2, EphA2, mesothelin, and MAGE-A1 were higher in daughter cells (882ADC) than that in cancer stem cell (882CSC), and the relative gene expression of IL13Rα2 in 882ADC was lower than that in 882 CSC. FOLR1 and NY-ESO-1 were undetectable in 882AC, 882CSC, and 882ADC.

The gene expression of the above-mentioned antigens was evaluated in other human ovarian cancer cells (1031AC), cancer stem cells (1031CSC), and ovarian cancer daughter cells (1031ADC). As shown in FIG. 3, the relative gene expression of HER2 in 1031AC, 1031CSC, and 1031ADC were 0.6491, 0.6099 and 0.6799, respectively, suggesting that the HER2 relative gene expression was low. The relative gene expression of EphA2 in 1031AC, 1031CSC and 1031ADC were 1.46, 2.265 and 2.93, respectively, suggesting that EphA2 has increased gene expression in ovarian cancer cell (AC), cancer stem cell (CSC), and ovarian cancer daughter cell (ADC), compared to human ovarian epithelial cell (HoEpic). The relative gene expression of MAGE-A1 in 1031AC and 1031ADC are 1.38 and 1.34, respectively, which is a little higher than expression in the control cell. The relative gene expression of mesothelin was lower in 1031AC, 1031CSC, and 1031ADC, and the relative gene expression of FOLR1, IL-13Rα2 was undetectable in 1031AC, 1031CSC, and 1031ADC. The gene expression of NY-ESO-1 was undetectable both in the control cell as well as in 1031AC, 1031CSC, and 1031ADC.

Figure 4B:
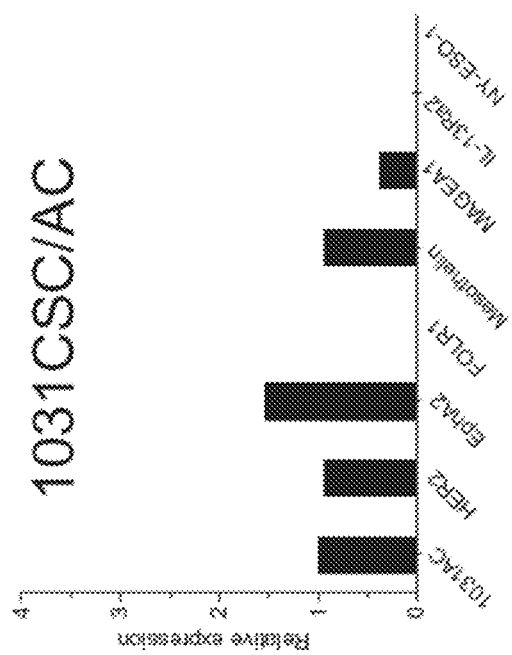
FIG. 4B is a bar graph showing the RNA expression of the antigens of Exemplary Vaccine 1 in human ovarian cancer daughter cell (1031ADC) relative to human ovarian cancer stem cell (1031CSC) (FIG. 4B).

Gene expression of the above-noted genes was compared amongst 1031AC, 1031CSC, and 1031ADC. As shown in FIG. 4, the gene expression of EphA2 in 1031CSC relative to 1031AC is 1.54, suggesting that the gene expression in 1031CSC is higher than that in 1031AC. The gene expression of HER2, Mesothelin, and MAGE-A1 in 1031CSC is at a lower level than that in 1031AC. The expression levels of HER2, EphA2, Mesothelin, and MAGEA1 in 1031ADC are higher than that in 1031CSC. The gene expression of IL-13Rα2, FOLR1, and NY-ESO-1 are undetectable in 1031AC, 1031CSC and 1031ADC.

Conclusions:

1. Based on the Ct value of q-PCR, HER2, EphA2, mesothelin, and MAGE-A1 were expressed in ovarian cancer cells (882AC, 1031 AC), ovarian cancer stem cells (882CSC, 1031CSC), and ovarian cancer daughter cells (882ADC, 1031ADC). IL13Rα2 was also expressed in 882CSC and 882ADC, but was undetectable under the experimental conditions used herein in 882AC, 1031 AC, 1031CSC, and 1031ADC. FOLR1 and NY-ESO-1 were undetectable under the experimental conditions in ovarian cancer cells (882AC, 1031 AC), cancer stem cells (882CSC, 1031CSC), or daughter cells (882ADC, 1031ADC).

2. The gene expression level of HER2 and EphA2 in 882CSC was 1.122 and 2.62 fold higher compared with 882AC, while mesothelin and MAGE-A1 were expressed at 0.5913 and 0.0174 compared with 882AC. The relative gene expression of HER2, EphA2, mesothelin, and MAGEA1 in 882ADC was 1.45, 2.39, 10.85, and 15.45-fold higher compared to expression in 882CSC. The gene expression of IL-13Rα2 in 882CSC was higher than that in 882ADC.

3. The gene expression level of EphA2 was 1.54 fold higher in 1031CSC compared with 1031 AC, whereas the gene expression level of HER2, mesothelin, and MAGE-A1 in 1031CSC were 0.94, 0.94, and 0.39 compared with 1031 AC. The gene expression level of HER2, EphA2, mesothelin, and MAGE-A1 in 1031ADC were 1.11, 1.3, 1.35, and 1.82 fold higher in 1031ADC compared with 1031CSC.

4. The gene expression of IL-13Rα2, FOLR1, and NY-ESO-1 was undetectable in 1031AC, 1031CSC, and 1031ADC under the reaction conditions used herein, suggesting that these genes were expressed at lower levels in these cells.

Taken together these data identify unique gene expression molecular signatures for antigens of Exemplary Vaccine 1 and provide a framework for the rational design of immunotherapy target for human ovarian cancer cells, cancer stem cells, and ovarian cancer daughter cells.

Example 10

Analysis of the Expression of Tumor Antigens In Human Ovarian Tumor Cancer Cells, Cancer Stem Cells, And Ovarian Cancer Daughter Cells Based On Flow Cytometric Assay Objective: To utilize flow cytometry-based analysis of ICT 140 antigens expression profiles in primary human ovarian cancer cells, cancer stem cells, and ovarian cancer daughter cells for potential immunotherapeutic targeting.

Materials & Methods:

1. Reagents

DMEM/F12: Invitrogen, Cat #11330-057 (Lot #1184632, Lot #1109388, Lot #891768);

McCoy's 5A, 1×: Mediatech, Inc, cat #10-050-CV (Lot #10050090, Lot #10050088); B-27 supplement (50×): Invitrogen, cat #12587-010 (Lot #1192265, Lot #1153924, Lot #1079052);

Fetal Bovine Serum: Omega Scientific, Inc. Cat # FB-11 (Lot #170108, Lot #110300); Pen Strep Glutamine: Invitrogen, cat #10378-016 (Lot #1030595); Human FGF-basic: PeproTech, cat #100-18B (Lot #041208-1, Lot #051108); Human EGF: cat # AF-100-15 (Lot #0212AFC05, Lot #0711AFC05, Lot #0211AFC05-1, Lot #0911AFC05-1);

BD Cytofix/cytoperm, Fixation and permeabilization kit. Cat #51-6896KC (Lot #81617); and The antibodies used for the flow cytometric assay were as follows: PE-labeled antibodies against human EphA2, FOLR1, mesothelin were purchased from R&D Systems (Minneapolis, Minn.); antibodies against human NY-ESO-1 and MAGE-A1 were from Invitrogen (Camarillo, Calif.); PE-labeled antibodies against human HER2 and IL-13Rα2 were from Biolegend (San Diego, Calif.); PE-labeled antibodies against human IL-13Rα2 was from Abcam (Cambridge, Mass.); and antibodies against human mesothelin was from Santa Cruz Biotechnology (Dallas, Tex.).

2. Cell Lines

Primary human ovarian cancer cells (AC): 882AC, 1031 AC, 1078AC, 1082AC, 1077AC, 1105AC, and 1064AC;

Human ovarian cancer stem cells (CSC): 882CSC, 1031CSC, 1078CSC, and 1082CSC;

Human ovarian cancer daughter cells (ADC): 882ADC, 1031 ADC, and 1078ADC, and;

SKOV3 human ovarian cancer cell (American Type Culture Collection).

3. Human Ovarian Cancer Cells (AC) Culture

Human ovarian cancer cell lines (AC) (882AC, 1031 AC, 1078AC, 1082AC, 1077AC, 1105AC, 1064AC, and SKOV3) were cultured in McCoy's 5A medium (Mediatech, Herndon, Va.) supplied with 10% fetal bovine serum (Omega Scientific, Inc.) and Pen Strep Glutamine (100×) (Invitrogen). All cells were cultured in 5% $CO_2$ and 37° C. in a cell incubator (Forma Scientific, Inc).

4. Human Ovarian Cancer Stem Cells (CSC) Culture

Human ovarian cancers cells (AC) (882AC, 1031 AC, 1078AC, 1082AC) were grown in Dulbecco's modified Eagle's medium DMEM/F12 medium (Invitrogen) containing 10% fetal bovine serum (FBS) as growth medium and plated at a density of $1\times10^6$ cells per 75 cm² cell culture flask (Corning Inc.). The cells attached and grew as a monolayer in flasks. Then, these monolayer cells were switched into DMEM/F12 medium supplemented with B-27 (Invitrogen, Carlsbad, Calif.), 20 ng/ml of basic fibroblast growth factor, and 20 ng/ml of endothelial-derived growth factor (Peprotech, Rocky Hill, N.J.).

5. Human Ovarian Cancer Daughter Cells (ADC) Culture

Human ovarian cancer stem cells (ADC) (882ADC, 1031ADC,1078ADC) were grown in Dulbecco's modified Eagle's medium DMEM/F12 medium (Invitrogen) containing 10% fetal bovine serum (FBS) as growth medium and plated at a density of $1\times10^6$ cells per 75 cm² cell culture flask (Corning Inc.). The cells attached and grew as a monolayer in flasks in about 2-3 weeks.

6. Flow Cytometric Analysis

The human ovarian cancer cells, cancer stem cells, and ovarian cancer daughter cells ($0.5\times10^6$ or $1\times10^6$) were resuspended in 1% FBS-PBS and stained with the following specific PE labeled antibodies: anti-HER2, anti-IL-13Rα2, anti-mesothelin, anti-EphA2, and anti-FOLR1. For MAGE-A1 staining, the cells were first contacted with the MAGE-A1 specific monoclonal antibody, and then labeled with 2nd PE-conjugated mAb.

For intracellular antigens (NY-ESO-1) staining, cells were permeabilized using Cytofix/Cytoperm kit (BD Biosciences) and stained with PE-conjugated 2nd antibody. Flow cytometric analysis was performed using a CyAn™ flow cytometer (Beckman Coulter) and the data was analyzed using Summit (Dako, Carpinteria, Calif.) software.

Results: In this study, we tested the expression of the seven antigens of Exemplary Vaccine 1 in seven primary human ovarian cancer cells, four human ovarian cancer stem cells, and three human ovarian cancer daughter cells using a FACS assay. The expression of the tumor antigens in the human ovarian tumor samples (in %) are provided in Tables 8-10.

TABLE 8

Expression of tumor antigens in human ovarian tumor samples (%)

| Tumor ID | FOLR1 | Mesothelin | HER2 | IL13Rα2 | EpHA2 | NYESO1 | MAGE1 |
|---|---|---|---|---|---|---|---|
| 882-CSC | 12.36 | 2.24 | 84.33 | 15.67 | 75.59 | 0.1 | 0.11 |
| 882-AC | 7.11 | 1.57 | 95.75 | 18.39 | 96.73 | 0.57 | 0.91 |
| 882-ADC | 4.15 | 2.27 | 97.78 | 5.4 | 98.84 | 0.16 | 0.13 |
| 1031-CSC | 13.01 | 2.12 | 49.93 | 9.67 | 84.61 | | |
| 1031-AC | 3.52 | 1.36 | 97.57 | 5.03 | 96.78 | 0.59 | 15.28 |
| 1031-ADC | 4.77 | 2.49 | 98.59 | 5.06 | 95.45 | 69.98 | |
| 1078-CSC | 56.83 | 2.58 | 83.94 | 31.47 | 50.24 | | |
| 1078-AC | 4.26 | 1.55 | 99.16 | 58.81 | 98.99 | | |
| 1078-ADC | 8.31 | 2.89 | 96.15 | 93.79 | 98.85 | | |
| 1085AC | 3.17 | 1.65 | 86.87 | 31.55 | 84.13 | 16.4 | 53.5 |
| Average | 11.749 | 2.072 | 89.007 | 27.484 | 88.021 | 14.63 | 13.99 |
| SD | 16.233 | 0.51437 | 14.98453 | 28.7606 | 15.5317 | 27.85 | 23.01 |
| SEM | 5.13 | 0.163 | 4.73 | 9.09 | 4.911 | 11.37 | 10.29 |

Table 8 is a summary of the expression data for the Exemplary Vaccine 1 antigens in four primary human ovarian cancer cells, three human ovarian cancer stem cells, and three human ovarian daughter cells. The results indicate that the average antigen expression of HER2, EphA2, IL 13Rα2, NY-ESO-1, MAGE-A1 FOLR1, and Mesothelin were 89.01%, 88.02%, 27.48%,14.63%, 13.99%, 11.75% and 2.07%, respectively. Mesothelin was expressed at low levels in ovarian cancer cells, cancer stem cells and ovarian cancer daughter cells. In contrast, HER2 and EphA2 were expressed at high levels in ovarian cancer cells, cancer stem cells, and ovarian cancer daughter cells.

Table 9 provides the values of mean fluorescence intensity (MFI) of the antibodies to some of the Exemplary Vaccine 1 antigens in comparison to their matched isotype antibody control (Iso). The MFI results indicated that the MFI of isotype antibodies are lower than that of the MFI of antigen antibodies.

Taken together, the above data show that the antigens of Exemplary Vaccine 1 are good immunotherapy targets for human ovarian cancer cells, cancer stem cells, as well as ovarian cancer daughter cells.

TABLE 9

Expression of tumor antigens in human ovarian tumor samples (MFI)

| Tumor ID | FR | FR (Iso) | Meso | Meso (Iso) | HER2 | HER2 (Iso) | IL13Rα2 | IL13Rα2 (Iso) | EpHA2 | EpHA2 (Iso) |
|---|---|---|---|---|---|---|---|---|---|---|
| 882-CSC | 15.35 | 6.48 | 10.6 | 6.48 | 21.86 | 6.48 | 19.13 | 6.48 | 41.4 | 18.55 |
| 882-AC | 17.4 | 10.28 | 8.33 | 10.28 | 22.69 | 10.28 | 18.9 | 10.28 | 137.9 | 28.94 |
| 882-ADC | 53.65 | 26.03 | 102.4 | 12.85 | 89.58 | 16.96 | 32.75 | 14.78 | 314.05 | 22.88 |
| 1031-CSC | 8.47 | 47.21 | 24.66 | 47.21 | 6.5 | 47.21 | 10.59 | 47.21 | 152.6 | 47.21 |
| 1031-AC | 37.07 | 6.63 | 42.83 | 7.35 | 48.02 | 6.75 | 16.3 | 6.75 | 113.75 | 6.75 |
| 1031-ADC | 9.92 | 2.86 | 28.75 | 2.86 | 29.52 | 3 | 10.85 | 4.41 | 91.6 | 4.41 |
| 1078-CSC | 142.9 | 29.82 | 17.73 | 29.82 | 81.21 | 29.82 | 95.99 | 29.82 | 64.49 | 29.82 |
| 1078-AC | 35.87 | 19.97 | 25.42 | 19.97 | 48.15 | 19.97 | 42.58 | 19.97 | 251.6 | 94.52 |
| 1078-ADC | 31.22 | 9.05 | 15.49 | 9.05 | 50.9 | 9.05 | 53.6 | 9.05 | 49.2 | 9.05 |
| Skov3 | 106.3 | 58.12 | 79.95 | 58.12 | 500 | 58.12 | 121.8 | 58.12 | 113.5 | 13.54 |
| Avg. | 45.81 | 21.645 | 35.61 | 20.399 | 89.843 | 20.764 | 42.249 | 20.687 | 133.01 | 27.567 |
| SD | 44.65 | 18.765 | 31.34 | 18.828 | 146.45 | 18.723 | 38.263 | 18.643 | 88.081 | 26.849 |
| SEM | 14.11 | 5.93 | 9.91 | 5.95 | 46.17 | 5.91 | 12 | 5.89 | 27.85 | 8.488 |

As shown in Table 10, HER2, IL13Rα2, and EpHA2 were highly expressed in 1082AC, 1082CSC, 1077AC, 1105AC, and 1064AC, with their average expression levels in these cell lines being 82.03%, 44.97%, and 48.86%, respectively. HER2, EpHA2, and FOLR1 were also expressed at the higher level in SKOV3 human ovarian cancer cell. Mesothelin, NY-ESO-1, and MAGE-A1 were expressed at lower levels.

TABLE 10

Expression of tumor antigens in human ovarian tumor samples (%)

| Tumor ID | FR | Meso | HER2 | IL13Rα2 | EpHA2 | NYESO1 | MAGE1 |
|---|---|---|---|---|---|---|---|
| 1082-CSC | | 3.96 | 87.64 | 53.15 | | | |
| 1082-AC | | 5.22 | 98.25 | 7.25 | | 0.66 | 0.17 |
| 1077-AC | | 1.55 | 83.63 | 88.73 | 14.02 | | |
| 1105-AC | | 3.28 | 78.59 | 4.5 | 83.71 | | |
| 1064-AC | | 1.27 | 62.05 | 71.22 | | | |
| Avg. | | 3.056 | 82.032 | 44.97 | 48.86 | | |
| SD | | 1.659 | 13.306 | 37.853 | 49.28 | | |
| SEM | | 0.74 | 5.94 | 16.92 | 22.04 | | |
| SKOV3 | 89.17 | 1.23 | 99.5 | 0.51 | 99.67 | | |
| Avg. | 89.17 | 1.23 | 99.5 | 0.51 | 99.67 | | |
| SD | 4.2 | 0.94 | 0.63 | 0.19 | 0.01 | | |
| SEM | 2.98 | 0.54 | 0.36 | 0.11 | 0.009 | | |

Conclusion: The primary human ovarian cancer cells analyzed in the above experiments were isolated from various patients' samples. The results described above demonstrate that the ovarian cancer cells, cancer stem cells, and ovarian cancer daughter cells, express HER2 and EpHA2 at high levels, and express IL13Rα2, NY-ESO-1, MAGE-A1, and FOLR1 at moderate levels (expression is between 27.49% and 11.75%). Mesothelin is expressed at a lower expression level on these cells; however, when this data is considered in combination with its RNA expression level based on qPCR assay, mesothelin is still considered a good candidate for targeting via immunotherapy.

Some of the Exemplary Vaccine 1 antigens were up-regulated in ovarian cancer stem cells than in ovarian cancer cells and daughter cells based on FACS data in Table 8-10.

Example 11

Analysis of Binding Capacity of Exemplary Vaccine 1 HLA A2 Peptides with T2 Cells Objective: To evaluate the binding capacity of Exemplary Vaccine 1 HLA-A2 peptides and control peptide Mart1 with T2 cells.

Materials & Methods:

1. Cell line and peptides

TAP-deficient T2 cells expressing HLA-A2 were obtained from the American Type Culture Collection (ATCC) (cat #CRL-1992, Manassas, Va.) and maintained in Iscove's modified Dulbecco medium (cat #31980-030, Invitrogen, Grand Island, N.Y.) supplemented with 20% fetal bovine serum (cat # FB-01, Omega Scientific Inc.) at 37° C. with 5% $CO_2$. All peptides (Table 11) used in this study were synthesized from the American Peptide Company (Sunnyvale, Calif.). The HLA-A*0201 binding peptide Melan A/Mart-1 peptide (ELAGIGILTV (SEQ ID NO:110), cat #61013, Anaspec Inc, Calif.) was used as a positive control. MHC peptides, with more than 95% purity, were synthesized using automated solid phase techniques, purified by reversed phase-high performance liquid chromatography (HPLC), and their structures were verified by mass spectrometry. Peptides were obtained in lyophilized form, dissolved to a final concentration of 10 mg/ml in DMSO and stored at −20° C.

TABLE 11

Exemplary Vaccine 1 HLA-A2 peptides

| Antigen | HLA-A2 peptide epitope | Sequence | Product # | Lot # |
|---|---|---|---|---|
| HER2/neu | 773-782 | VMAGVGSPYV (SEQ ID NO: 40) | 362469 | S1206012T |
| IL-13Rα2 | 345-352 | WLPFGFILI (SEQ ID NO: 49) | 331052 | 1206054T |
| EphA2 | 883-891 | TLADFDPRV (SEQ ID NO: 66) | 358414 | S1206033T |
| FOLR1 | 191-199 | EIWTHSYKV (SEQ ID NO: 28) | 329542 | SU11006T |
| NY-ESO-1 | 157-165 | SLLMWITQC (SEQ ID NO: 26) | 315926 | U02032T1 |
| Mesothelin | 531-539 | VLPLTVAEV (SEQ ID NO: 17) | 368371 | 1312092X |
| MAGE-A1 | 278-286 | KVLEYVIKV (SEQ ID NO: 55) | 348003 | 1312143T |

2. Methods

The MHC peptide-binding affinity of each HLA-A2 peptide and control peptide Mart1 to HLA-A*0201 molecules was determined using the following protocol. The T2 cell line (cat # CRL-1992, ATCC®, Manassas) ($2\times10^5$) were incubated overnight at 37° C., 5% $CO_2$ with peptide (75 μg/ml) in 100 μl of AIM serum-free medium (cat #12055-091, Life Technologies) containing human 02-microglobulin (cat #126-11, Lee Biosolutions Inc, St Louis). After the incubation, cells were washed with cold PBS and then, surface HLA-A2 molecules were stained with mAb of PE Mouse anti-Human HLA-A2 (BD™ Biosciences, cat #558570) and PE Mouse IgG2b, κ Isotype Control (cat #555058, BD Biosciences, San Jose) for 30 min at 4° C., and washed twice with cold PBS. Whether these MHC peptides bind to HLA-A2 was determined by the upregulation of HLA-A2 molecules on T2 cells and demonstrated by measuring mean fluorescence intensity (MFI) using CyAn™ flow cytometry (Beckman Coulter, Inc).

Results: In this study, the T2 cell binding assay was performed to validate the binding affinity of Exemplary Vaccine 1 HLA-A2 peptides and control peptide MART 1 to HLA-A2 molecules. The relative binding affinity of the respective peptides was calculated from the mean fluorescence intensities (MFIs) as follows: The relative binding affinity fluorescence index (FI) of the respective peptides was calculated using the following formula: MFI(peptide)−MFI(untreated cells)/MFI(untreated cells). Relative binding affinities >1.5 were considered strong; 1.5 to 1.0, intermediate; and <1.0, low. HLA-A2 binding is shown as an increase in HLA-A2 MFI.

Figure 5A:
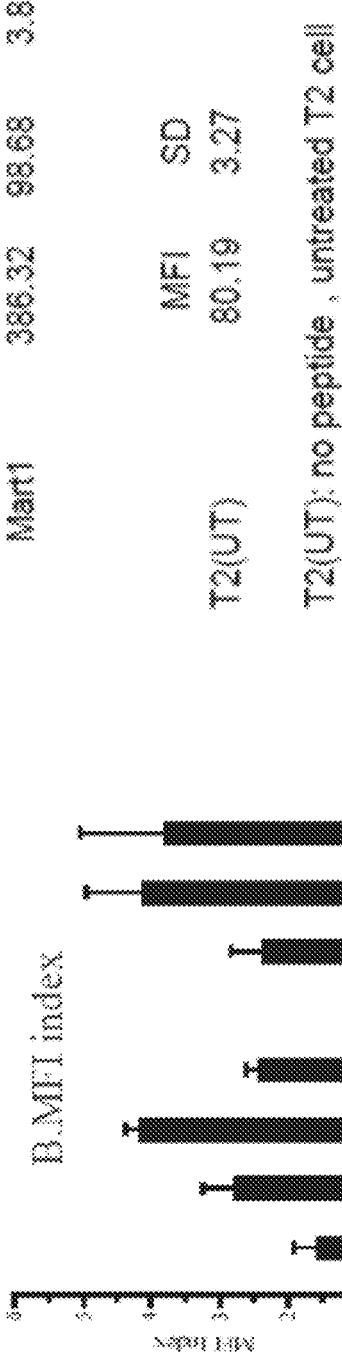
FIG. 5A is a bar graph showing the capacity of Exemplary Vaccine 1 HLA-A2 peptides to bind T2 cells.

As shown in FIG. 5A, the synthesized Exemplary Vaccine 1 peptides bound to HLA-A*0201 molecules with different affinities: peptides EphA2 p883 and mesothelin p531 apparently up-regulated the HLA-A*0201 molecules and showed high affinities to HLA-A*0201 molecules, whereas FOLR1p191 had a low affinity for HLA-A*0201.

Figure 5B:
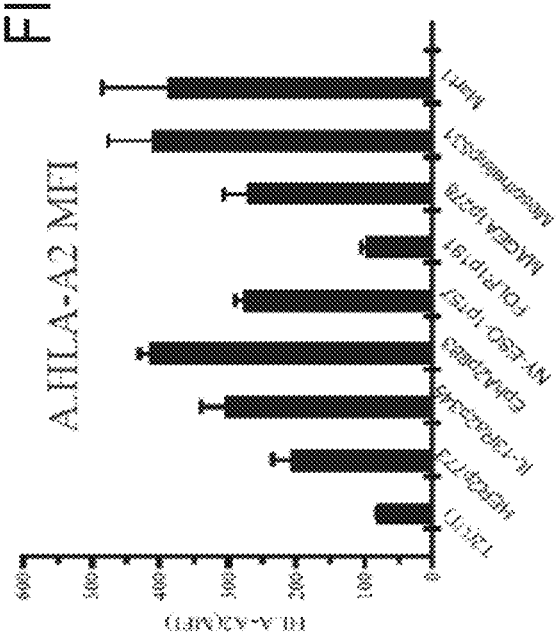
FIG. 5B is a bar graph showing the capacity of Exemplary Vaccine 1 HLA-A2 peptides to bind T2 cells.
Figure 6A:
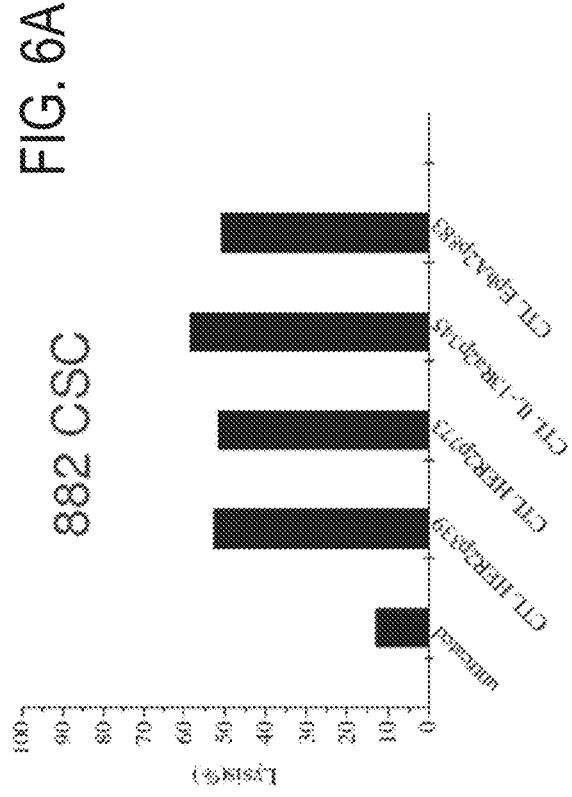
FIG. 6A is a bar graph depicting cytotoxicity of antigen-specific CTLs against HLA-A2$^+$ human ovarian cancer stem cells 882CSC. Control: 882CSC (UT): untreated cell.
Figure 6B:
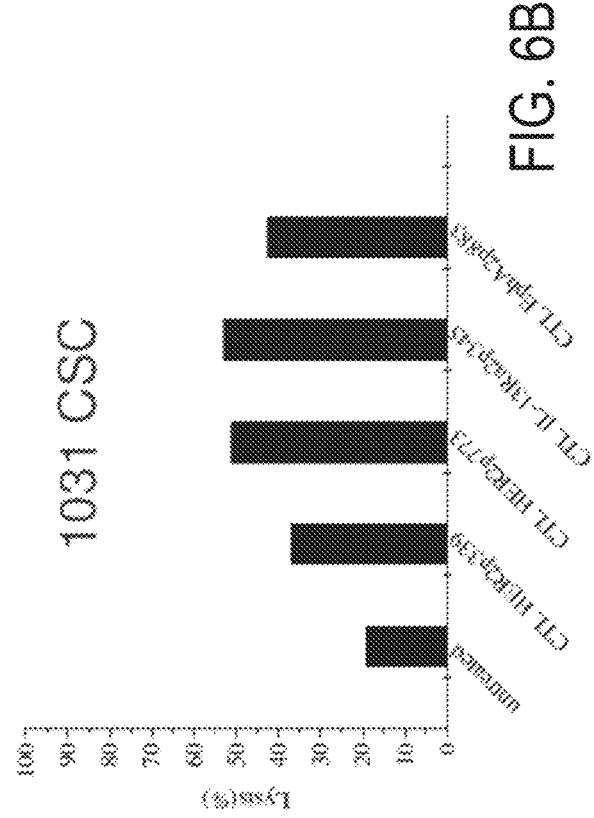
FIG. 6B is a bar graph depicting cytotoxicity of antigen-specific CTLs against HLA-A2+ human ovarian cancer stem cells 1031CSC. Control: 1031CSC (UT): untreated cell.

As shown in FIG. 5B, the binding of these peptides, except FOLR1p191, to the T2 cell line was demonstrated by an increase in MFI index. The MFI indexes of these peptides, except FOLR1 p191, are more than 1.5, indicating a high affinity binding. The positive control, Mart1 peptide, had an MFI index of 3.82. The MFI index of FOLR1 p191 is less than 1 indicating a lower affinity binding.

Conclusion: The above results demonstrate that Exemplary Vaccine 1 HLA-2 peptides (HER2p773, IL-13Rα2p345, EphA2p883, NY-ESO-1p157, MAGEA1p278, and mesothelinp531) have high affinity binding with T2 cells, whereas the FOLR1p191 peptide has a lower binding capacity for these cells. These data suggest that these peptides can be used to pulse human HLA-A2 dendritic cells and used in HLA-A2 patients.

Example 12

Evaluation of Cytotoxicity Against Human Ovarian Cancer Stem Cells

Objective: To evaluate the cytotoxicity of CTLs, induced by HLA-A2 peptides, on ICT 140 HLA-A2(+) human ovarian cancer stem cells.

In order to develop new immunotherapy strategy for ovarian cancer cells and cancer stem cells, the Exemplary Vaccine 1 antigens HLA-A2 peptides were proposed as potential targets. It was hypothesized that Exemplary Vaccine 1 HLA-A2 peptides could induce antigen-specific immune responses.

To test this hypothesis, effector CD8+ T cells were isolated and co-cultured with HLA-A2+ DC pulsed with three Exemplary Vaccine 1 peptides: HER2 p773, IL-13Rα2 p345, and EphA2 p883, as well as HER2 p339 to induce antigen-specific CTLs. Next, cytotoxicity against HLA-A2+ 882 CSC and 1031 CSC target cells was evaluated.

Materials & Methods:

1. Generation of Human Dendritic Cells

Human monocyte-derived DCs were generated using previously described methods. Briefly, monocytes were isolated from PBMC by magnetic immunoselection using EasySep™ human monocyte enrichment kit (Stem cell Technologies) based on the manufacturer's instructions, then cultured at $5\times10^7$/ml in 20 ml of GMP CellGenix™ DC serum-free medium (Cat #20801-0500, Cellgenix) supplemented with 1000 unit/ml of recombinant human GM-CSF (Cat #AF-300-03, Peprotech, Inc) and recombinant human IL-4 (Cat # AF-200-04, Peprotech, Inc), and the cells were harvested after 3 or 6 days of culture. The DCs were washed and plated in 6-well plates at a concentration of $5\times10^6$ cells/well IFN-γ (1000 unit/ml), and then monophosphoryl lipid A (MPLA, 20-50 μg/ml) (Cat # L6895, Sigma, St. Louis) was added into the wells to mature the DC for 24 hr or 48 hrs. Prior to some assays, DCs were frozen and stored in liquid nitrogen.

2. CTL induction and detection of Mart1-specific CD8+ by HLA-A*0201/Mart1 Tetramers In order to evaluate antigen-specific immune responses, CD8+ T cells were isolated from fresh or frozen apheresis by positive selection using Dynabeads® CD8 Positive Isolation Kit (Life Technologies, Grand Island, N.Y.) and co-cultured with autologous mDC for four weeks. DCs were added weekly. Briefly, mDCs were pulsed with synthetic peptides (10 μg/μl) for 6-8 hours at 37° C., and then treated with 20 μg/ml Mitomycin C (Sigma-Aldrich, St. Louis, Mo.) for 25 min at 37° C. and 5% $CO_2$. The mDCs ($5\times10^4$ cells/well) were co-cultured with autologous CD8+ T cells ($5\times10^5$ cells/well) in a 96-well plate at 37° C., 5% $CO_2$ in a final volume of 200 μl CTL medium (IMDM with 0.24 mM Asparagine, 0.55 mM L-Arginine, 1.5 mM L-Glutamine and 10% heat inactivated human AB serum). Half of the medium was replaced every other day by fresh culture medium containing 40 IU/ml IL-2 and 20 ng/ml IL-7, the 3rd and 4th week 40U/ml of IL-2 was replaced with 25 ng/ml IL-15. In the culture medium, peptides could also be added to the culture well at a final concentration of 1-2 µg/ml.

To evaluate the expansion of naive CTL, the Melan A/Mart-1 peptide (ELAGIGILTV (SEQ ID NO:110); Anaspec Inc, Calif.) was used as positive control peptide. CD8$^+$ Mart1 tetramer was stained with the specific APC-conjugated HLA-A*0201 tetramer (Beckman Coulter, Brea, Calif.) based on the manufacturer's instruction. Briefly, CTLs (5×10$^5$) were stained with the tetramer 10 µl for 30 min at room temperature and then washed with PBS, and finally stained with anti-human CD8-PE labeled antibody (BD Biosciences) for 30 min at 4° C. and analyzed by CyAn flow cytometry (Beckman Coulter, Inc).

3. Killing Assay

The cytotoxicity against target cells (882CSC and 1031CSC) by CTLs recognizing the peptides HER2p339, HER2p773, IL-13Rα2p345, and EphA2p883 was evaluated using DDAO-SE and cleaved caspase-3 method. 882CSC and 1031CSC were labeled with 1 µM Cell Trace™ Far Red DDAO-SE (Life Technologies, Grand Island, N.Y.) for 15 min at 37° C. and washed with PBS twice following the manufacturer's instructions. DDAO-SE labeled target cells were mixed with effector cells at a 1:10 ratio in round-bottom 96 well plate and incubated overnight at 37° C., 5% $CO_2$. The cells were washed, fixed, and permeabilized with Fix/Perm solution (BD Biosciences) and then stained for 30 minutes at 4° C. with 10 µl PE-labeled anti-cleaved caspase-3 monoclonal antibody, followed by Cyan flow cytometric analysis (Beckman Coulter, Inc).

Results: The results of the cytotoxicity studies against human cancer stem cell 882CSC and 1031 CSC indicated that HER2p339, HER2 p773, IL-13Rα2p345 and EphA2p883 peptide-specific CTLs can efficiently recognize and lyse 882CSC and 1031CSC target cells expressing these antigens epitopes of HER2p339, HERp773, IL-13Rα2p345 and EphA2p883.

Conclusion: The killing assay demonstrated that HER2 p773, IL-13Rα2p345 and EphA2p883 peptide-specific CTLs can efficiently recognize and lyse human ovarian cancer stem cells 882CSC and 1031CSC, and thus, supports the development of Exemplary Vaccine 1 to target human ovarian cancer cells and ovarian cancer stem cells.

Example 13

Microarray Dataset Analyses of ICT140 Gene Expression Profiles and the Correlation Between RNA Expression and Overall Survival (OS)

Objective: To compare gene expression of genes encoding the antigens from which the peptides in Exemplary Vaccine 1 are derived in human ovarian cancer and normal tissue from the TCGA microarray dataset and to determine whether the ICT140 gene expression is associated with poor overall survival (OS) in patients with high-grade serous ovarian cancer. Background: The goal of gene expression profiling studies is to identify gene expression signatures between tumor and normal tissue and to identify the correlation between gene expression and clinical outcome such as overall survival (OS) in order to discover potential biomarkers for treatment (e.g., for use as an immunotherapy target). Methods: The Cancer Genome Atlas (TCGA) project has analyzed mRNA expression, microRNA expression, promoter methylation, and DNA copy number in 586 high-grade serous ovarian cystadenocarcinoma that were profiled on the Affymetrix U133A platform and preprocessed with dChip (version Dec. 5, 2011) software as described in the manual (Nature, 2011:609; Proc Natl Acad Sci USA 2001; 9:31).

GSE9891 contains the expression data and clinical data of 285 ovarian cancer samples and has been deposited in the Gene Expression Omnibus (GEO) (GSE9891) (Clin Cancer Res 2008; 14:5198).

The microarray dataset was analyzed for the RNA expression of genes encoding antigens from which the peptides of the ICT140 vaccine are derived, in human ovarian cancer samples. In addition, this example compared the correlation between RNA expression and overall survival (OS) of ovarian cancer patients.

Gene expression analysis tools at tcga-data.nci.nih.gov/tcga/, cancergenome.nih.gov, and oncomine.org were used to examine the RNA expression of ICT140 genes in 586 human serous ovarian cancer samples in TCGA dataset.

The Kaplan-Meier method was used to estimate the correlation between RNA expression and overall survival (OS) and the log-rank test was employed to compare OS across group. All analyses were performed using the web-based Kaplan-Meier plotter tool (kmplot.com). The overall survival curves and the number-at-risk were indicated below the main plot. Hazard ratio (HR; and 95% confidence intervals) and log-rank P values were also calculated.

Figure 7:
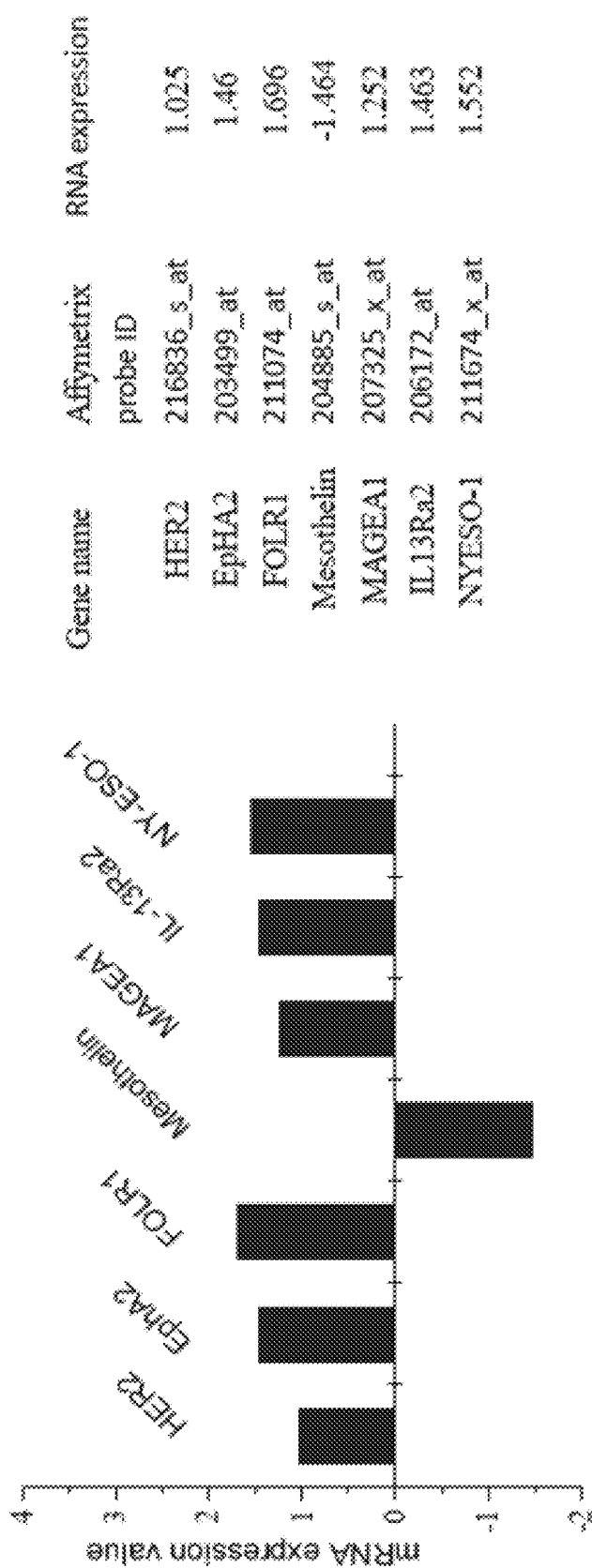
FIG. 7 is a bar graph showing RNA expression based on the TCGA dataset (586 patient samples) of the genes encoding antigens from which the peptides used in Exemplary Vaccine 1 were derived.
Figure 8A:
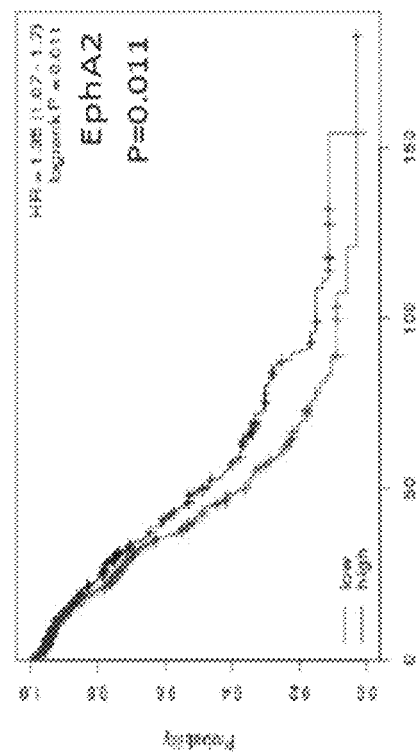
FIG. 8A is a graph depicting overall survival (OS) based on HER2 RNA expression in human ovarian cancer (Dataset: TCGA, 557 human ovarian cancer patients). The high expression curve is the bottom curve in the graph.
Figure 8B:
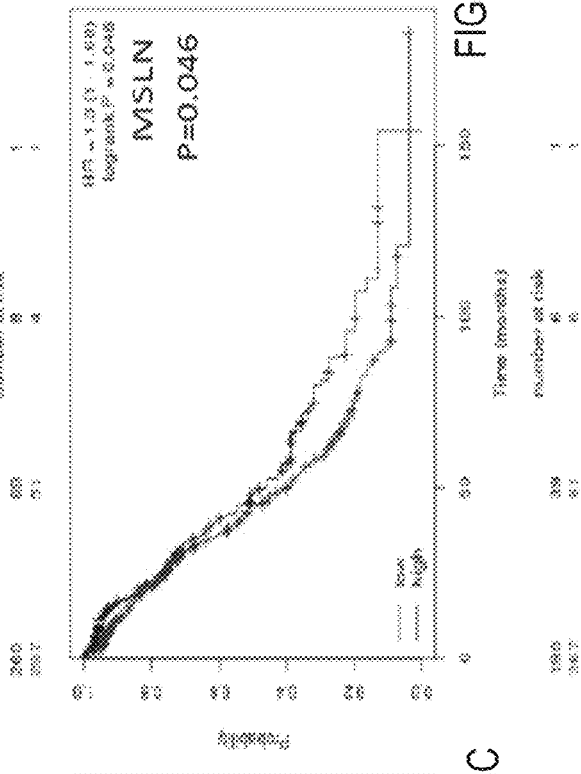
FIG. 8B is a graph depicting overall survival (OS) based on EphA2 RNA expression in human ovarian cancer (Dataset: TCGA, 557 human ovarian cancer patients). The high expression curve is the bottom curve in the graph.
Figure 8C:
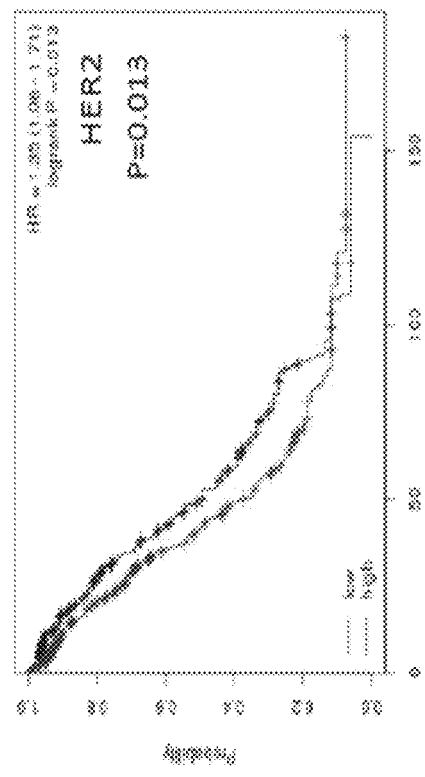
FIG. 8C is a graph depicting overall survival (OS) based on FOLR1 RNA expression in human ovarian cancer (Dataset: TCGA, 557 human ovarian cancer patients). The high expression curve is the upper curve in the graph.
Figure 8D:
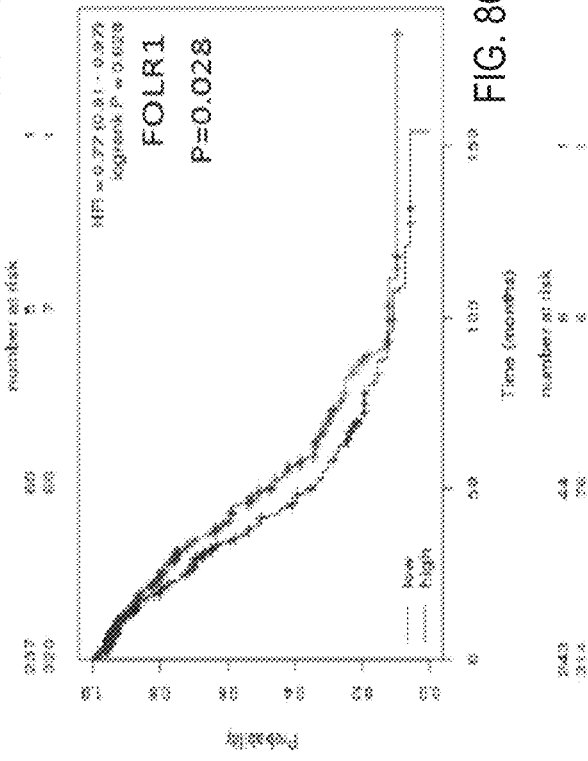
FIG. 8D is a graph depicting overall survival (OS) based on MSLN RNA expression in human ovarian cancer (Dataset: TCGA, 557 human ovarian cancer patients). The high expression curve is the bottom curve in the graph.
Figure 8E:
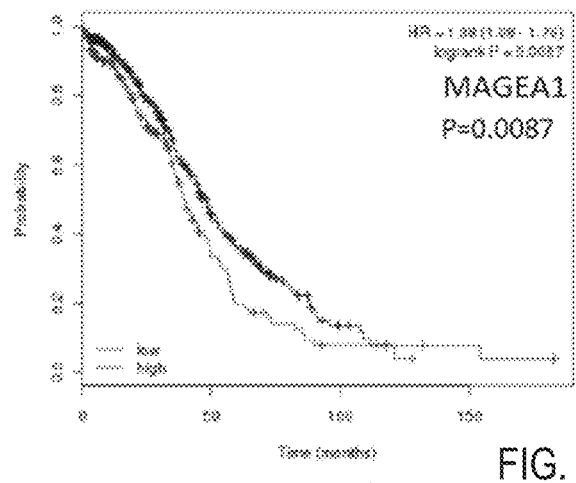
FIG. 8E is a graph depicting overall survival (OS) based on MAGE-A1 RNA expression in human ovarian cancer (Dataset: TCGA, 557 human ovarian cancer patients). The high expression curve is the bottom curve in the graph.
Figure 8F:
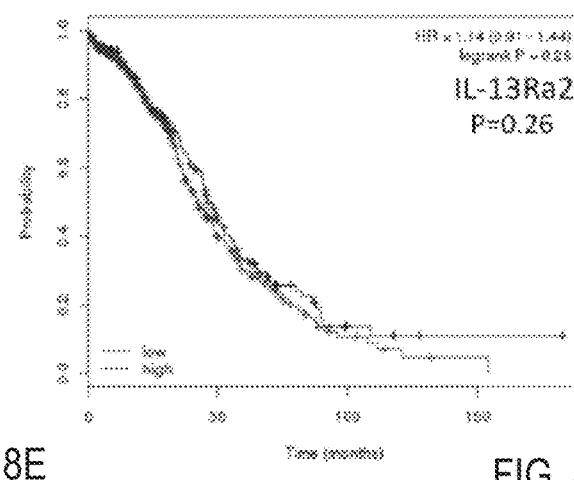
FIG. 8F is a graph depicting overall survival (OS) based on IL-13Rα2 RNA expression in human ovarian cancer (Dataset: TCGA, 557 human ovarian cancer patients). The high expression curve is the bottom curve in the graph.
Figure 8G:
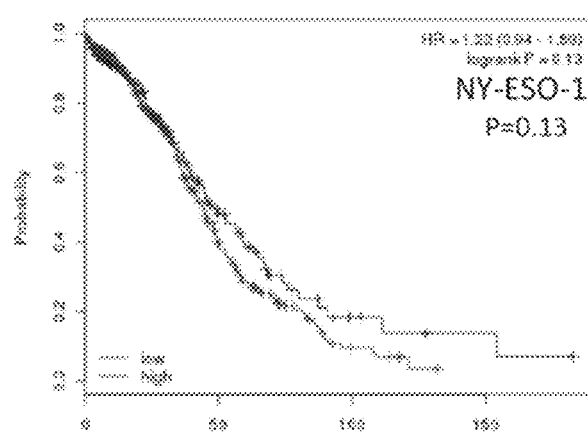
FIG. 8G is a graph depicting overall survival (OS) based on NY-ESO-1 RNA expression in human ovarian cancer (Dataset: TCGA, 557 human ovarian cancer patients). The high expression curve is the bottom curve in the graph.

Results: As shown in FIG. 7, the mRNA expression values of HER2, IL-13Rα2, MAGE-A1, EphA2, FOLR1, and NY-ESO-1in the TCGA ovarian cancer microarray dataset were 1.025, 1.463, 1.252, 1.46, 1.696, and 1.552, respectively, indicating that the expression of these gene in ovarian cancer tissue are higher than that in normal tissue. The expression value of mesothelin (MSLN) was −1.464, indicating that the expression of mesothelin in ovarian cancer tissue is lower than that in normal tissue.

The correlation between RNA expression of Exemplary Vaccine 1 genes (i.e., genes encoding proteins from which the Exemplary Vaccine 1 peptides are derived) and overall survival (OS) was evaluated in ovarian cancer patients using a TCGA microarray dataset. The analysis involved comparing survival in patient groups with "high" and 'low" RNA expression of these genes. For the TCGA dataset, the Kaplan-Meier results of overall survival (OS) with the patients "high" and "low" expression groups is shown in FIG. 8. The results in FIG. 8 show that patient groups with "high" RNA expression of genes HER2, EphA2, FOLR1, MSLN (mesothelin), and MAGE-A1 had poor overall survival (OS) with statistical significance (p<0.05), whereas, there was no significant difference between overall survival (OS) and the RNA expression of IL-13Rα2 and NY-ESO-1 genes.

In order to validate the correlation between overall survival (OS) and RNA expression of IL-13Rα2 and NY-ESO-1, we examined the GSE9891 dataset and found that patient groups with "high" RNA expression of IL-13Rα2 and NY-ESO-1 had poor overall survival (OS) (FIG. 9).

Conclusion: These findings demonstrate that HER2, EphA2, FOLR1, MSLN, MAGEA1, IL-13Rα2 and NY-ESO-1 (the genes encoding proteins from which the Exemplary Vaccine 1 peptides are derived) are associated with poor overall survival (OS) in patients with high-grade ovarian cancer based on TCGA and GSE9891 datasets. This data provides the basis for the rational design of novel treatment strategies including immunotherapy.

Example 14

IFN-γ ELISPOT Assay of the Antigen-Specific T Cell Response

Objective: To conduct an IFN-γ ELISPOT assay to determine the antigen-specific T cell response to HER2p339, and the three Exemplary Vaccine 1 peptides: HER2p743, Il-13Rα2p345, and EphA2p883

In order to develop a new generation of immunotherapy targets for ovarian cancer cells and ovarian cancer stem cells, we proposed the following antigens HLA-A2 peptides as potential targets. We hypothesize that ICT 140 HLA-A2 peptides could induce antigen-specific immune response.

To test this hypothesis, we isolated effector $CD8^+$ T cells and co-cultured with HLA-A2$^+$ DC pulsed with HER2 p339 and three ICT 140 peptides HER2p773, IL-13Rα2p345, EphA2p883 to induce antigen-specific CTLs. Then, we evaluated the antigen-specific T cell response in an IFN-γ ELISPOT assay.

Materials & Methods:
Generation of Human Dendritic Cells

Human monocyte-derived DC was generated using previously described methods. Briefly, monocytes were isolated from PBMC by magnetic immunoselection using EasySep human monocyte enrichment kit (Stem Cell Technologies) in accordance with the manufacturer's instructions and then cultured at $5 \times 10^7$/ml in 20 ml of GMP CellGenix DC serum-free medium (Cat #20801-0500, Cellgenix) supplemented with 1000 unit/ml of recombinant human GM-CSF (Cat #AF-300-03, Peprotech, Inc) and recombinant human IL-4 (Cat # AF-200-04, Peprotech, Inc). Cells were harvested after 3 or 6 days of culture. The DCs were washed and plated in 6-well plates at a concentration of $5 \times 10^6$ cells/well IFN-γ (1000 unit/ml) and monophosphoryl lipid A (MPLA, 20-50 μg/ml) was added into the wells to mature the DC for 24 hr or 48 hrs. Prior to some assays, DC was frozen and stored into liquid nitrogen.

CTL-induction and detection of Mart1-specific CD8+ by HLA-A*0201/Mart1 Tetramers In order to evaluate antigen-specific immune responses, $CD8^+$ T cells were isolated from fresh or frozen apheresis by positive selection using Dynabeads® CD8 Positive Isolation Kit (Life Technologies, Grand Island, N.Y.) and co-cultured with autologous mDC for four weeks. DCs were added weekly. Briefly, mDC was pulsed with synthetic peptides (10 m/μl) for 6-8 hours at 37° C., and then treated with 20 μg/ml Mitomycin C (Sigma-Aldrich, St. Louis, Mo.) for 25 min at 37° C. and 5% $CO_2$. The mDCs ($5 \times 10^4$ cells/well) were co-cultured with autologous $CD8^+$ T cells ($5 \times 10^5$ cells/well) in a 96-well plate at 37° C., 5% $CO_2$ in a final volume of 200 μl CTL medium (IMDM with 0.24 mM Asparagine, 0.55 mM L-Arginine, 1.5 mM L-Glutamine and 10% heat inactivated human AB serum). Half of the medium was replaced every other day by fresh culture medium containing 40 IU/ml IL-2 and 20 ng/ml IL-7, and in the 3rd and 4th week 40 IU/ml of IL-2 was replaced with 25 ng/ml of IL-15. Peptides also could be added to the culture well at a final concentration of 1-2 μg/ml.

IFN-γ ELISPOT Assay

Antigen-specific immune responses were evaluated by the IFN-γ Elispot kit (BD Biosciences) following previously described methods. Briefly, $1 \times 10^5$ CTL cells were co-cultured with $7.5 \times 10^4$ T2 cells pulsed with or without 10 μg/ml of peptides and seeded into 96-well plates for 20 hours. CTL cells without T2 cells and CTL plus 5 μg/ml PHA were set as negative and positive controls, respectively. The colored spots, representing cytokine-producing cells, were counted under a dissecting microscope. The results were evaluated by an automated ELISPOT reader system using KS ELISPOT 4.3 software.

Figure 10:
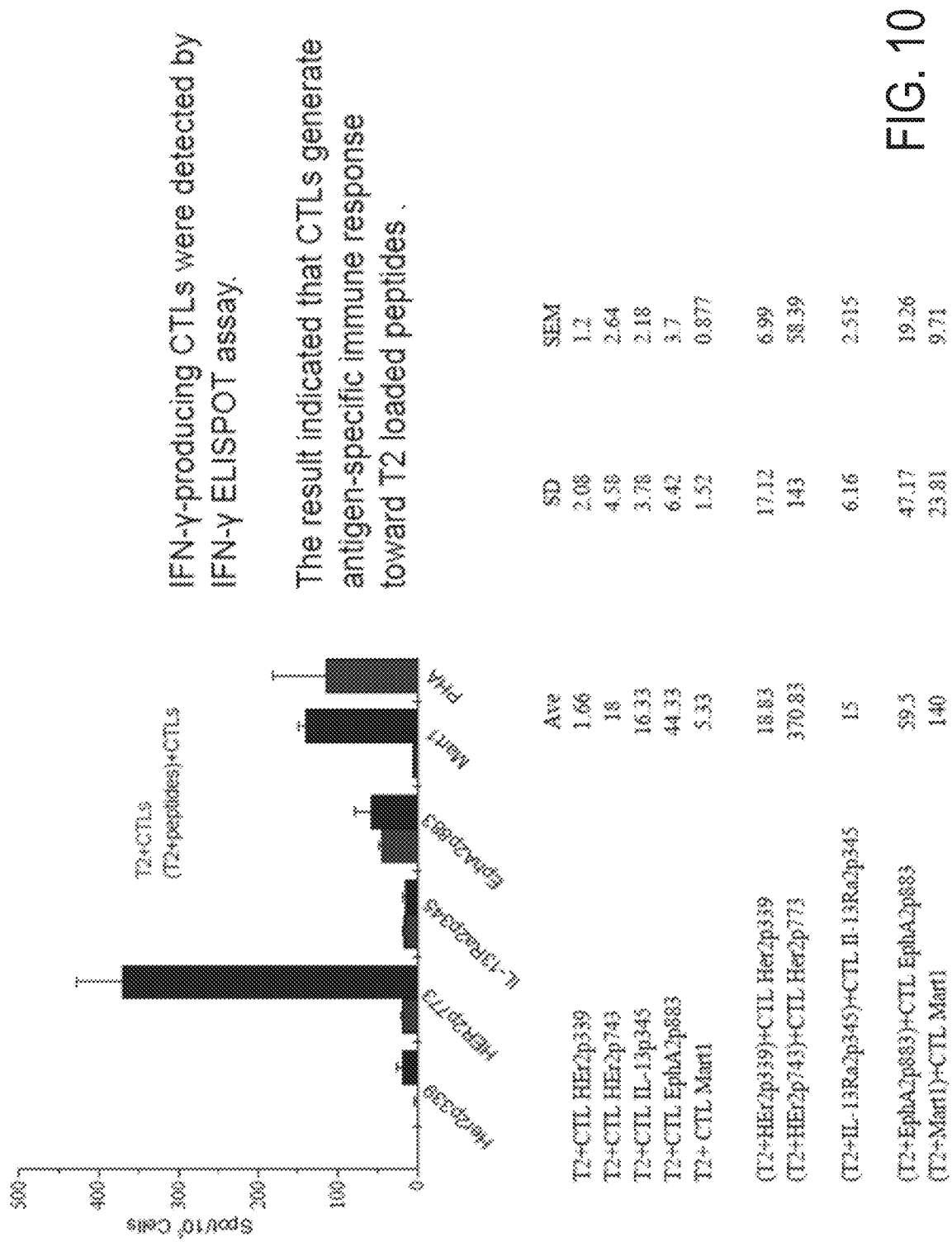
FIG. 10 is a bar graph showing the results of an IFN-γ ELISPOT assay of the antigen-specific T cell response to the T2 pulsed with HER2 p339 and three Exemplary Vaccine 1 peptides: HER2p773, IL-13Rα2p345, and EphA2p883.

Results: As shown in FIG. 10, CTLs produce more IFN-γ against T2 cell loaded with the peptides compared with T2 control (no peptides). The results of IFN-γ ELISPOT assay indicated that HER2p339 and ICT140 three peptides of HER2 p773, IL-13Rα2p345 and EphA2p883 peptides specific CTLs can efficiently recognize T2 pulsed with these antigens and boost the T cell immune response.

Conclusion: The IFN-γ ELISPOT assay demonstrated that HER2p339 peptides and Exemplary Vaccine 1 peptides HER2 p773, IL-13Rα2p345 and EphA2p883 peptides-specific CTLs can efficiently recognize these antigens containing epitopes and induce T2 cell immune response. This result forms the basis to further develop immunotherapy target for human ovarian cancer cells and ovarian cancer stem cells as well as ovarian cancer daughter cells.

Example 15

Evaluation of Cytotoxicity Against Human Ovarian Cancer Cells

Objective: To evaluate the cytotoxicity of CTLs, induced by the seven Exemplary Vaccine 1 HLA-A2 peptides on Exemplary Vaccine 1 peptide HLA-A2(+) human ovarian cancer cells.

Methods: Effector $CD8^+$ T cells are isolated and co-cultured with HLA-A2+ DC pulsed with the following seven Exemplary Vaccine 1 peptides: HER2 p773, IL-13Rα2 p345, EphA2 p883, FOLR1 p191, NY-ESO-1 p15'7, mesothelin p531, and MAGE-A1 p278 to induce antigen-specific CTLs. Next, cytotoxicity against HLA-A2+ ovarian cancer target cells is evaluated. The methods that will be used in the experiment are described in Example 12.

Other Embodiments

It is to be understood that while the invention has been described in conjunction with the detailed description thereof, the foregoing description is intended to illustrate and not limit the scope of the disclosure. Other aspects, advantages, and modifications are within the scope of the following claims.

What is claimed is:

1. A method of treating a gynecological or a peritoneal cancer, the method comprising administering to a subject having a gynecological or a peritoneal cancer an effective amount of a composition comprising a pharmaceutically acceptable carrier, an adjuvant, and a mixture of at least one major histocompatibility complex (MHC) class I peptide epitope of 8-10 amino acids in length derived from a mesothelin antigen variant having an amino acid sequence selected from the group consisting of: SEQ ID NOs: 19-25 and at least one MHC class I peptide epitope of 8-10 amino acids in length derived from each of at least six different antigens or variants thereof selected from the group consisting of:

a mesothelin antigen, wherein the MHC class I peptide epitope has an amino acid sequence selected from the group consisting of SEQ ID NOs: 15-18;

an NY-ESO-1 antigen, wherein the MHC class I peptide epitope has an amino acid sequence selected from the group consisting of SEQ ID NO: 26 and SEQ ID NO: 27;

an FBP antigen, wherein the MHC class I peptide epitope has an amino acid sequence selected from the group consisting of SEQ ID NO: 28 and SEQ ID NO: 29;

a HER-2/neu antigen, wherein the MHC class I peptide epitope has an amino acid sequence selected from the group consisting of SEQ ID NOs: 30-48;

an IL-13 receptor α2 antigen, wherein the MHC class I peptide epitope has an amino acid sequence of SEQ ID NO: 49;

a MAGE-A1 antigen, wherein the MHC class I peptide epitope has an amino acid sequence selected from the group consisting of SEQ ID NOs: 50-55;

an EphA2 antigen, wherein the MHC class I peptide epitope has an amino acid sequence selected from the group consisting of SEQ ID NOs: 56-68;
a p53 antigen or variant thereof, wherein the MHC class I peptide epitope has an amino acid sequence selected from the group consisting of SEQ ID NOs:69-80;
a k-Ras antigen or variant thereof, wherein the MHC class I peptide epitope has an amino acid sequence selected from the group consisting of SEQ ID NOs:81-86;
an Ep-CAM antigen, wherein the MHC class I peptide epitope has an amino acid sequence selected from the group consisting of SEQ ID NOs:87-91;
a MUC1 antigen or variant thereof, wherein the MHC class I peptide epitope has an amino acid sequence selected from the group consisting of SEQ ID NO:92 and SEQ ID NO:93;
a survivin antigen or variant thereof, wherein the MHC class I peptide epitope has an amino acid sequence selected from the group consisting of SEQ ID NOs: 94-98;
an hTERT antigen or variant thereof, wherein the MHC class I peptide epitope has an amino acid sequence selected from the group consisting of SEQ ID NOs: 99-104; and
a WT1 antigen, wherein the MHC class I peptide epitope has an amino acid sequence selected from the group consisting of SEQ ID NOs: 105-109,
wherein said gynecological or said peritoneal cancer expresses at least one of mesothelin, NY-ESO-1, FBP, HER-2/neu, IL-13 receptor α2, MAGE-A1, EphA2, p53, k-Ras, Ep-CAM, MUC1, survivin, hTERT, and WT1.

2. The method of claim 1, wherein the gynecological cancer is an epithelial ovarian cancer or a fallopian tube cancer.

3. The method of claim 1, wherein the peritoneal cancer is a primary peritoneal cancer.

4. The method of claim 1, further comprising administering a chemotherapeutic agent to the subject prior to, at the same time as, or subsequent to administering the composition to the subject.

5. The method of claim 4, wherein the chemotherapeutic agent is administered to the subject 1 day prior to or subsequent to administering the composition to the subject.

6. The method of claim 4, wherein the chemotherapeutic agent is cyclophosphamide.

7. The method of claim 1, wherein the subject is an HLA-A2$^+$ human.

8. The method of claim 1, wherein the composition further comprises at least one MHC class II peptide epitope.

9. The method of claim 1, wherein the composition further comprises any one of dextrose, dimethyl sulfoxide (DMSO), and dextran.

10. The method of claim 1, wherein the composition comprises at least one MHC class I peptide epitope of 8-10 amino acids in length derived from a mesothelin antigen, an NY-ESO-1 antigen, an FBP antigen, a HER-2/neu antigen, an IL-13 receptor α2 antigen, a MAGE-A 1 antigen, and an EphA2 antigen.

11. The method of claim 1, wherein the composition comprises:
the MHC class I peptide epitope derived from an NY-ESO-1 antigen having the amino acid sequence of SEQ ID NO: 26;
the MHC class I peptide epitope derived from an FBP antigen having the amino acid sequence of SEQ ID NO: 28;
the MHC class I peptide epitope derived from a HER-2/neu antigen having the amino acid sequence of SEQ ID NO: 40;
the MHC class I peptide epitope derived from a IL-13 receptor α2 antigen having the amino acid sequence of SEQ ID NO: 49;
the MHC class I peptide epitope derived from a MAGE-A1 antigen having the amino acid sequence of SEQ ID NO: 55; and
the MHC class I peptide epitope derived from an EphA2 antigen having the amino acid sequence of SEQ ID NO: 66.

12. The method of claim 1, wherein each of the MHC class I peptide epitopes is present in the composition at a concentration between about 10 μg/ml and about 20 μg/ml.

13. The method of claim 1, wherein each of the MHC class I peptide epitopes is present in the composition at a concentration of 20 μg/ml.

14. The method of claim 1, wherein each of the MHC class I peptide epitopes is present in the composition at a concentration of 2 μg/ml.

15. The method of claim 1, wherein each of the MHC class I peptide epitopes is pegylated.

16. The method of claim 1, wherein the composition comprises at least eight epitopes derived from each of eight of said different antigens or variants thereof.

17. The method of claim 1, wherein the composition comprises at least seven of said MHC class I peptide epitopes derived from each of said mesothelin antigen, said NY-ESO-1 antigen, said FBP antigen, said HER-2/neu antigen, said IL-13 receptor α2 antigen, said MAGE-A1 antigen, and said EphA2 antigen.

18. The method of claim 11, wherein the composition comprises the MHC class I peptide epitope derived from an mesothelin antigen having the amino acid sequence of SEQ ID NO: 15 or SEQ ID NO: 17.

* * * * *

SEQUENCE LISTING

<160> NUMBER OF SEQ ID NOS: 114

<210> SEQ ID NO 1
<211> LENGTH: 622
<212> TYPE: PRT

<213> ORGANISM: Homo sapiens

<400> SEQUENCE: 1

```
Met Ala Leu Pro Thr Ala Arg Pro Leu Leu Gly Ser Cys Gly Thr Pro
1               5                   10                  15
Ala Leu Gly Ser Leu Leu Phe Leu Leu Phe Ser Leu Gly Trp Val Gln
            20                  25                  30
Pro Ser Arg Thr Leu Ala Gly Glu Thr Gly Gln Glu Ala Ala Pro Leu
        35                  40                  45
Asp Gly Val Leu Ala Asn Pro Pro Asn Ile Ser Ser Leu Ser Pro Arg
    50                  55                  60
Gln Leu Leu Gly Phe Pro Cys Ala Glu Val Ser Gly Leu Ser Thr Glu
65                  70                  75                  80
Arg Val Arg Glu Leu Ala Val Ala Leu Ala Gln Lys Asn Val Lys Leu
                85                  90                  95
Ser Thr Glu Gln Leu Arg Cys Leu Ala His Arg Leu Ser Glu Pro Pro
            100                 105                 110
Glu Asp Leu Asp Ala Leu Pro Leu Asp Leu Leu Leu Phe Leu Asn Pro
        115                 120                 125
Asp Ala Phe Ser Gly Pro Gln Ala Cys Thr Arg Phe Phe Ser Arg Ile
130                 135                 140
Thr Lys Ala Asn Val Asp Leu Leu Pro Arg Gly Ala Pro Glu Arg Gln
145                 150                 155                 160
Arg Leu Leu Pro Ala Ala Leu Ala Cys Trp Gly Val Arg Gly Ser Leu
                165                 170                 175
Leu Ser Glu Ala Asp Val Arg Ala Leu Gly Gly Leu Ala Cys Asp Leu
            180                 185                 190
Pro Gly Arg Phe Val Ala Glu Ser Ala Glu Val Leu Leu Pro Arg Leu
        195                 200                 205
Val Ser Cys Pro Gly Pro Leu Asp Gln Asp Gln Gln Glu Ala Ala Arg
    210                 215                 220
Ala Ala Leu Gln Gly Gly Gly Pro Pro Tyr Gly Pro Pro Ser Thr Trp
225                 230                 235                 240
Ser Val Ser Thr Met Asp Ala Leu Arg Gly Leu Leu Pro Val Leu Gly
                245                 250                 255
Gln Pro Ile Ile Arg Ser Ile Pro Gln Gly Ile Val Ala Ala Trp Arg
            260                 265                 270
Gln Arg Ser Ser Arg Asp Pro Ser Trp Arg Gln Pro Glu Arg Thr Ile
        275                 280                 285
Leu Arg Pro Arg Phe Arg Arg Glu Val Glu Lys Thr Ala Cys Pro Ser
    290                 295                 300
Gly Lys Lys Ala Arg Glu Ile Asp Glu Ser Leu Ile Phe Tyr Lys Lys
305                 310                 315                 320
Trp Glu Leu Glu Ala Cys Val Asp Ala Ala Leu Leu Ala Thr Gln Met
                325                 330                 335
Asp Arg Val Asn Ala Ile Pro Phe Thr Tyr Glu Gln Leu Asp Val Leu
            340                 345                 350
Lys His Lys Leu Asp Glu Leu Tyr Pro Gln Gly Tyr Pro Glu Ser Val
        355                 360                 365
Ile Gln His Leu Gly Tyr Leu Phe Leu Lys Met Ser Pro Glu Asp Ile
    370                 375                 380
Arg Lys Trp Asn Val Thr Ser Leu Glu Thr Leu Lys Ala Leu Leu Glu
385                 390                 395                 400
```

-continued

Val Asn Lys Gly His Glu Met Ser Pro Gln Val Ala Thr Leu Ile Asp
                     405                 410                 415

Arg Phe Val Lys Gly Arg Gly Gln Leu Asp Lys Asp Thr Leu Asp Thr
             420                 425                 430

Leu Thr Ala Phe Tyr Pro Gly Tyr Leu Cys Ser Leu Ser Pro Glu Glu
         435                 440                 445

Leu Ser Ser Val Pro Pro Ser Ser Ile Trp Ala Val Arg Pro Gln Asp
     450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
             500                 505                 510

Gln Gln Asn Val Ser Met Asp Leu Ala Thr Phe Met Lys Leu Arg Thr
         515                 520                 525

Asp Ala Val Leu Pro Leu Thr Val Ala Glu Val Gln Lys Leu Leu Gly
     530                 535                 540

Pro His Val Glu Gly Leu Lys Ala Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
             580                 585                 590

Met Gln Glu Ala Leu Ser Gly Thr Pro Cys Leu Leu Gly Pro Gly Pro
         595                 600                 605

Val Leu Thr Val Leu Ala Leu Leu Ala Ser Thr Leu Ala
     610                 615                 620

<210> SEQ ID NO 2
<211> LENGTH: 180
<212> TYPE: PRT
<213> ORGANISM: Homo sapiens

<400> SEQUENCE: 2

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

```
Trp Ile Thr Gln Cys Phe Leu Pro Val Phe Leu Ala Gln Pro Pro Ser
                165                 170                 175

Gly Gln Arg Arg
            180

<210> SEQ ID NO 3
<211> LENGTH: 257
<212> TYPE: PRT
<213> ORGANISM: Homo sapiens

<400> SEQUENCE: 3

Met Ala Gln Arg Met Thr Thr Gln Leu Leu Leu Leu Val Trp Val
1               5                   10                  15

Ala Val Val Gly Glu Ala Gln Thr Arg Ile Ala Trp Ala Arg Thr Glu
                20                  25                  30

Leu Leu Asn Val Cys Met Asn Ala Lys His His Lys Glu Lys Pro Gly
                35                  40                  45

Pro Glu Asp Lys Leu His Glu Gln Cys Arg Pro Trp Arg Lys Asn Ala
            50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
                100                 105                 110

Leu Gly Pro Trp Ile Gln Gln Val Asp Gln Ser Trp Arg Lys Glu Arg
            115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
            195                 200                 205

Cys Ile Gln Met Trp Phe Asp Pro Ala Gln Gly Asn Pro Asn Glu Glu
        210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 4
<211> LENGTH: 1255
<212> TYPE: PRT
<213> ORGANISM: Homo sapiens

<400> SEQUENCE: 4

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30
```

-continued

Leu Arg Leu Pro Ala Ser Pro Glu Thr His Leu Asp Met Leu Arg His
         35                  40                  45

Leu Tyr Gln Gly Cys Gln Val Val Gln Gly Asn Leu Glu Leu Thr Tyr
 50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
             100                 105                 110

Ala Leu Ala Val Leu Asp Asn Gly Asp Pro Leu Asn Asn Thr Thr Pro
             115                 120                 125

Val Thr Gly Ala Ser Pro Gly Gly Leu Arg Glu Leu Gln Leu Arg Ser
         130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                 165                 170                 175

Asn Gln Leu Ala Leu Thr Leu Ile Asp Thr Asn Arg Ser Arg Ala Cys
             180                 185                 190

His Pro Cys Ser Pro Met Cys Lys Gly Ser Arg Cys Trp Gly Glu Ser
         195                 200                 205

Ser Glu Asp Cys Gln Ser Leu Thr Arg Thr Val Cys Ala Gly Gly Cys
         210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                 245                 250                 255

His Phe Asn His Ser Gly Ile Cys Glu Leu His Cys Pro Ala Leu Val
             260                 265                 270

Thr Tyr Asn Thr Asp Thr Phe Glu Ser Met Pro Asn Pro Glu Gly Arg
         275                 280                 285

Tyr Thr Phe Gly Ala Ser Cys Val Thr Ala Cys Pro Tyr Asn Tyr Leu
         290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                 325                 330                 335

Pro Cys Ala Arg Val Cys Tyr Gly Leu Gly Met Glu His Leu Arg Glu
             340                 345                 350

Val Arg Ala Val Thr Ser Ala Asn Ile Gln Glu Phe Ala Gly Cys Lys
         355                 360                 365

Lys Ile Phe Gly Ser Leu Ala Phe Leu Pro Glu Ser Phe Asp Gly Asp
 370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                 405                 410                 415

Asp Ser Leu Pro Asp Leu Ser Val Phe Gln Asn Leu Gln Val Ile Arg
             420                 425                 430

Gly Arg Ile Leu His Asn Gly Ala Tyr Ser Leu Thr Leu Gln Gly Leu
         435                 440                 445

Gly Ile Ser Trp Leu Gly Leu Arg Ser Leu Arg Glu Leu Gly Ser Gly

```
                   450                 455                 460
Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                    485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
                515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
                595                 600                 605

Ser Tyr Met Pro Ile Trp Lys Phe Pro Asp Glu Glu Gly Ala Cys Gln
610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
                660                 665                 670

Ile Leu Ile Lys Arg Arg Gln Gln Lys Ile Arg Lys Tyr Thr Met Arg
                675                 680                 685

Arg Leu Leu Gln Glu Thr Glu Leu Val Glu Pro Leu Thr Pro Ser Gly
                690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
                740                 745                 750

Lys Val Leu Arg Glu Asn Thr Ser Pro Lys Ala Asn Lys Glu Ile Leu
                755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
                820                 825                 830

Met Ser Tyr Leu Glu Asp Val Arg Leu Val His Arg Asp Leu Ala Ala
                835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880
```

```
Gly Gly Lys Val Pro Ile Lys Trp Met Ala Leu Glu Ser Ile Leu Arg
            885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
        930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 5
<211> LENGTH: 380
```

<212> TYPE: PRT
<213> ORGANISM: Homo sapiens

<400> SEQUENCE: 5

Met Ala Phe Val Cys Leu Ala Ile Gly Cys Leu Tyr Thr Phe Leu Ile
1               5                   10                  15

Ser Thr Thr Phe Gly Cys Thr Ser Ser Asp Thr Glu Ile Lys Val
            20                  25                  30

Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
        115                 120                 125

Trp Ile Ser Pro Gln Gly Ile Pro Glu Thr Lys Val Gln Asp Met Asp
    130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
    210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
    275                 280                 285

Glu Asn Glu Thr Tyr Thr Leu Lys Thr Thr Asn Glu Thr Arg Gln Leu
290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Thr Leu Leu Arg Phe Trp Leu Pro Phe Gly Phe Ile Leu
            340                 345                 350

Ile Leu Val Ile Phe Val Thr Gly Leu Leu Leu Arg Lys Pro Asn Thr
        355                 360                 365

Tyr Pro Lys Met Ile Pro Glu Phe Phe Cys Asp Thr
    370                 375                 380

<210> SEQ ID NO 6

<211> LENGTH: 309
<212> TYPE: PRT
<213> ORGANISM: Homo sapiens

<400> SEQUENCE: 6

```
Met Ser Leu Glu Gln Arg Ser Leu His Cys Lys Pro Glu Glu Ala Leu
1               5                   10                  15

Glu Ala Gln Gln Glu Ala Leu Gly Leu Val Cys Val Gln Ala Ala Thr
            20                  25                  30

Ser Ser Ser Ser Pro Leu Val Leu Gly Thr Leu Glu Glu Val Pro Thr
        35                  40                  45

Ala Gly Ser Thr Asp Pro Pro Gln Ser Pro Gln Gly Ala Ser Ala Phe
    50                  55                  60

Pro Thr Thr Ile Asn Phe Thr Arg Gln Arg Gln Pro Ser Glu Gly Ser
65                  70                  75                  80

Ser Ser Arg Glu Glu Glu Gly Pro Ser Thr Ser Cys Ile Leu Glu Ser
                85                  90                  95

Leu Phe Arg Ala Val Ile Thr Lys Lys Val Ala Asp Leu Val Gly Phe
            100                 105                 110

Leu Leu Leu Lys Tyr Arg Ala Arg Glu Pro Val Thr Lys Ala Glu Met
        115                 120                 125

Leu Glu Ser Val Ile Lys Asn Tyr Lys His Cys Phe Pro Glu Ile Phe
    130                 135                 140

Gly Lys Ala Ser Glu Ser Leu Gln Leu Val Phe Gly Ile Asp Val Lys
145                 150                 155                 160

Glu Ala Asp Pro Thr Gly His Ser Tyr Val Leu Val Thr Cys Leu Gly
                165                 170                 175

Leu Ser Tyr Asp Gly Leu Leu Gly Asp Asn Gln Ile Met Pro Lys Thr
            180                 185                 190

Gly Phe Leu Ile Ile Val Leu Val Met Ile Ala Met Glu Gly Gly His
        195                 200                 205

Ala Pro Glu Glu Glu Ile Trp Glu Glu Leu Ser Val Met Glu Val Tyr
    210                 215                 220

Asp Gly Arg Glu His Ser Ala Tyr Gly Glu Pro Arg Lys Leu Leu Thr
225                 230                 235                 240

Gln Asp Leu Val Gln Glu Lys Tyr Leu Glu Tyr Arg Gln Val Pro Asp
                245                 250                 255

Ser Asp Pro Ala Arg Tyr Glu Phe Leu Trp Gly Pro Arg Ala Leu Ala
            260                 265                 270

Glu Thr Ser Tyr Val Lys Val Leu Glu Tyr Val Ile Lys Val Ser Ala
        275                 280                 285

Arg Val Arg Phe Phe Phe Pro Ser Leu Arg Glu Ala Ala Leu Arg Glu
    290                 295                 300

Glu Glu Glu Gly Val
305
```

<210> SEQ ID NO 7
<211> LENGTH: 976
<212> TYPE: PRT
<213> ORGANISM: Homo sapiens

<400> SEQUENCE: 7

```
Met Glu Leu Gln Ala Ala Arg Ala Cys Phe Ala Leu Leu Trp Gly Cys
1               5                   10                  15

Ala Leu Ala Ala Ala Ala Ala Ala Gln Gly Lys Glu Val Val Leu Leu
            20                  25                  30
```

```
Asp Phe Ala Ala Ala Gly Gly Glu Leu Gly Trp Leu Thr His Pro Tyr
         35                  40                  45

Gly Lys Gly Trp Asp Leu Met Gln Asn Ile Met Asn Asp Met Pro Ile
     50                  55                  60

Tyr Met Tyr Ser Val Cys Asn Val Met Ser Gly Asp Gln Asp Asn Trp
 65                  70                  75                  80

Leu Arg Thr Asn Trp Val Tyr Arg Gly Glu Ala Glu Arg Ile Phe Ile
                 85                  90                  95

Glu Leu Lys Phe Thr Val Arg Asp Cys Asn Ser Phe Pro Gly Gly Ala
             100                 105                 110

Ser Ser Cys Lys Glu Thr Phe Asn Leu Tyr Tyr Ala Glu Ser Asp Leu
         115                 120                 125

Asp Tyr Gly Thr Asn Phe Gln Lys Arg Leu Phe Thr Lys Ile Asp Thr
     130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                 165                 170                 175

Gly Phe Tyr Leu Ala Phe Gln Asp Ile Gly Ala Cys Val Ala Leu Leu
             180                 185                 190

Ser Val Arg Val Tyr Tyr Lys Lys Cys Pro Glu Leu Leu Gln Gly Leu
         195                 200                 205

Ala His Phe Pro Glu Thr Ile Ala Gly Ser Asp Ala Pro Ser Leu Ala
     210                 215                 220

Thr Val Ala Gly Thr Cys Val Asp His Ala Val Pro Pro Gly Gly Gly
225                 230                 235                 240

Glu Glu Pro Arg Met His Cys Ala Val Asp Gly Glu Trp Leu Val Pro
                 245                 250                 255

Ile Gly Gln Cys Leu Cys Gln Ala Gly Tyr Glu Lys Val Glu Asp Ala
             260                 265                 270

Cys Gln Ala Cys Ser Pro Gly Phe Phe Lys Phe Glu Ala Ser Glu Ser
         275                 280                 285

Pro Cys Leu Glu Cys Pro Glu His Thr Leu Pro Ser Pro Glu Gly Ala
     290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
                 325                 330                 335

Ala Val Gly Met Gly Ala Lys Val Glu Leu Arg Trp Thr Pro Pro Gln
             340                 345                 350

Asp Ser Gly Gly Arg Glu Asp Ile Val Tyr Ser Val Thr Cys Glu Gln
         355                 360                 365

Cys Trp Pro Glu Ser Gly Glu Cys Gly Pro Cys Glu Ala Ser Val Arg
     370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                 405                 410                 415

Gly Val Ser Gly Leu Val Thr Ser Arg Ser Phe Arg Thr Ala Ser Val
             420                 425                 430

Ser Ile Asn Gln Thr Glu Pro Pro Lys Val Arg Leu Glu Gly Arg Ser
         435                 440                 445
```

```
Thr Thr Ser Leu Ser Val Ser Trp Ser Ile Pro Pro Gln Gln Ser
    450                 455                 460

Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
                485                 490                 495

Leu Ala Pro Asp Thr Thr Tyr Leu Val Gln Val Gln Ala Leu Thr Gln
            500                 505                 510

Glu Gly Gln Gly Ala Gly Ser Lys Val His Glu Phe Gln Thr Leu Ser
        515                 520                 525

Pro Glu Gly Ser Gly Asn Leu Ala Val Ile Gly Gly Val Ala Val Gly
    530                 535                 540

Val Val Leu Leu Leu Val Leu Ala Gly Val Gly Phe Ile His Arg
545                 550                 555                 560

Arg Arg Lys Asn Gln Arg Ala Arg Gln Ser Pro Glu Asp Val Tyr Phe
                565                 570                 575

Ser Lys Ser Glu Gln Leu Lys Pro Leu Lys Thr Tyr Val Asp Pro His
            580                 585                 590

Thr Tyr Glu Asp Pro Asn Gln Ala Val Leu Lys Phe Thr Thr Glu Ile
        595                 600                 605

His Pro Ser Cys Val Thr Arg Gln Lys Val Ile Gly Ala Gly Glu Phe
    610                 615                 620

Gly Glu Val Tyr Lys Gly Met Leu Lys Thr Ser Ser Gly Lys Lys Glu
625                 630                 635                 640

Val Pro Val Ala Ile Lys Thr Leu Lys Ala Gly Tyr Thr Glu Lys Gln
                645                 650                 655

Arg Val Asp Phe Leu Gly Glu Ala Gly Ile Met Gly Gln Phe Ser His
            660                 665                 670

His Asn Ile Ile Arg Leu Glu Gly Val Ile Ser Lys Tyr Lys Pro Met
        675                 680                 685

Met Ile Ile Thr Glu Tyr Met Glu Asn Gly Ala Leu Asp Lys Phe Leu
    690                 695                 700

Arg Glu Lys Asp Gly Glu Phe Ser Val Leu Gln Leu Val Gly Met Leu
705                 710                 715                 720

Arg Gly Ile Ala Ala Gly Met Lys Tyr Leu Ala Asn Met Asn Tyr Val
                725                 730                 735

His Arg Asp Leu Ala Ala Arg Asn Ile Leu Val Asn Ser Asn Leu Val
            740                 745                 750

Cys Lys Val Ser Asp Phe Gly Leu Ser Arg Val Leu Glu Asp Asp Pro
        755                 760                 765

Glu Ala Thr Tyr Thr Thr Ser Gly Gly Lys Ile Pro Ile Arg Trp Thr
    770                 775                 780

Ala Pro Glu Ala Ile Ser Tyr Arg Lys Phe Thr Ser Ala Ser Asp Val
785                 790                 795                 800

Trp Ser Phe Gly Ile Val Met Trp Glu Val Met Thr Tyr Gly Glu Arg
                805                 810                 815

Pro Tyr Trp Glu Leu Ser Asn His Glu Val Met Lys Ala Ile Asn Asp
            820                 825                 830

Gly Phe Arg Leu Pro Thr Pro Met Asp Cys Pro Ser Ala Ile Tyr Gln
        835                 840                 845

Leu Met Met Gln Cys Trp Gln Gln Glu Arg Ala Arg Arg Pro Lys Phe
    850                 855                 860

Ala Asp Ile Val Ser Ile Leu Asp Lys Leu Ile Arg Ala Pro Asp Ser
```

Leu Lys Thr Leu Ala Asp Phe Asp Pro Arg Val Ser Ile Arg Leu Pro
            885                 890                 895

Ser Thr Ser Gly Ser Glu Gly Val Pro Phe Arg Thr Val Ser Glu Trp
            900                 905                 910

Leu Glu Ser Ile Lys Met Gln Tyr Thr Glu His Phe Met Ala Ala
            915                 920                 925

Gly Tyr Thr Ala Ile Glu Lys Val Val Gln Met Thr Asn Asp Asp Ile
            930                 935                 940

Lys Arg Ile Gly Val Arg Leu Pro Gly His Gln Lys Arg Ile Ala Tyr
945                 950                 955                 960

Ser Leu Leu Gly Leu Lys Asp Gln Val Asn Thr Val Gly Ile Pro Ile
            965                 970                 975

<210> SEQ ID NO 8
<211> LENGTH: 393
<212> TYPE: PRT
<213> ORGANISM: Homo sapiens

<400> SEQUENCE: 8

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
            85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
            130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
            165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
            195                 200                 205

Arg Asn Thr Phe Arg His Ser Val Val Val Pro Tyr Glu Pro Pro Glu
            210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
            245                 250                 255

Leu Glu Asp Ser Ser Gly Asn Leu Leu Gly Arg Asn Ser Phe Glu Val
            260                 265                 270

```
Arg Val Cys Ala Cys Pro Gly Arg Asp Arg Arg Thr Glu Glu Glu Asn
            275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Pro Gln Pro Lys Lys
305                 310                 315                 320

Lys Pro Leu Asp Gly Glu Tyr Phe Thr Leu Gln Ile Arg Gly Arg Glu
            325                 330                 335

Arg Phe Glu Met Phe Arg Glu Leu Asn Glu Ala Leu Glu Leu Lys Asp
                340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
370                 375                 380

Phe Lys Thr Glu Gly Pro Asp Ser Asp
385                 390
```

<210> SEQ ID NO 9
<211> LENGTH: 188
<212> TYPE: PRT
<213> ORGANISM: Homo sapiens

<400> SEQUENCE: 9

```
Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

<210> SEQ ID NO 10
<211> LENGTH: 314
<212> TYPE: PRT
<213> ORGANISM: Homo sapiens

<400> SEQUENCE: 10

```
Met Ala Pro Pro Gln Val Leu Ala Phe Gly Leu Leu Leu Ala Ala Ala
1               5                   10                  15
```

Thr Ala Thr Phe Ala Ala Ala Gln Glu Glu Cys Val Cys Glu Asn Tyr
                20                  25                  30

Lys Leu Ala Val Asn Cys Phe Val Asn Asn Arg Gln Cys Gln Cys
            35                  40                  45

Thr Ser Val Gly Ala Gln Asn Thr Val Ile Cys Ser Lys Leu Ala Ala
        50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
            100                 105                 110

Thr Ser Met Cys Trp Cys Val Asn Thr Ala Gly Val Arg Arg Thr Asp
        115                 120                 125

Lys Asp Thr Glu Ile Thr Cys Ser Glu Arg Val Arg Thr Tyr Trp Ile
130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
        195                 200                 205

Ile Ala Asp Val Ala Tyr Tyr Phe Glu Lys Asp Val Lys Gly Glu Ser
210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys Ala Gly Val Ile Ala Val Ile
            260                 265                 270

Val Val Val Val Ile Ala Val Val Ala Gly Ile Val Val Leu Val Ile
        275                 280                 285

Ser Arg Lys Lys Arg Met Ala Lys Tyr Glu Lys Ala Glu Ile Lys Glu
290                 295                 300

Met Gly Glu Met His Arg Glu Leu Asn Ala
305                 310

<210> SEQ ID NO 11
<211> LENGTH: 264
<212> TYPE: PRT
<213> ORGANISM: Homo sapiens

<400> SEQUENCE: 11

Met Thr Pro Gly Thr Gln Ser Pro Phe Phe Leu Leu Leu Leu Leu Thr
1               5                   10                  15

Val Leu Thr Ala Thr Thr Ala Pro Lys Pro Ala Thr Val Val Thr Gly
                20                  25                  30

Ser Gly His Ala Ser Ser Thr Pro Gly Gly Lys Glu Thr Ser Ala
            35                  40                  45

Thr Gln Arg Ser Ser Val Pro Ser Ser Thr Glu Lys Asn Ala Phe Asn
        50                  55                  60

Ser Ser Leu Glu Asp Pro Ser Thr Asp Tyr Tyr Gln Glu Leu Gln Arg
65                  70                  75                  80

```
Asp Ile Ser Glu Met Phe Leu Gln Ile Tyr Lys Gln Gly Gly Phe Leu
                85                  90                  95

Gly Leu Ser Asn Ile Lys Phe Arg Pro Gly Ser Val Val Gln Leu
                100                 105                 110

Thr Leu Ala Phe Arg Glu Gly Thr Ile Asn Val His Asp Val Glu Thr
                115                 120                 125

Gln Phe Asn Gln Tyr Lys Thr Glu Ala Ala Ser Arg Tyr Asn Leu Thr
130                 135                 140

Ile Ser Asp Val Ser Val Ser Asp Val Pro Phe Pro Phe Ser Ala Gln
145                 150                 155                 160

Ser Gly Ala Gly Val Pro Gly Trp Gly Ile Ala Leu Leu Val Leu Val
                165                 170                 175

Cys Val Leu Val Ala Leu Ala Ile Val Tyr Leu Ile Ala Leu Ala Val
                180                 185                 190

Cys Gln Cys Arg Arg Lys Asn Tyr Gly Gln Leu Asp Ile Phe Pro Ala
                195                 200                 205

Arg Asp Thr Tyr His Pro Met Ser Glu Tyr Pro Thr Tyr His Thr His
210                 215                 220

Gly Arg Tyr Val Pro Pro Ser Ser Thr Asp Arg Ser Pro Tyr Glu Lys
225                 230                 235                 240

Val Ser Ala Gly Asn Gly Gly Ser Ser Leu Ser Tyr Thr Asn Pro Ala
                245                 250                 255

Val Ala Ala Thr Ser Ala Asn Leu
                260

<210> SEQ ID NO 12
<211> LENGTH: 137
<212> TYPE: PRT
<213> ORGANISM: Homo sapiens

<400> SEQUENCE: 12

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
                20                  25                  30

Cys Thr Pro Glu Arg Met Ala Glu Ala Gly Phe Ile His Cys Pro Thr
                35                  40                  45

Glu Asn Glu Pro Asp Leu Ala Gln Cys Phe Phe Cys Phe Lys Glu Leu
50                  55                  60

Glu Gly Trp Glu Pro Asp Asp Asp Pro Met Gln Arg Lys Pro Thr Ile
65                  70                  75                  80

Arg Arg Lys Asn Leu Arg Lys Leu Arg Arg Lys Cys Ala Val Pro Ser
                85                  90                  95

Ser Ser Trp Leu Pro Trp Ile Glu Ala Ser Gly Arg Ser Cys Leu Val
                100                 105                 110

Pro Glu Trp Leu His His Phe Gln Gly Leu Phe Pro Gly Ala Thr Ser
                115                 120                 125

Leu Pro Val Gly Pro Leu Ala Met Ser
                130                 135

<210> SEQ ID NO 13
<211> LENGTH: 1069
<212> TYPE: PRT
<213> ORGANISM: Homo sapiens

<400> SEQUENCE: 13
```

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
            115                 120                 125

Asp Ala Leu Arg Gly Ser Gly Ala Trp Gly Leu Leu Leu Arg Arg Val
        130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415
```

```
Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
```

```
                 835                 840                 845
Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Ser Tyr Ala Arg Thr Ser Ile Arg Ala Ser Leu Thr
                    885                 890                 895

Phe Asn Arg Gly Phe Lys Ala Gly Arg Asn Met Arg Lys Leu Phe
                900                 905                 910

Gly Val Leu Arg Leu Lys Cys His Ser Leu Phe Leu Asp Leu Gln Val
                915                 920                 925

Asn Ser Leu Gln Thr Val Cys Thr Asn Ile Tyr Lys Ile Leu Leu Leu
                930                 935                 940

Gln Ala Tyr Arg Phe His Ala Cys Val Leu Gln Leu Pro Phe His Gln
945                 950                 955                 960

Gln Val Trp Lys Asn Pro Thr Phe Phe Leu Arg Val Ile Ser Asp Thr
                965                 970                 975

Ala Ser Leu Cys Tyr Ser Ile Leu Lys Ala Lys Asn Ala Gly Met Ser
                980                 985                 990

Leu Gly Ala Lys Gly Ala Ala Gly Pro Leu Pro Ser Glu Ala Val Gln
                995                 1000                1005

Trp Leu Cys His Gln Ala Phe Leu Leu Lys Leu Thr Arg His Arg
        1010                1015                1020

Val Thr Tyr Val Pro Leu Leu Gly Ser Leu Arg Thr Ala Gln Thr
        1025                1030                1035

Gln Leu Ser Arg Lys Leu Pro Gly Thr Thr Leu Thr Ala Leu Glu
        1040                1045                1050

Ala Ala Ala Asn Pro Ala Leu Pro Ser Asp Phe Lys Thr Ile Leu
        1055                1060                1065

Asp

<210> SEQ ID NO 14
<211> LENGTH: 449
<212> TYPE: PRT
<213> ORGANISM: Homo sapiens

<400> SEQUENCE: 14

Met Gly Ser Asp Val Arg Asp Leu Asn Ala Leu Leu Pro Ala Val Pro
1               5                   10                  15

Ser Leu Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Ala Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
```

```
            130                 135                 140
Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Val Tyr Gly Cys His Thr Pro Thr Asp Ser
            195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
            275                 280                 285

His Thr His Gly Val Phe Arg Gly Ile Gln Asp Val Arg Val Pro
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
            355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
            435                 440                 445

Leu

<210> SEQ ID NO 15
<211> LENGTH: 9
<212> TYPE: PRT
<213> ORGANISM: Homo sapiens

<400> SEQUENCE: 15

Ser Leu Leu Phe Leu Leu Phe Ser Leu
1               5

<210> SEQ ID NO 16
<211> LENGTH: 9
<212> TYPE: PRT
<213> ORGANISM: Homo sapiens

<400> SEQUENCE: 16
```

Phe Leu Leu Phe Ser Leu Gly Trp Val
1               5

<210> SEQ ID NO 17
<211> LENGTH: 9
<212> TYPE: PRT
<213> ORGANISM: Homo sapiens

<400> SEQUENCE: 17

Val Leu Pro Leu Thr Val Ala Glu Val
1               5

<210> SEQ ID NO 18
<211> LENGTH: 10
<212> TYPE: PRT
<213> ORGANISM: Homo sapiens

<400> SEQUENCE: 18

Lys Leu Leu Gly Pro His Val Glu Gly Leu
1               5                   10

<210> SEQ ID NO 19
<211> LENGTH: 10
<212> TYPE: PRT
<213> ORGANISM: Homo sapiens

<400> SEQUENCE: 19

Lys Leu Leu Gly Pro His Val Leu Gly Leu
1               5                   10

<210> SEQ ID NO 20
<211> LENGTH: 10
<212> TYPE: PRT
<213> ORGANISM: Homo sapiens

<400> SEQUENCE: 20

Lys Leu Leu Gly Pro His Val Leu Gly Val
1               5                   10

<210> SEQ ID NO 21
<211> LENGTH: 10
<212> TYPE: PRT
<213> ORGANISM: Homo sapiens

<400> SEQUENCE: 21

Lys Met Leu Gly Pro His Val Leu Gly Val
1               5                   10

<210> SEQ ID NO 22
<211> LENGTH: 10
<212> TYPE: PRT
<213> ORGANISM: Homo sapiens

<400> SEQUENCE: 22

Lys Met Leu Gly Pro His Val Leu Gly Leu
1               5                   10

<210> SEQ ID NO 23
<211> LENGTH: 10
<212> TYPE: PRT
<213> ORGANISM: Homo sapiens

<400> SEQUENCE: 23

Lys Ile Leu Gly Pro His Val Leu Gly Leu

<210> SEQ ID NO 24
<211> LENGTH: 10
<212> TYPE: PRT
<213> ORGANISM: Homo sapiens

<400> SEQUENCE: 24

Tyr Leu Leu Gly Pro His Val Leu Gly Val
1               5                   10

<210> SEQ ID NO 25
<211> LENGTH: 10
<212> TYPE: PRT
<213> ORGANISM: Homo sapiens

<400> SEQUENCE: 25

Tyr Leu Leu Gly Pro His Val Leu Gly Leu
1               5                   10

<210> SEQ ID NO 26
<211> LENGTH: 9
<212> TYPE: PRT
<213> ORGANISM: Homo sapiens

<400> SEQUENCE: 26

Ser Leu Leu Met Trp Ile Thr Gln Cys
1               5

<210> SEQ ID NO 27
<211> LENGTH: 9
<212> TYPE: PRT
<213> ORGANISM: Homo sapiens

<400> SEQUENCE: 27

Leu Leu Met Trp Ile Thr Gln Cys Phe
1               5

<210> SEQ ID NO 28
<211> LENGTH: 9
<212> TYPE: PRT
<213> ORGANISM: Homo sapiens

<400> SEQUENCE: 28

Glu Ile Trp Thr His Ser Tyr Lys Val
1               5

<210> SEQ ID NO 29
<211> LENGTH: 9
<212> TYPE: PRT
<213> ORGANISM: Homo sapiens

<400> SEQUENCE: 29

Leu Leu Ser Leu Ala Leu Met Leu Leu
1               5

<210> SEQ ID NO 30
<211> LENGTH: 9
<212> TYPE: PRT
<213> ORGANISM: Homo sapiens

<400> SEQUENCE: 30

Ala Leu Cys Arg Trp Gly Leu Leu Leu
1               5

```
<210> SEQ ID NO 31
<211> LENGTH: 9
<212> TYPE: PRT
<213> ORGANISM: Homo sapiens

<400> SEQUENCE: 31

Arg Trp Gly Leu Leu Leu Ala Leu Leu
1               5

<210> SEQ ID NO 32
<211> LENGTH: 9
<212> TYPE: PRT
<213> ORGANISM: Homo sapiens

<400> SEQUENCE: 32

Thr Tyr Leu Pro Thr Asn Ala Ser Leu
1               5

<210> SEQ ID NO 33
<211> LENGTH: 9
<212> TYPE: PRT
<213> ORGANISM: Homo sapiens

<400> SEQUENCE: 33

Gln Leu Phe Glu Asp Asn Tyr Ala Leu
1               5

<210> SEQ ID NO 34
<211> LENGTH: 9
<212> TYPE: PRT
<213> ORGANISM: Homo sapiens

<400> SEQUENCE: 34

Lys Ile Phe Gly Ser Leu Ala Phe Leu
1               5

<210> SEQ ID NO 35
<211> LENGTH: 9
<212> TYPE: PRT
<213> ORGANISM: Homo sapiens

<400> SEQUENCE: 35

Ile Leu His Asn Gly Ala Tyr Ser Leu
1               5

<210> SEQ ID NO 36
<211> LENGTH: 9
<212> TYPE: PRT
<213> ORGANISM: Homo sapiens

<400> SEQUENCE: 36

Ile Ile Ser Ala Val Val Gly Ile Leu
1               5

<210> SEQ ID NO 37
<211> LENGTH: 9
<212> TYPE: PRT
<213> ORGANISM: Homo sapiens

<400> SEQUENCE: 37

Val Val Leu Gly Val Val Phe Gly Ile
1               5

<210> SEQ ID NO 38
```

```
<211> LENGTH: 9
<212> TYPE: PRT
<213> ORGANISM: Homo sapiens

<400> SEQUENCE: 38

Arg Leu Leu Gln Glu Thr Glu Leu Val
1               5

<210> SEQ ID NO 39
<211> LENGTH: 9
<212> TYPE: PRT
<213> ORGANISM: Homo sapiens

<400> SEQUENCE: 39

Val Leu Arg Glu Asn Thr Ser Pro Lys
1               5

<210> SEQ ID NO 40
<211> LENGTH: 10
<212> TYPE: PRT
<213> ORGANISM: Homo sapiens

<400> SEQUENCE: 40

Val Met Ala Gly Val Gly Ser Pro Tyr Val
1               5                   10

<210> SEQ ID NO 41
<211> LENGTH: 9
<212> TYPE: PRT
<213> ORGANISM: Homo sapiens

<400> SEQUENCE: 41

Pro Tyr Val Ser Arg Leu Leu Gly Ile
1               5

<210> SEQ ID NO 42
<211> LENGTH: 9
<212> TYPE: PRT
<213> ORGANISM: Homo sapiens

<400> SEQUENCE: 42

Cys Leu Thr Ser Thr Val Gln Leu Val
1               5

<210> SEQ ID NO 43
<211> LENGTH: 9
<212> TYPE: PRT
<213> ORGANISM: Homo sapiens

<400> SEQUENCE: 43

Gln Leu Met Pro Tyr Gly Cys Leu Leu
1               5

<210> SEQ ID NO 44
<211> LENGTH: 8
<212> TYPE: PRT
<213> ORGANISM: Homo sapiens

<400> SEQUENCE: 44

Tyr Leu Glu Asp Val Arg Leu Val
1               5

<210> SEQ ID NO 45
<211> LENGTH: 9
<212> TYPE: PRT
```

-continued

<213> ORGANISM: Homo sapiens

<400> SEQUENCE: 45

Val Leu Val Lys Ser Pro Asn His Val
1               5

<210> SEQ ID NO 46
<211> LENGTH: 17
<212> TYPE: PRT
<213> ORGANISM: Homo sapiens

<400> SEQUENCE: 46

Lys Val Pro Ile Lys Trp Met Ala Leu Glu Ser Ile Leu Arg Arg Arg
1               5                   10                  15

Phe

<210> SEQ ID NO 47
<211> LENGTH: 10
<212> TYPE: PRT
<213> ORGANISM: Homo sapiens

<400> SEQUENCE: 47

Tyr Met Ile Met Val Lys Cys Trp Met Ile
1               5                   10

<210> SEQ ID NO 48
<211> LENGTH: 9
<212> TYPE: PRT
<213> ORGANISM: Homo sapiens

<400> SEQUENCE: 48

Glu Leu Val Ser Glu Phe Ser Arg Met
1               5

<210> SEQ ID NO 49
<211> LENGTH: 9
<212> TYPE: PRT
<213> ORGANISM: Homo sapiens

<400> SEQUENCE: 49

Trp Leu Pro Phe Gly Phe Ile Leu Ile
1               5

<210> SEQ ID NO 50
<211> LENGTH: 11
<212> TYPE: PRT
<213> ORGANISM: Homo sapiens

<400> SEQUENCE: 50

Ile Thr Lys Lys Val Ala Asp Leu Val Gly Phe
1               5                   10

<210> SEQ ID NO 51
<211> LENGTH: 9
<212> TYPE: PRT
<213> ORGANISM: Homo sapiens

<400> SEQUENCE: 51

Asn Tyr Lys His Cys Phe Pro Glu Ile
1               5

<210> SEQ ID NO 52
<211> LENGTH: 10
<212> TYPE: PRT

<213> ORGANISM: Homo sapiens

<400> SEQUENCE: 52

Lys Glu Ala Asp Pro Thr Gly His Ser Tyr
1               5                   10

<210> SEQ ID NO 53
<211> LENGTH: 9
<212> TYPE: PRT
<213> ORGANISM: Homo sapiens

<400> SEQUENCE: 53

Glu Ala Asp Pro Thr Gly His Ser Tyr
1               5

<210> SEQ ID NO 54
<211> LENGTH: 9
<212> TYPE: PRT
<213> ORGANISM: Homo sapiens

<400> SEQUENCE: 54

Ser Ala Tyr Gly Glu Pro Arg Lys Leu
1               5

<210> SEQ ID NO 55
<211> LENGTH: 9
<212> TYPE: PRT
<213> ORGANISM: Homo sapiens

<400> SEQUENCE: 55

Lys Val Leu Glu Tyr Val Ile Lys Val
1               5

<210> SEQ ID NO 56
<211> LENGTH: 9
<212> TYPE: PRT
<213> ORGANISM: Homo sapiens

<400> SEQUENCE: 56

Leu Leu Trp Gly Cys Ala Leu Ala Ala
1               5

<210> SEQ ID NO 57
<211> LENGTH: 9
<212> TYPE: PRT
<213> ORGANISM: Homo sapiens

<400> SEQUENCE: 57

Ile Met Asn Asp Met Pro Ile Tyr Met
1               5

<210> SEQ ID NO 58
<211> LENGTH: 9
<212> TYPE: PRT
<213> ORGANISM: Homo sapiens

<400> SEQUENCE: 58

Asn Leu Tyr Tyr Ala Glu Ser Asp Leu
1               5

<210> SEQ ID NO 59
<211> LENGTH: 9
<212> TYPE: PRT
<213> ORGANISM: Homo sapiens

<400> SEQUENCE: 59

Lys Leu Asn Val Glu Glu Arg Ser Val
1               5

<210> SEQ ID NO 60
<211> LENGTH: 9
<212> TYPE: PRT
<213> ORGANISM: Homo sapiens

<400> SEQUENCE: 60

Trp Leu Val Pro Ile Gly Gln Cys Leu
1               5

<210> SEQ ID NO 61
<211> LENGTH: 9
<212> TYPE: PRT
<213> ORGANISM: Homo sapiens

<400> SEQUENCE: 61

Gly Leu Thr Arg Thr Ser Val Thr Val
1               5

<210> SEQ ID NO 62
<211> LENGTH: 9
<212> TYPE: PRT
<213> ORGANISM: Homo sapiens

<400> SEQUENCE: 62

Val Leu Leu Leu Val Leu Ala Gly Val
1               5

<210> SEQ ID NO 63
<211> LENGTH: 9
<212> TYPE: PRT
<213> ORGANISM: Homo sapiens

<400> SEQUENCE: 63

Val Leu Ala Gly Val Gly Phe Phe Ile
1               5

<210> SEQ ID NO 64
<211> LENGTH: 9
<212> TYPE: PRT
<213> ORGANISM: Homo sapiens

<400> SEQUENCE: 64

Val Met Trp Glu Val Met Thr Tyr Gly
1               5

<210> SEQ ID NO 65
<211> LENGTH: 9
<212> TYPE: PRT
<213> ORGANISM: Homo sapiens

<400> SEQUENCE: 65

Lys Leu Ile Arg Ala Pro Asp Ser Leu
1               5

<210> SEQ ID NO 66
<211> LENGTH: 9
<212> TYPE: PRT
<213> ORGANISM: Homo sapiens

<400> SEQUENCE: 66

Thr Leu Ala Asp Phe Asp Pro Arg Val
1               5

<210> SEQ ID NO 67
<211> LENGTH: 9
<212> TYPE: PRT
<213> ORGANISM: Homo sapiens

<400> SEQUENCE: 67

Phe Met Ala Ala Gly Tyr Thr Ala Ile
1               5

<210> SEQ ID NO 68
<211> LENGTH: 9
<212> TYPE: PRT
<213> ORGANISM: Homo sapiens

<400> SEQUENCE: 68

Ser Leu Leu Gly Leu Lys Asp Gln Val
1               5

<210> SEQ ID NO 69
<211> LENGTH: 9
<212> TYPE: PRT
<213> ORGANISM: Homo sapiens

<400> SEQUENCE: 69

Arg Met Pro Glu Ala Ala Pro Pro Val
1               5

<210> SEQ ID NO 70
<211> LENGTH: 9
<212> TYPE: PRT
<213> ORGANISM: Homo sapiens

<400> SEQUENCE: 70

Tyr Leu Gly Ser Tyr Gly Phe Arg Leu
1               5

<210> SEQ ID NO 71
<211> LENGTH: 9
<212> TYPE: PRT
<213> ORGANISM: Homo sapiens

<400> SEQUENCE: 71

Lys Thr Cys Pro Val Gln Leu Trp Val
1               5

<210> SEQ ID NO 72
<211> LENGTH: 9
<212> TYPE: PRT
<213> ORGANISM: Homo sapiens

<400> SEQUENCE: 72

Lys Leu Cys Pro Val Gln Leu Trp Val
1               5

<210> SEQ ID NO 73
<211> LENGTH: 9
<212> TYPE: PRT
<213> ORGANISM: Homo sapiens

<400> SEQUENCE: 73

Lys Leu Asx Pro Val Gln Leu Trp Val
1               5

<210> SEQ ID NO 74
<211> LENGTH: 9
<212> TYPE: PRT
<213> ORGANISM: Homo sapiens

<400> SEQUENCE: 74

Ser Thr Pro Pro Pro Gly Thr Arg Val
1               5

<210> SEQ ID NO 75
<211> LENGTH: 9
<212> TYPE: PRT
<213> ORGANISM: Homo sapiens

<400> SEQUENCE: 75

Ser Leu Pro Pro Pro Gly Thr Arg Val
1               5

<210> SEQ ID NO 76
<211> LENGTH: 9
<212> TYPE: PRT
<213> ORGANISM: Homo sapiens

<400> SEQUENCE: 76

Ser Met Pro Pro Pro Gly Thr Arg Val
1               5

<210> SEQ ID NO 77
<211> LENGTH: 11
<212> TYPE: PRT
<213> ORGANISM: Homo sapiens

<400> SEQUENCE: 77

Gly Leu Ala Pro Pro Gln His Leu Ile Arg Val
1               5                   10

<210> SEQ ID NO 78
<211> LENGTH: 9
<212> TYPE: PRT
<213> ORGANISM: Homo sapiens

<400> SEQUENCE: 78

Val Val Pro Tyr Glu Pro Pro Glu Val
1               5

<210> SEQ ID NO 79
<211> LENGTH: 9
<212> TYPE: PRT
<213> ORGANISM: Homo sapiens

<400> SEQUENCE: 79

Leu Leu Gly Arg Asn Ser Phe Glu Val
1               5

<210> SEQ ID NO 80
<211> LENGTH: 9
<212> TYPE: PRT
<213> ORGANISM: Homo sapiens

<400> SEQUENCE: 80

Leu Leu Gly Arg Asn Ser Trp Glu Val
1               5

```
<210> SEQ ID NO 81
<211> LENGTH: 13
<212> TYPE: PRT
<213> ORGANISM: Homo sapiens

<400> SEQUENCE: 81

Lys Leu Val Val Val Gly Ala Gly Gly Val Gly Lys Ser
1               5                   10

<210> SEQ ID NO 82
<211> LENGTH: 13
<212> TYPE: PRT
<213> ORGANISM: Homo sapiens

<400> SEQUENCE: 82

Lys Leu Val Val Val Gly Ala Asp Gly Val Gly Lys Ser
1               5                   10

<210> SEQ ID NO 83
<211> LENGTH: 10
<212> TYPE: PRT
<213> ORGANISM: Homo sapiens

<400> SEQUENCE: 83

Lys Leu Val Val Val Gly Ala Asp Gly Val
1               5                   10

<210> SEQ ID NO 84
<211> LENGTH: 10
<212> TYPE: PRT
<213> ORGANISM: Homo sapiens

<400> SEQUENCE: 84

Lys Leu Val Val Val Gly Ala Val Gly Val
1               5                   10

<210> SEQ ID NO 85
<211> LENGTH: 10
<212> TYPE: PRT
<213> ORGANISM: Homo sapiens

<400> SEQUENCE: 85

Lys Leu Val Val Val Gly Ala Cys Gly Val
1               5                   10

<210> SEQ ID NO 86
<211> LENGTH: 9
<212> TYPE: PRT
<213> ORGANISM: Homo sapiens

<400> SEQUENCE: 86

Tyr Lys Leu Val Val Val Gly Ala Val
1               5

<210> SEQ ID NO 87
<211> LENGTH: 9
<212> TYPE: PRT
<213> ORGANISM: Homo sapiens

<400> SEQUENCE: 87

Val Leu Ala Phe Gly Leu Leu Leu Ala
1               5

<210> SEQ ID NO 88
<211> LENGTH: 11
```

<212> TYPE: PRT
<213> ORGANISM: Homo sapiens

<400> SEQUENCE: 88

Tyr Gln Leu Asp Pro Lys Phe Ile Thr Ser Ile
1               5                   10

<210> SEQ ID NO 89
<211> LENGTH: 10
<212> TYPE: PRT
<213> ORGANISM: Homo sapiens

<400> SEQUENCE: 89

Ile Leu Tyr Glu Asn Asn Val Ile Thr Ile
1               5                   10

<210> SEQ ID NO 90
<211> LENGTH: 10
<212> TYPE: PRT
<213> ORGANISM: Homo sapiens

<400> SEQUENCE: 90

Lys Ala Pro Glu Phe Ser Met Gln Gly Leu
1               5                   10

<210> SEQ ID NO 91
<211> LENGTH: 9
<212> TYPE: PRT
<213> ORGANISM: Homo sapiens

<400> SEQUENCE: 91

Gly Leu Lys Ala Gly Val Ile Ala Val
1               5

<210> SEQ ID NO 92
<211> LENGTH: 9
<212> TYPE: PRT
<213> ORGANISM: Homo sapiens

<400> SEQUENCE: 92

Leu Leu Leu Leu Thr Val Leu Thr Val
1               5

<210> SEQ ID NO 93
<211> LENGTH: 9
<212> TYPE: PRT
<213> ORGANISM: Homo sapiens

<400> SEQUENCE: 93

Ser Thr Ala Pro Pro Val His Asn Val
1               5

<210> SEQ ID NO 94
<211> LENGTH: 11
<212> TYPE: PRT
<213> ORGANISM: Homo sapiens

<400> SEQUENCE: 94

Arg Ile Ser Thr Phe Lys Asn Trp Pro Phe Leu
1               5                   10

<210> SEQ ID NO 95
<211> LENGTH: 15
<212> TYPE: PRT
<213> ORGANISM: Homo sapiens

```
<400> SEQUENCE: 95

Asp Leu Ala Gln Met Phe Phe Cys Phe Lys Glu Leu Glu Gly Trp
1               5                   10                  15

<210> SEQ ID NO 96
<211> LENGTH: 10
<212> TYPE: PRT
<213> ORGANISM: Homo sapiens

<400> SEQUENCE: 96

Glu Leu Thr Leu Gly Glu Phe Leu Lys Leu
1               5                   10

<210> SEQ ID NO 97
<211> LENGTH: 9
<212> TYPE: PRT
<213> ORGANISM: Homo sapiens

<400> SEQUENCE: 97

Leu Thr Leu Gly Glu Phe Leu Lys Leu
1               5

<210> SEQ ID NO 98
<211> LENGTH: 9
<212> TYPE: PRT
<213> ORGANISM: Homo sapiens

<400> SEQUENCE: 98

Leu Met Leu Gly Glu Phe Leu Lys Leu
1               5

<210> SEQ ID NO 99
<211> LENGTH: 9
<212> TYPE: PRT
<213> ORGANISM: Homo sapiens

<400> SEQUENCE: 99

Ile Leu Ala Lys Phe Leu His Trp Leu
1               5

<210> SEQ ID NO 100
<211> LENGTH: 9
<212> TYPE: PRT
<213> ORGANISM: Homo sapiens

<400> SEQUENCE: 100

Tyr Leu Phe Phe Tyr Arg Lys Ser Val
1               5

<210> SEQ ID NO 101
<211> LENGTH: 10
<212> TYPE: PRT
<213> ORGANISM: Homo sapiens

<400> SEQUENCE: 101

Tyr Leu Gln Val Asn Ser Leu Gln Thr Val
1               5                   10

<210> SEQ ID NO 102
<211> LENGTH: 9
<212> TYPE: PRT
<213> ORGANISM: Homo sapiens

<400> SEQUENCE: 102
```

Arg Leu Gly Pro Gln Gly Trp Arg Leu
1               5

<210> SEQ ID NO 103
<211> LENGTH: 9
<212> TYPE: PRT
<213> ORGANISM: Homo sapiens

<400> SEQUENCE: 103

Arg Leu Gly Pro Gln Gly Trp Arg Val
1               5

<210> SEQ ID NO 104
<211> LENGTH: 9
<212> TYPE: PRT
<213> ORGANISM: Homo sapiens

<400> SEQUENCE: 104

Arg Leu Val Asp Asp Phe Leu Leu Val
1               5

<210> SEQ ID NO 105
<211> LENGTH: 9
<212> TYPE: PRT
<213> ORGANISM: Homo sapiens

<400> SEQUENCE: 105

Val Leu Asp Phe Ala Pro Pro Gly Ala
1               5

<210> SEQ ID NO 106
<211> LENGTH: 9
<212> TYPE: PRT
<213> ORGANISM: Homo sapiens

<400> SEQUENCE: 106

Arg Met Phe Pro Asn Ala Pro Tyr Leu
1               5

<210> SEQ ID NO 107
<211> LENGTH: 9
<212> TYPE: PRT
<213> ORGANISM: Homo sapiens

<400> SEQUENCE: 107

Tyr Met Phe Pro Asn Ala Pro Tyr Leu
1               5

<210> SEQ ID NO 108
<211> LENGTH: 9
<212> TYPE: PRT
<213> ORGANISM: Homo sapiens

<400> SEQUENCE: 108

Ser Leu Gly Glu Gln Gln Tyr Ser Val
1               5

<210> SEQ ID NO 109
<211> LENGTH: 9
<212> TYPE: PRT
<213> ORGANISM: Homo sapiens

<400> SEQUENCE: 109

Cys Met Thr Trp Asn Gln Met Asn Leu

```
<210> SEQ ID NO 110
<211> LENGTH: 10
<212> TYPE: PRT
<213> ORGANISM: Homo sapiens

<400> SEQUENCE: 110

Glu Leu Ala Gly Ile Gly Ile Leu Thr Val
1               5                   10

<210> SEQ ID NO 111
<211> LENGTH: 9
<212> TYPE: PRT
<213> ORGANISM: Homo sapiens

<400> SEQUENCE: 111

Ser Leu Phe Arg Ala Val Ile Thr Lys
1               5

<210> SEQ ID NO 112
<211> LENGTH: 13
<212> TYPE: PRT
<213> ORGANISM: Homo sapiens

<400> SEQUENCE: 112

Ala Lys Phe Val Ala Ala Trp Thr Leu Lys Ala Ala Ala
1               5                   10

<210> SEQ ID NO 113
<211> LENGTH: 16
<212> TYPE: PRT
<213> ORGANISM: Homo sapiens

<400> SEQUENCE: 113

Ala Gln Tyr Ile Lys Ala Asn Ser Lys Phe Ile Gly Ile Thr Glu Leu
1               5                   10                  15

<210> SEQ ID NO 114
<211> LENGTH: 9
<212> TYPE: PRT
<213> ORGANISM: Homo sapiens

<400> SEQUENCE: 114

Glu Ile Trp Thr His Ser Thr Lys Val
1               5
```